United States Patent
Khan et al.

(10) Patent No.: US 11,903,640 B2
(45) Date of Patent: Feb. 20, 2024

(54) ROBOT-ASSISTED LASER SURGICAL SYSTEM

(71) Applicant: Australian Institute of Robotic Orthopaedics Pty Ltd, Nedlands Perth (AU)

(72) Inventors: Riaz Jan Kjell Khan, Cottesloe (AU); Daniel Paul Fick, Cottesloe (AU); William Brett Robertson, North Fremantle (AU); Raymond Ka-Man Sheh, Bentley (AU); Charles Ironside, South Perth (AU); Richard Chipper, Mount Claremont (AU)

(73) Assignee: Australian Institute of Robotic Orthopaedics Pty Ltd, Nedlands Perth (AU)

( * ) Notice: Subject to any disclaimer, the term of this patent is extended or adjusted under 35 U.S.C. 154(b) by 6 days.

(21) Appl. No.: 17/663,971

(22) Filed: May 18, 2022

(65) Prior Publication Data
US 2022/0346875 A1   Nov. 3, 2022

Related U.S. Application Data

(63) Continuation of application No. 16/324,092, filed as application No. PCT/AU2017/050840 on Aug. 9, 2017, now Pat. No. 11,369,435.

(30) Foreign Application Priority Data

Aug. 10, 2016   (AU) ................. 2016903144

(51) Int. Cl.
*A61B 18/20*   (2006.01)
*A61B 34/10*   (2016.01)
(Continued)

(52) U.S. Cl.
CPC .............. *A61B 18/20* (2013.01); *A61B 17/16* (2013.01); *A61B 18/203* (2013.01); *A61B 34/10* (2016.02);
(Continued)

(58) Field of Classification Search
CPC ....... A61B 17/16; A61B 18/20; A61B 18/203; A61B 2017/00061; A61B 2017/00066;
(Continued)

(56) References Cited

U.S. PATENT DOCUMENTS 6,538,739 B1   3/2003   Visuri et al.
7,831,292 B2   11/2010   Quaid et al.
(Continued)

FOREIGN PATENT DOCUMENTS

WO   WO-2014102355 A1   7/2014

OTHER PUBLICATIONS

"U.S. Appl. No. 16/324,092, Corrected Notice of Allowability dated Mar. 3, 2022", 2 pgs.
(Continued)

*Primary Examiner* — Amanda K Hulbert
(74) *Attorney, Agent, or Firm* — Schwegman Lundberg & Woessner, P.A.

(57) ABSTRACT

A system for working biological tissue, the system comprising: a tool comprising a laser operable to perform at least one action of work; positioning means for positioning the tool relative to the biological tissue to perform the at least one action of work; a controller; storage storing electronic program instructions for controlling the controller; and an input means; wherein the controller is operable, under control of the electronic program instructions, to: receive input via the input means; process the input and, on the basis of the processing, control the positioning means and the tool to work the biological tissue.

18 Claims, 31 Drawing Sheets

(51) Int. Cl.
| | |
|---|---|
| *A61B 34/30* | (2016.01) |
| *A61B 34/32* | (2016.01) |
| *A61B 17/16* | (2006.01) |
| *A61B 34/35* | (2016.01) |
| *A61B 90/50* | (2016.01) |
| *A61B 17/00* | (2006.01) |
| *A61B 18/00* | (2006.01) |
| *A61B 34/20* | (2016.01) |
| *A61B 90/00* | (2016.01) |
| *A61B 90/30* | (2016.01) |
| *A61F 2/38* | (2006.01) |

(52) U.S. Cl.
CPC .............. *A61B 34/30* (2016.02); *A61B 34/32* (2016.02); *A61B 34/35* (2016.02); *A61B 90/50* (2016.02); *A61B 2017/00061* (2013.01); *A61B 2017/00066* (2013.01); *A61B 2017/00106* (2013.01); *A61B 2017/00203* (2013.01); *A61B 2018/00029* (2013.01); *A61B 2018/0066* (2013.01); *A61B 2018/00565* (2013.01); *A61B 2018/00577* (2013.01); *A61B 2018/00642* (2013.01); *A61B 2018/00785* (2013.01); *A61B 2018/00809* (2013.01); *A61B 2018/2025* (2013.01); *A61B 2018/20351* (2017.05); *A61B 2018/20359* (2017.05); *A61B 2034/104* (2016.02); *A61B 2034/2048* (2016.02); *A61B 2034/2055* (2016.02); *A61B 2034/2065* (2016.02); *A61B 2034/302* (2016.02); *A61B 2090/306* (2016.02); *A61B 2090/3614* (2016.02); *A61B 2090/3735* (2016.02); *A61B 2090/3916* (2016.02); *A61B 2090/3937* (2016.02); *A61B 2218/001* (2013.01); *A61B 2218/002* (2013.01); *A61B 2218/007* (2013.01); *A61F 2/389* (2013.01)

(58) Field of Classification Search
CPC ........... A61B 2017/00106; A61B 2017/00203; A61B 2018/00029; A61B 2018/00565; A61B 2018/00577; A61B 2018/00642; A61B 2018/0066; A61B 2018/00785; A61B 2018/00809; A61B 2018/2025; A61B 2018/20351; A61B 2018/20359; A61B 2034/104; A61B 2034/2048; A61B 2034/2055; A61B 2034/2065; A61B 2034/302; A61B 2090/306; A61B 2090/3614; A61B 2090/3735; A61B 2090/3916; A61B 2090/3937; A61B 2218/001; A61B 2218/002; A61B 2218/007; A61B 34/10; A61B 34/30; A61B 34/32; A61B 34/35; A61B 90/50; A61F 2/389

See application file for complete search history.

(56) References Cited

U.S. PATENT DOCUMENTS

| | | |
|---|---|---|
| 2004/0106916 A1 | 6/2004 | Quaid et al. |
| 2011/0190760 A1 | 8/2011 | Niver et al. |
| 2012/0184955 A1 | 7/2012 | Pivotto et al. |
| 2012/0220992 A1 | 8/2012 | Bruno et al. |
| 2014/0066764 A1 | 3/2014 | Subramaniam et al. |
| 2015/0105765 A1 | 4/2015 | Panescu et al. |
| 2016/0081745 A1 | 3/2016 | Rajagopalan et al. |
| 2019/0175272 A1 | 6/2019 | Khan et al. |

OTHER PUBLICATIONS

"U.S. Appl. No. 16/324,092, Final Office Action dated Dec. 15, 2020", 20 pgs.

"U.S. Appl. No. 16/324,092, Non Final Office Action dated Jun. 11, 2020", 23 pgs.

"U.S. Appl. No. 16/324,092, Non Final Office Action dated Jun. 28, 2021", 21 pgs.

"U.S. Appl. No. 16/324,092, Notice of Allowance dated Feb. 24, 2022", 6 pgs.

"U.S. Appl. No. 16/324,092, Preliminary Amendment filed May 3, 2019", 12 pgs.

"U.S. Appl. No. 16/324,092, Response filed Mar. 11, 2021 to Final Office Action dated Dec. 15, 2020", 10 pgs.

"U.S. Appl. No. 16/324,092, Response filed Oct. 13, 2020 to Non Final Office Action dated Jun. 11, 2020", 11 pgs.

"U.S. Appl. No. 16/324,092, Response filed Oct. 28, 2021 to Non Final Office Action dated Jun. 28, 2021", 10 pgs.

"European Application Serial No. 17838216.4 Extended Search Report dated Feb. 20, 2020", (dated Feb. 20, 2020), 11 pgs.

"International Application Serial No. PCT/AU2017/050840, International Search Report dated Oct. 27, 2017", (dated Oct. 27, 2017), 6 pgs.

"International Application Serial No. PCT/AU2017/050840, Written Opinion dated Oct. 27, 2017", (dated Oct. 27, 2017), 8 pgs.

Burgner, Jessica, "Robot Assisted Laser Osteotomy", Available online: https://www.ksp.kit.edu/9783866444973, (2014), 248 pgs.

Kuttenberger, Johannes J., et al., "Computer-guided CO2-laser osteotomy of the sheep tibia: technical prerequisites and first results", Photomedicine and laser surgery vol. 26 No. 2, (2008), 129-136.

ROBOT-ASSISTED LASER SURGICAL SYSTEM

CLAIM FOR PRIORITY

This application is a continuation of U.S. Application Ser. No. 16/324,092, filed Feb. 7, 2019, which is a U.S. National Stage Filing under 35 U.S.C. 371 from International Application No. PCT/AU2017/050840, filed on Aug. 9, 2017, and published as WO2018/027269 on Feb. 15, 2018, which claims the benefit of priority to Australian Application No. 2016903144, filed on Aug. 10, 2016; the benefit of priority of each of which is hereby claimed herein, and which applications and publication are hereby incorporated herein by reference in their entireties.

TECHNICAL FIELD

The present invention relates generally to performing work in respect of laser shaping of biological tissue including bone.

Although the present invention will be described with particular reference to work comprising one or more actions of an orthopaedic surgical procedure performed on dynamic material comprising biological tissue of a living human being, it will be appreciated that implementations of the invention may be used in respect of other biological tissue, and for work comprising additional and/or alternative actions.

BACKGROUND

Any discussion of the background art throughout the specification should in no way be considered as an admission that such background art is prior art, nor that such background art is widely known or forms part of the common general knowledge in the field in Australia or worldwide.

Biological tissue can be difficult to work.

One type of biological tissue that is difficult to work is bone. From a materials processing point of view, hard biological tissue, such as bone, is an unfavourable material due to its complex physical nature based on multicomponent (calcium phosphate (ceramic), collagen (organic), and water) and hierarchical structure.

Osteotomy is the surgical cutting of bone. This technique is routinely used in orthopaedic surgery, for example during joint arthroplasty in which parts of an arthritic or damaged joint are removed and replaced with one or more components such as an implant/prosthesis intended to replicate movement of a normal, healthy joint.

A cutting process forms one of the important bone shaping operations during orthopaedic surgeries. Successful joint arthroplasty relies on accurate and precise osteotomy to ensure the alignment of the components and the security of fixation to the bone. Accuracy and quality of bone preparation are key factors in long term implant survivability and good clinical outcome.

For example, the outcome for a recipient of Total Knee Replacement (TKR) surgery is largely dependent on the accuracy of the set of resections performed as part of the surgery to match the internal geometry of the prosthetic implants. Each resection can differ from the ideal cut plane in terms of the position, angle, and flatness of the resulting surface. Inaccuracies in the position and angle result in poor function of the prosthetic as well as potential looseness of the implant. Inaccuracies in the flatness of any surface results in "point loading" that can damage the bone and affects the positioning of the implant—decreasing the longevity of the implant and the quality of life of the patient.

As will be described in further detail, current joint surgical techniques lack accuracy in positioning the resections. It has been reported that 20% of total knee replacement patients are dissatisfied with the outcome of the surgery post-operatively and aseptic loosening continues to persist as the leading cause of revision within 10 years of surgery.

Orthopaedic surgery has come a long way through adaptation/integration of modern tools such as sensors and computer aided design (CAD) based generation of patient specific defined joint design and bone machining (shaping/cutting) parameters. That said, currently to perform osteotomy surgeons use conventional mechanical tools such as saws, drills, hammers, ultrasonic cutters, chisels, and grinders. These instruments suffer from a number of disadvantages, including that they lack accuracy and submillimetre precision, cause thermal damage, transfer vibrations and biomechanical stress to adjacent bone, and can cause bone fragmentation.

Particularly, conventional sawing techniques produce uneven bone surfaces with gaps large enough to affect the fixation and position of the implant. Modern surgical instrumentation incorporates various features (such as narrow slots to guide saw blades) that are designed to improve resection accuracy. Nevertheless, making precise bone cuts with current instrumentation in the clinical setting is difficult, and varus-valgus cutting errors of 4 degrees and flexion-extension errors of 10 degrees have been reported. Clinical studies have shown that successful bone ingrowth into porous coating necessitates both close bone apposition to the porous surface and sufficient initial fixation of the implant. Furthermore, the heat generated by mechanical osteotomy, caused by friction along with heavy mechanical loading, can lead to tissue necrosis (death). Tissue necrosis adversely affects the bony integration into the implant reducing long-term implant survivability.

Currently orthopaedic surgeons rely on a combination of mechanical cutting tools used in conjunction with cutting jigs, computer navigation, and patient matched cutting blocks. Whilst these tools are currently widely accepted as gold standard they each have an inherent degree of error. The accumulative impact of this error is multiplied exponentially when additional factors such as surgeon experience and technical competence are accounted for.

Indeed, the conventional way of orthopaedic surgery is associated with human and tool attributes that mostly result in potentially increasing the risk of thermal damage (necrosis). This situation in turn leaves tremendous room for further development of operating tools and techniques. Further developments are needed to address the adverse effects of orthopaedic surgery including, but not limited to, 1) severe damage of tissues within and surrounding repaired/operated regions, 2) low precision in final dimensional tolerance on repaired/operated bone, 3) relatively slow surgical processes, 4) post-surgery tissue trauma, 5) rigorous pain, and 6) in some cases, post-surgery complications requiring further surgery and related addition of cost and 7) low precision in final component positioning.

Cutting saw and osteotomes are the traditional tools employed for bone cutting during orthopaedic surgery. Newer techniques include burrs. Being a manual operation, it involves human errors and necessity of skilled surgeons thus making achievement of reproducibility difficult. Apart from these variabilities, there are other issues associated with their use, such as the above mentioned thermally driven necrosis of tissues initiated by temperature rise due to the extended period of physical contact between the cutting/shaping tool and bone that leads to friction/abrasion between the cutting tool and bone along with heavy mechanical loading of bones during conventional mechanical shaping/cutting. In general, cutting saw blades are much harsher than cutting burrs, with temperatures of bone rising above 100° C. The reason behind this increase in temperature is the large contact area of bone with the teeth of the saw. In addition, there are many cuts that need to be performed in order to shape the bone. Although the cutting operation using a burr results in moderate temperatures (50-60° C.), burr cutting is limited to shallow cuts, and is thus not an ideal substitute for the cutting saw.

To address the temperature rise and avoid associated necrosis, many remedies have been explored that are mainly focused on (a) change in tool design, (b) improving method of operation, and most prevalent (c) employing saline cooling. Out of these, (a), and (b) still require careful operational procedures to achieve lower heat generation. In the case of (c), even though the temperature rise can be controlled, designing an effective cooling system becomes necessary. For cutting tools, internally cooled tools have been reported to be superior in terms of heat control than an external spray/mist cooling. Intricately designed tools and careful temperature and flow rate control are required to achieve low heat generation. Furthermore, due to the physical contact between the mechanical cutting tools and bone, a very cautious sterilization process for tools is required to avoid any risk of infection. Apart from these issues, the conventional bone shaping/cutting also involves post tissue trauma, rigorous pain and long healing/recovery times.

Osteoarthritis (OA) is a leading cause of disability in developed nations. In Australia it afflicts 16.5% of the adult population (3.9 million Australians). Total joint arthroplasty is considered the treatment of choice for end stage osteoarthritis. The number of total joint arthroplasties undertaken in Australia has doubled over the last decade with more than 80,000 procedures performed during 2014 at a cost to the Australian health system of over AUD 1 billion.

According to the World Health Organisation (WHO), by 2050 130 million people will suffer from OA worldwide, of whom 40 million will be severely disabled by the disease.

Compelling demographic trends, such as the growing, aging and more active population and rising obesity rates are expected to be key drivers in the continued growth of OA. According to the United Nations, by 2050 people aged over 60 will account for more than 20% of the world's population. Of that 20%, a conservative estimate of 15% will have symptomatic OA, and one-third of these people will be severely disabled. According to the WHO, it is estimated that in 2014 more than 1.9 billion adults, 18 years and older, were overweight. Of these over 600 million were obese. According to the American Journal of Epidemiology, obese women had nearly four times the risk of suffering from OA of the knee as non-obese women, and obese men had nearly five times the risk of suffering from OA of the knee as non-obese men.

For the most severe cases of OA, in which patients suffer from extreme pain, reconstructive joint surgery may be required. Reconstructive joint surgery involves the removal of the bone area surrounding the affected joint and the insertion of one or more manufactured implants as a replacement for the affected bone. According to Knowledge Enterprises, Inc., the joint replacement product market as a whole, including knees, hips, elbows, wrists, digits and shoulders, is estimated to have approached $14.9 billion worldwide in 2013. According to Frost & Sullivan, the global joint implant market in 2014 was $34.9 billion, with knee and hip implant systems representing the two largest sectors.

It is against this background that the present invention has been developed.

SUMMARY

It is an object of the present invention to overcome or ameliorate at least one or more of the disadvantages of the prior art, or to provide a useful alternative.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Any one of the terms: "including" or "which includes" or "that includes" as used herein is also an open term that also means including at least the elements/features that follow the term, but not excluding others. Thus, "including" is synonymous with and means "comprising".

In the claims, as well as in the summary above and the description below, all transitional phrases such as "comprising," "including," "carrying," "having," "containing," "involving," "holding," "composed of," and the like are to be understood to be open-ended, i.e., to mean "including but not limited to". Only the transitional phrases "consisting of" and "consisting essentially of" alone shall be closed or semi-closed transitional phrases, respectively.

The term "real-time", for example, "displaying real-time data," refers to the display of the data without intentional delay, given the processing limitations of the system and the time required to accurately measure the data.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or", as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

For the purpose of this specification, where method steps are described in sequence, the sequence does not necessarily mean that the steps are to be carried out in chronological order in that sequence, unless there is no other logical manner of interpreting the sequence.

In addition, where features or aspects of the invention are described in terms of Markush groups, those skilled in the art will recognise that the invention is also thereby described in terms of any individual member or subgroup of members of the Markush group.

Embodiments of the present invention seek to overcome, or at least ameliorate, one or more of the deficiencies of the prior art mentioned above, or to provide the consumer with a useful or commercial choice.

Other advantages of embodiments of the present invention will become apparent from the following description, taken in connection with the accompanying drawings, wherein, by way of illustration and example, preferred embodiments of the present invention are disclosed.

According to a first aspect of the invention, there is provided a robot-assisted laser osteotomy system for laser shaping of biological tissue including bone. The system may comprise a tool comprising a laser operable to perform at least one action of work. The system may further comprise positioning means for positioning the tool relative to the biological tissue to perform the at least one action of work. The system may further comprise a controller. The system may further comprise storage storing electronic program instructions for controlling the controller. The system may further comprise an input means. The controller may be operable, under control of the electronic program instructions, to receive input via the input means. The controller may be further operable to process the input. On the basis of the processing, the controller may be further operable to control the positioning means and the tool to work the biological tissue.

According to a particular arrangement of the first aspect, there is provided a robot-assisted laser osteotomy system for laser shaping of biological tissue including bone, the system comprising:
  a tool comprising a laser operable to perform at least one action of work;
  positioning means for positioning the tool relative to the biological tissue to perform the at least one action of work;
  a controller;
  storage storing electronic program instructions for controlling the controller; and
  an input means;
wherein the controller is operable, under control of the electronic program instructions, to:
  receive input via the input means;
  process the input and, on the basis of the processing, control the positioning means and the tool to work the biological tissue.

Embodiments and implementations of the above described aspect, and those aspects described below, may incorporate one or more of the following optional features.

The processing of input performed by the controller may comprise an analysis of the input and a making of a decision on the basis of the analysis. Once a decision has been made, the controller is operable, under control of the electronic program instructions, to initiate an action on the basis of the decision to control the positioning means and the tool to work the biological tissue.

In one embodiment, as at least part of the analysis, the controller is operable, under control of the electronic program instructions, to: generate based on input, or receive as input, one or more criteria relevant to the at least one action of work; and use the criteria in the making of the decision.

In another embodiment, the criteria comprise at least one of: speed of the at least one action of work; accuracy of the at least one action of work; safety of the at least one action of work; and cleanliness of the at least one action of work.

As at least part of the analysis, the controller may be operable, under control of the electronic program instructions, to generate based on input, or receive as input, a representation of the biological tissue. The controller may be further operable to generate based on input, or receive as input, an other representation of the biological tissue, the other representation of the biological tissue being a different representation of the biological tissue. The controller may be further operable to make an assessment on the basis of the representation of the biological tissue and the other representation of the biological tissue, and use the assessment in the making of the decision.

The representation of the biological tissue may comprise a representation of a state of the biological tissue. The state of the biological tissue may correspond to a planned state of the biological tissue after the at least one action of work has been performed thereon.

The other representation of the biological tissue may comprise a representation of an other state of the biological tissue. The other state of the biological tissue may correspond to an actual state of the biological tissue after the at least one action of work has been performed thereon.

Making the assessment may comprise comparing the actual state of the biological tissue after the at least one action of work has been performed thereon with the planned state of the biological tissue.

The input means may comprise at least one sensor, which may be part of a sensor system or a set of sensors. Individual sensors within the set of sensors are operable to monitor, sense and gather or measure sensor data and/or information associated with or relating to one or more characteristics, properties and/or parameters of one or more of the system, the biological tissue, and the surrounding environment, or components, systems or devices associated therewith or coupled thereto.

Sensors of the set of sensors may include those based on: Raman spectroscopy; hyperspectral imaging; optical imaging; thermal imaging; fluorescence spectroscopy, microscopy; acoustic, 3D metrology, optical coherence tomography, laser power, and any non-invasive sensing.

Operations performed by the system may occur semi-automatically under the control of a surgeon, or automatically without requiring human intervention.

The at least one action of work may be part of surgical procedure, and preferably an orthopaedic surgical procedure.

The tool may comprise a laser operable to perform subtractive ablation as the at least one action of work.

In one embodiment, the processing of the input comprises optimising the operation of the laser based on the dynamics of the interaction between a beam of radiation generated by the laser and the biological tissue to increase rate of the ablation.

In another embodiment, optimising comprises seeking to increase or maximise the volume of biological tissue ablated taking into account criteria including at least one of safety and accuracy.

In a further embodiment, beams of radiation are generated by the laser in pulses, and laser pulses are batched into ablation runs comprising a pre-calculated set of pulses at different locations across the biological tissue.

In one embodiment, the control comprises operating the laser at a lower power to reduce or mitigate damage to a final surface of the biological tissue after the ablation has been performed thereon.

In another embodiment, the system comprises cooling means for cooling one or more components of the system.

In a further embodiment, the cooling means comprises a coolant chiller for chilling a coolant for cooling the laser.

In one embodiment, the optimising operation of the laser comprises a sprayer for spraying a liquid to the biological tissue to assist in laser ablation and protect the biological tissue from thermal damage to at least some extent.

In another embodiment, the sprayer liquid comprises water or a water-derived solution such as, for example, saline, and preferably is sterilised prior to use. In alternative embodiments, the sprayer liquid comprises a bio-compatible (i.e. non-toxic & inert) solution adapted for acting as a coolant to the biological tissue as well as being capable of absorbing the laser radiation to assist in the ablation process.

In a further embodiment, the cooling means comprises a bundle of at least two partitioned insulated conduits.

In one embodiment, the system comprises shielding for providing protection during working of the biological tissue.

In another embodiment, the shielding comprises a consumable shield.

In a further embodiment, the consumable shield comprises a particle collector and/or a series of filters and/or traps for filtering and storing particulate matter.

In one embodiment, the positioning means comprises a robot arm.

In another embodiment, a working portion of the tool is provided on an end effector of the robot arm.

In a further embodiment, the system comprises a fine motion means for directing the working portion of the tool with increased accuracy.

In one embodiment, when the input comprises input from a 3D metrology sensor, the processing comprises using the input to map the geometry of the biological tissue and the surrounding environment.

In another embodiment, the processing further comprises reducing the dimensionality of the three-dimensional (3D) geometry into a set or series of two-dimensional (2D) maps on the basis of a planar, spherical, cylindrical, or any other coordinate system for converting between 3D and 2D.

In a further embodiment, the processing further comprises overlaying other sensor information on the same 2D map.

In one embodiment, when the input comprises input from a hyperspectral sensor, Raman spectroscopy sensor, microscopy sensor, optical imaging sensor, or optical coherence tomography, the processing comprises using the input to differentiate between biological tissues and, potentially, the constituent composition of materials.

In another embodiment, when the input comprises input from a thermal sensor, the processing comprises using the input to determine any temperature effects, such as thermal damage, to the worked biological tissue and any further effects that would likely result with further working.

In another embodiment, when the input comprises input from an acoustic sensor, the processing comprises using the acoustic sensor input to detect if the tool has worked an unintended or unexpected biological tissue or material.

In another embodiment, when the input comprises input from a laser power sensor, the processing comprises using the input to determine the actual power being produced by the laser beam.

In a further embodiment, the system comprises a fiducial mark provided on the biological tissue by the laser for tracking thereof.

In one embodiment, when the input comprises input from at least one sensor, the processing comprises using the sensor input to refine control of the positioning means and the tool to work the biological tissue.

In another embodiment, the controller comprises an intelligent controller for providing intelligent control of the system.

In a further embodiment, the intelligent controller comprises a master system coordinator for controlling operations of the system, including one or more of simulation, testing, and data logging operations.

In a further embodiment, the intelligent controller comprises Artificial Intelligence (A.I.) software including, but not limited to, machine perception or machine learning.

In a further embodiment, the system further comprises dynamic focusing optics and a dynamic focusing optics controller; the dynamic focusing optics operable to dynamically change the focal length and focus beam diameter of the laser beam at a target distance determined as desirable by the controller via the dynamic focusing optics controller.

According to a second aspect of the invention, there is provided a method for working biological tissue. The method may comprise the step of storing electronic program instructions for controlling a controller. The method may comprise the further step of controlling the controller via the electronic program instructions, to receive input via an input means. The method may comprise the further step of controlling the controller via the electronic program instructions, to process the input and, on the basis of the processing, control a tool operable to perform at least one action of work and positioning means for positioning the tool relative to the biological tissue to perform the at least one action of work, to work the biological tissue.

According to a particular arrangement of the second aspect, there is provided a method for working biological tissue, the method comprising:
storing electronic program instructions for controlling a controller; and
controlling the controller via the electronic program instructions, to:
receive input via an input means; and
process the input and, on the basis of the processing, control a tool operable to perform at least one action of work and positioning means for positioning the tool relative to the biological tissue to perform the at least one action of work, to work the biological tissue.

According to a third aspect of the invention, there is provided a computer-readable storage medium on which is stored instructions that, when executed by a computing means, causes the computing means to perform the method according to the second broad aspect as hereinbefore described.

According to a fourth aspect of the invention, there is provided a computing means programmed to carry out the method according to the second broad aspect as herein before described.

According to a fifth aspect of the invention, there is provided a data signal including at least one instruction being capable of being received and interpreted by a computing system, wherein the instruction implements the method according to the second broad aspect as hereinbefore described.

According to a sixth aspect of the invention, there is provided a computer program product having a computer readable medium having a computer program recorded therein for working biological tissue, the computer readable medium comprising instructions for controlling a controller, said computer program product comprising: computer program code means for controlling the controller via the electronic program instructions; computer program code means for receiving input via an input means; and computer program code means for processing the input and, on the basis of the processing, control a tool operable to perform at least one action of work and positioning means for positioning the tool relative to the material to perform the at least one action of work, to work the biological tissue.

According to a seventh aspect of the invention, there is provided a computer program for working biological tissue, said program comprising: code for retrieving instructions for controlling a controller, said instructions being stored in a computer readable medium; code for controlling the controller via the electronic program instructions; and code for receiving input via an input means; and code for processing the input and, on the basis of the processing, control a tool operable to perform at least one action of work and positioning means for positioning the tool relative to the material to perform the at least one action of work, to work the biological tissue.

According to an eighth aspect of the invention, there is provided an electronic device comprising: an input component configured to receive inputs from a user; an output component configured to provide outputs to the user; a processor coupled to the input component and the output component; and a computer-readable storage medium containing program instructions, that, when executed by the processor, cause the processor to: retrieve instructions for controlling a controller, said instructions being stored in a computer readable medium control the controller via the electronic program instructions, to: receive input via an input means; and process the input and, on the basis of the processing, control a tool operable to perform at least one action of work and positioning means for positioning the tool relative to the material to perform the at least one action of work, to work the biological tissue.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which.

DETAILED DESCRIPTION

Figure 1:
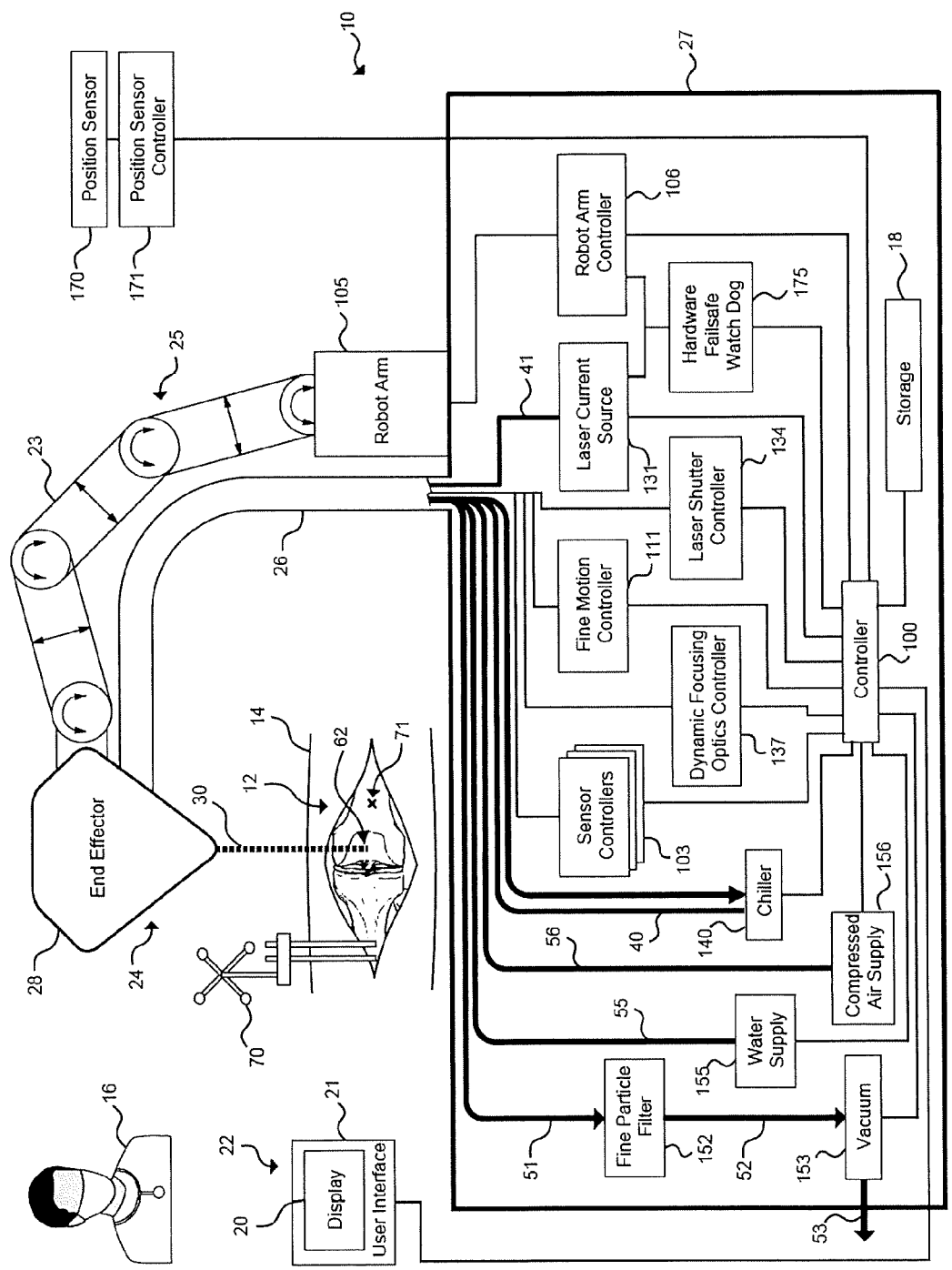
FIG. 1 depicts a high-level physical system architecture of an embodiment of a system in accordance with aspects of the present invention.

The present invention is not to be limited in scope by the following specific embodiments. This detailed description is intended for the purpose of exemplification only. Functionally equivalent products, compositions and methods are within the scope of the invention as described herein. Consistent with this position, those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

Further features of the present invention are more fully described in the examples herein. It is to be understood, however, that this detailed description is included solely for the purposes of exemplifying the present invention, and should not be understood in any way as a restriction on the broad description of the invention as set out hereinbefore.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Furthermore, throughout this specification, unless the context requires otherwise, the word "include", or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

Throughout this specification relative language such as the words 'about' and 'approximately' are used. This language seeks to incorporate at least 10% variability to the specified number or range. That variability may be plus 10% or negative 10% of the particular number specified.

In the drawings, like features have been referenced with like reference numbers.

From the discussion of the background art herein, it is evident that conventional cutting/shaping techniques, in spite of having short comings, are still in use. The embodiment of the invention seeks to improve this situation by aiming at the elimination of (a) complex system arrangements, (b) variabilities introduced by human factors, and (c) physical contact between the cutting/shaping tool and bone.

To this end, the implementation takes a different approach so as to seek a superior shaping/cutting operation. It is based on the employment of an extremely short duration, non-physical contact, high intensity laser beam as an energy source for shaping/cutting. The pulse width (alternatively pulse duration) of laser pulses from laser module 130 may be in the range of between about 0.1 to 1000 μs. The average output power of the laser from laser module 130 may be in the range of between about 0.1 to 2000 W. Such a high intensity focused laser beam may advantageously conduct bone material removal in an extremely short time duration without causing any, or at least reducing, thermal necrosis and mechanical damage to the material surrounding the bone-laser interaction region 63. The laser beam 30 is focused to a spot on the biological material 12 with a spot size of typically between about 300 and 1000 μm in diameter so as to deliver laser energy to the biological material 12 for ablating the material with laser energy having an energy density (fluence) in the range of between about 0.1 to 1000 $J/cm^2$ and, under normal operation, typically in the range of between about 10 to 150 $J/cm^2$. Furthermore, as will be described in further detail, the disclosed laser based bone shaping/cutting technique is highly amenable to automation and reduction in human intervention and operation time along with increasing precision in shaping/cutting. In addition, these primary advantages may lead to secondary benefits such as rapid patient recovery and reduction in cost.

Any laser types suitable for bone shaping/cutting operation may be used for example: gas lasers such as a $CO_2$ laser (having emission wavelength between about 9 μm to about 12 μm), or solid state lasers including: Er:YAG laser (wavelength: 2940 nm), Nd:YAG laser (wavelength: 1064 nm), Tm:YAG laser (wavelength: 2000 nm), Ho:YAG laser (wavelength: 2100 nm) or other suitable laser system as would be appreciated by the skilled addressee, preferably having an emission wavelength compatible with absorption by water which is abundant in biological tissue and which can also be applied to the interaction site to increase the efficiency of the ablation process thorough interaction between the laser radiation 30 and a water-based solution. Water has a significant absorption coefficient around 3 μm so a laser source capable of laser emission about this absorption peak (for example an Er:YAG laser emitting at 2940 nm is particularly suited to laser ablation processes in biological material 12). It should be appreciated that the proposed laser based shaping is well suited for semi or full automation.

In FIG. 1, there is depicted an embodiment of a system 10 for working biological tissue 12 in accordance with aspects of the present invention, illustrated at a high-level as an interconnected collection of physical components.

In the embodiment described, the biological tissue 12 is dynamic material comprising a portion of patient 14 that is a living human being. The work comprises one or more actions of a surgical procedure to be performed on the patient 14. The biological tissue 12 comprises soft tissue, such as cartilage, and hard tissue, such as bone, of which a subsection is able to be ablated away by the system 10 to result in a resectioned surface, which, for joint arthroplasty, is ideal for the prosthetic implant. The so-called "dynamic" nature of the biological tissue 12 indicates that it may shift or move during the procedure and this needs to be accounted for in the method of ablation to ensure that the surface is accurately targeted, discussed in further detail hereafter.

The system 10 may be referred to as an Intelligent Robot Assisted Subtractive Laser Ablation System (IRASLAS™) and, as will be described, is operable to perform one or more resections required for osteotomy, joint arthroplasty, or any other orthopaedic or reconstructive procedure, using computer controlled robotic positioning, precise laser ablation and sensors to assess the process and report on the resulting geometry.

However, it will be appreciated that the invention is not limited in regard to the biological tissue worked, the purpose for which it is worked, or the action(s) of the work performed, and in alternative embodiments, the invention may be applied to working additional and/or alternative materials, including dynamic and static materials, via work comprising additional and/or alternative actions to those described. Depending on the implementation, the material may be a body of a living thing, or one or more parts thereof, or a body of a non-living thing, or one or more parts thereof.

The system 10 comprises a plurality of components, subsystems and/or modules operably coupled via appropriate circuitry, computer chips (integrated circuits), transceiver/receiver antenna, software and connections to enable the system 10 to advantageously combine the precision of computer controlled equipment with the fidelity of a laser in performing the functions and operations herein described.

Particularly, and as shown in FIG. 1, the system 10 comprises: a tool 24 operable to perform at least one action of work; positioning means 25 for positioning the tool 24 relative to the biological tissue 12 and a directed laser light beam 30 to perform the at least one action of work required as part of a surgical procedure; computing means which in this embodiment comprises a controller 100 and storage 18 storing electronic program instructions for controlling the controller 100, and information and/or data; a display 20 for displaying a user interface 21 and input means 22 for the surgeon 16 to interact with the system 100; and hardware components stored in a base unit 27 that connect to the tool via a conduit 26.

The position means 25 may comprise any component, or assembly of components, operable to move the tool 24 and/or the biological tissue 12 relative to one another so that the tool 24 can perform the at least one action of work on the biological tissue 12

In the preferred embodiment, the tool 24 comprises an end effector 28 that is operably attached at the working end of a robot arm 105 comprising the positioning means 25. The end effector 28 is a hardware assembly comprising several components and sensors, as described in further detail herein, to form and direct a laser beam 30 operable to perform the actions required to be done on the biological tissue 12 during a surgical procedure and sense the results. These actions include surgical ablation (removal of matter).

The robot arm 105 comprises a manipulator 23 and a robot arm controller 106 which is specifically designed to operate and control the manipulator 23. In the embodiment, the robot arm 105 advantageously allows the end effector 28 to be optimally positioned and held stable relative to the biological tissue 12 by the system 10 for the at least one action of work to be performed correctly. The robot arm 105 is securely mounted to a base unit 27 providing a stable platform sufficient for the range of motion required during the operation of the system 10. The robot arm 105 has at least 5 degrees of freedom and contains safety features that allow for it to be used in close proximity to people by sensing resistance to movement. The robot arm controller 106 connects to the controller 100 which is operable to guide and monitor its activity.

Controller 100 is operable, under control of the electronic program instructions from storage 18, to receive input via the input means 22, combining and interpreting input comprising safety, localisation, surgical planning and sensor data in real time, and to utilize and control sensing for precision control, safety and localization, representations of the biological tissue 12 and work to be done, via machine perception and other means, process the input and, on the basis of the processing, control the positioning means 25 and the tool 24 to work the biological tissue 12 under the supervision of the surgeon 16. The biological tissue 12 is worked by the tool 24 performing the at least one action of work thereon. In the embodiment, controller 100 comprises a computer system that communicates and controls the components of the system.

In the embodiment, the components of the system 10 required for the functioning of the tool 24 predominantly reside in a housing comprising a base unit 27. The aforementioned components, comprising laser related components, particle filtration related components, water spray components, controller 100, sensor controllers 103, dynamic focusing optics controller 137, storage 18, hardware failsafe watch dog 175, control systems, and power related components of the system 10, will be discussed in further detail hereafter.

System 10 uses a positioning sensor 170, which may also be referred to as a computer assisted surgery (CAS) navigation sensor, to track in three-dimensions the location and movement of the biological tissue 12 being worked on. The positioning sensor 170 is operatively positioned high up at an elevated location, either attached to a roof, wall, arm, or stand, with a clear field of view to the biological tissue 12 and surrounds. Several existing systems are commercially available and used in current surgical techniques. The typical process for a computer navigated TKR is to insert pins into the femur and tibia bones and attach a fiducial marker 70—reflective arrays of markers that can be recognised and oriented by a positioning sensor 170. The fiducial marker 70 position data is streamed to the controller 100 by the positioning controller 171 to assist in correctly positioning and aligning the resections. This input data is the primary method of the system 10 for understanding the location and movement intraoperatively of the biological tissue 12 being worked on. Fiducial markers 70 are also attached to surgical tools used in the procedure as the current gold standard method to position the resections in the correct place with the right alignment.

System 10 can also use the laser to indelibly mark one or more visually trackable patterns on the biological tissue creating a lasered (i.e. formed by the laser e.g. laser inscribed) fiducial mark 71. A sufficiently high speed (for example operating at greater than about 60 Hz) optical imaging sensor can provide high-resolution imaging that the system 10 can use to detect movement of a mark by comparison against prior images, especially laterally from the point of view of the tool where the most risk lies for errors in targeting the biological tissue 12 for ablation. A lasered fiducial mark 71 can supplement the tracking provided by the aforementioned fiducial marker 70.

The input to system 10 is appropriate to biological tissue 12 to be worked and the work to be performed. In the embodiment, the input comprises details of and/or associated with one or more of biological tissue 12, patient 14, the orthopaedic surgical procedure, one or more components of system 10, and the surrounding environment. The details comprise pertinent data and/or information.

The data and/or information may be obtained by one more of retrieving, receiving, extracting, sensing, and identifying it, from one or more sources. The one or more sources of data and/or information may be part of system 10, reside on a component of system 10 such as storage 18, and/or be or reside elsewhere, remote from system 10.

The data and/or information comprises: experimental and historic data; pre-operative data, including pertinent medical imaging of biological tissue 12 and the patient 14 and clinical/surgical plans for the patient 14; and data obtained via intraoperative sensing during the procedure (discussed further below). The data and/or information may comprise joint kinematics data generated via gait analysis using at least one inertial measurement unit (IMU). An IMU is an electronic device operable to measure and report on a body's specific force, angular rate, and sometimes the magnetic field surrounding the body, using a combination of accelerometers and gyroscopes, sometimes also magnetometers. In embodiments of the invention, data and/or information may also be generated by and/or obtained from devices, including, for example, activity trackers (such as those provided under the trade mark FITBIT™), smart braces, and smart splints.

In the embodiment of the invention, the display 20 for displaying the user interface 21 and the user input means 22 are integrated in a touchscreen. In alternative embodiments, these components may be provided as discrete elements or items.

A touchscreen display 20 is operable to sense or detect the presence and location of a touch within a display area of the system 10. Input commands to system 10 in the form of sensed "touchings" of the touchscreen display 20 are inputted to the system 10 as commands or instructions and communicated to the controller 100. It should be appreciated that the user input means 22 is not limited to comprising a touchscreen, and in alternative embodiments of the invention any appropriate device, system or machine for receiving input, commands or instructions and providing for controlled interaction may be used, including, for example, a keypad or keyboard, a pointing device, or composite device, and systems comprising voice activation, voice and/or thought control, and/or holographic/projected imaging.

Typically, the user is a person suitably qualified and experienced to use the system 10 to perform the work on the biological tissue 12, such as an orthopaedic surgeon 16 in the embodiment. The user is a trained medical professional who supervises and directs the system 10 via the touchscreen display 20 of the user interface 21.

The display 20 and user interface 21 are positioned in a convenient location close to the surgeon 16 to maintain good visibility and easy interaction.

Figure 2A:
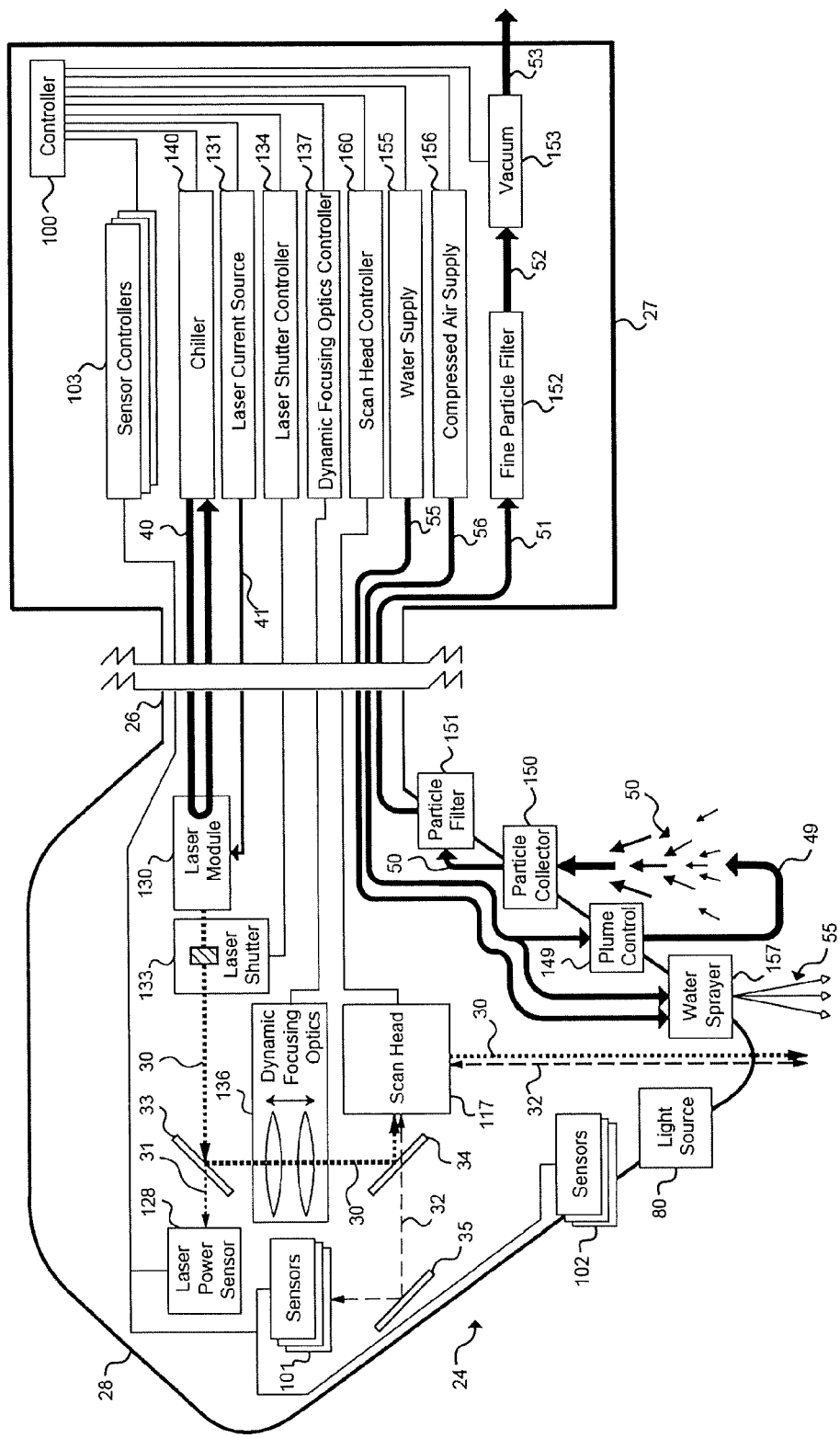
FIG. 2A depicts a particular embodiment of an end effector of the system of FIG. 1.

FIG. 2A of the drawings depicts the preferred embodiment of the tool 24 as an end effector 28 comprising various components and connections to other components in the base unit 27 via the conduit 26.

A laser module 130 is operable to emit a coherent light beam 30 at a predefined wavelength suitable for the ablation of biological tissue 12.

A laser current source 131 is operable to supply the laser module 130 with electrical current required to generate the light beam 30. The controller 100 is operable to select different parameters in the laser current source 131 to modify the resulting light beam 30 that is generated.

Cooling means in the form of a chiller 140 is operable to cool the laser module 130 via circulating coolant 40 to prevent it from overheating along with other components of the system 10, including scan head 117 and water 55, as discussed in further detail hereafter A laser shutter 133 is operable to protect against the accidental emission of light from the laser module 130 using a switchable physical barrier that blocks the light beam 30.

A laser shutter controller 134 is operable to control the functioning of the laser shutter 133 as directed by the controller 100.

Dynamic focusing optics 136 are operable to dynamically change the focal length and focus beam diameter of the light beam 30 at the target distance determined as desirable by the controller 100 via the dynamic focusing optics controller 137.

Mirror 33 is operable to reflect the light beam 30 at an alignment for the correct functioning of the dynamic focusing optics 136. The mounted position of mirror 34 is adjustable to ensure the alignment that can be calibrated depending on the position of the laser module 130 and correct path into the dynamic focusing optics 136. In the preferred embodiment, mirror 33 is partially reflective such that it is operable to beam split a very small predetermined ratio of transmitted beam 31 to a laser power sensor 128 that is operable to sense the power output of the laser module 130. The controller 100 can calculate the total power output of the laser module 130 by compensating for the known ratio of sensed transmitted energy. In another embodiment where it is not necessary to dynamically sense the laser energy the mirror 33 can be fully reflective.

Mirror 34 is a dichroic filter that is operable to reflect light in the wavelength band of the light beam 30 into the beam entrance of a scan head 117 and transmit light outside that wavelength band along the light path 32. The mounted position of mirror 34 is adjustable to allow the reflective alignment to be calibrated depending on the path of light beam 30 through the dynamic focusing optics 136 and the correct path into the scan head 117.

The precision of a current state-of-the-art robot arm 105 is not sufficient to be the only method of directing the laser beam 30 from the end effector 28 to the biological tissue 12 for ablation. A means of fine motion is operable to allow for a secondary method of directional targeting of the laser beam 30 at micron-scale accuracy.

In the preferred embodiment, a scan head 117, typically comprising two galvanometer scanner aligned mirrors (not shown), is used as the fine motion means to rapidly retarget the laser as directed by a scan head controller 160 operating as fine motion controller 111 of FIG. 1. A scan head 117 typically has an f-theta lens that corrects the focus distance across a flat target plane, however as our target will be a freeform shape the embodiment does not need an f-theta lens and uses dynamic focusing optics 136 instead. Other embodiments with different fine motion means, such as rotating polygonal mirrors, tip/tilt mirrors, or Stewart platforms, will be discussed in further detail hereafter.

Mirror 35 is operable to reflect the light path 32 to the set of sensors 101 in direct line-of-sight with the path of laser beam 30. The mounted position of mirror 35 is adjustable to allow the reflective alignment to be calibrated with the path of light beam 30 and the set of sensors 101.

The set of sensors 101 comprise a plurality of components requiring sensing and/or emitting light along the same path as the laser beam 30 to the target of ablation on the biological tissue. The set of sensors 102 comprises a plurality of components positioned on the surface of the end effector 28 operable to sense and/or interact with the biological tissue or environment from its own vantage point. For intraoperative safety, localisation and precision shaping there is a requirement to noninvasively identify the biological tissue 12 prior to laser shaping. The sensors will be discussed in further detail hereafter.

A light source 80 is operable to provide illumination such that the set of sensors 101/102 can correctly and optimally sense the biological tissue 12 and environment. For various sensors, such as a hyperspectral imaging sensor 180 which will be discussed in further detail hereafter, this illumination will be operable across the range of wavelengths and modalities being sensed.

Lasers suitable for surgical ablation generate a light beam 30 at a wavelength that is strongly absorbed by water, a common and abundant component of the biological tissue 12. Water has a strong absorption peak at a wavelength of about 3 μm. Example laser sources which operate in this particular wavelength range and are particularly suited to laser ablation procedures such as disclosed herein include Er:YAG solid state laser systems having an emission wavelength of about 2940 nm. The instantaneous heating of the water is the process by which material is ablated from the surface of the biological tissue 12. If there is not enough water to efficiently absorb the energy of the laser light beam 30 then the ablating effect is reduced, and the biological tissue 12 is in danger of merely carbonising. If there is too much water too much energy is wasted merely flash boiling water and again the ablating effect is reduced, however there is little danger of carbonising the biological tissue 12. Given these two extreme cases, there exists an optimal amount of water whereby the most biological tissue 12 is ablated without carbonising for the least amount of energy used in the light beam 30.

Where there is too much water on the biological tissue 12 there is no direct way for the system 10 of the embodiment to reduce it other than expend additional energy with the light beam 30 vaporising it. An indirect way would be to rely on the surgical team to use suction near the target point to remove some water.

It is easier to introduce additional water to the biological tissue 12 than to remove it. In the preferred embodiment, this comprises a water supply 155 of a suitable sterile state provided via a consumable container or piped supply, and operable to provide water 55 for spraying onto the surface of the biological tissue 12 to be ablated.

In preferred embodiments, the sprayer liquid comprises a solution such as, for example, water or a water-derived solution or similar as would be appreciated by the skilled addressee. Suitable solutions would preferably have a strong absorption of light at the wavelength of the laser beam generated by laser module 130 so as to effect instantaneous heating of the sprayer liquid which assists the ablation process making it more efficient, whilst simultaneously acting as a coolant for the biological tissue 12 to protect the biological tissue 12 against carbonisation.

Directing means in the form of the water sprayer 157 is operable to irrigate the biological tissue 12. This advantageously allows for more efficient ablation and assists in protecting the biological tissue 12 against carbonisation. In alternative embodiments of the invention, liquids other than, or additional to, water may be used.

Compressed air supply 156 is operable to propel the water 55 through the water sprayer 157. In the preferred embodiment, this comprises a compressor taking sterile air from the surgical environment which is then compressed and the compressed air 56 is channelled to the water sprayer 157. In alternative embodiments of the invention, containers or a piped supply may be used as the compressed air supply 156.

The ablation of biological tissue 12 results in a plume 50 of vaporised and fragmented material ejected from the surface. The plume comprises particulates of submillimetre-scale and submicron-scale. Some microscopic particulates pose a health hazard to the operating staff about the system 10 and the patient 14, as inhaling the particles can be damaging to the respiratory system. A preferred solution to this problem is for the system 10 to comprise extraction means to capture and filter the plume 50.

In the preferred embodiment, the extraction means comprise a particle collector 150, a particle filter 151, a fine particle filter 152 and a vacuum 153 operable to capture the plume and extract the particulates via filtration.

A particle collector 150 is comprised of a plurality of openings operatively positioned close to where the ablation plume 50 is ejected to ensure that it collects the majority or all the particulates. The plume 50 is initially passed through a particle filter 151 that progressively filters smaller particles—given the volume of ablation material it is important not to fill a single high efficiency (fine) filter. The filtered air 51, substantially reduced in volume of particulates, is channelled to a fine particle filter 152 that will filter and retain the remaining finer particulates not captured by the particle filter 151. A vacuum 153 provides the pressure to draw the air into the filtration system and expel the cleaned air 53 from the fine particle filter is channelled to the environment.

In the preferred embodiment, the particle filter 151 retains the majority of the particulates in the plume 50 and is a consumable filter shield 43, discussed in more detail herein, which can be replaced for each operation. The fine particle filter 152 comprises a high efficiency particulate air (HEPA) filter.

Figure 2B:
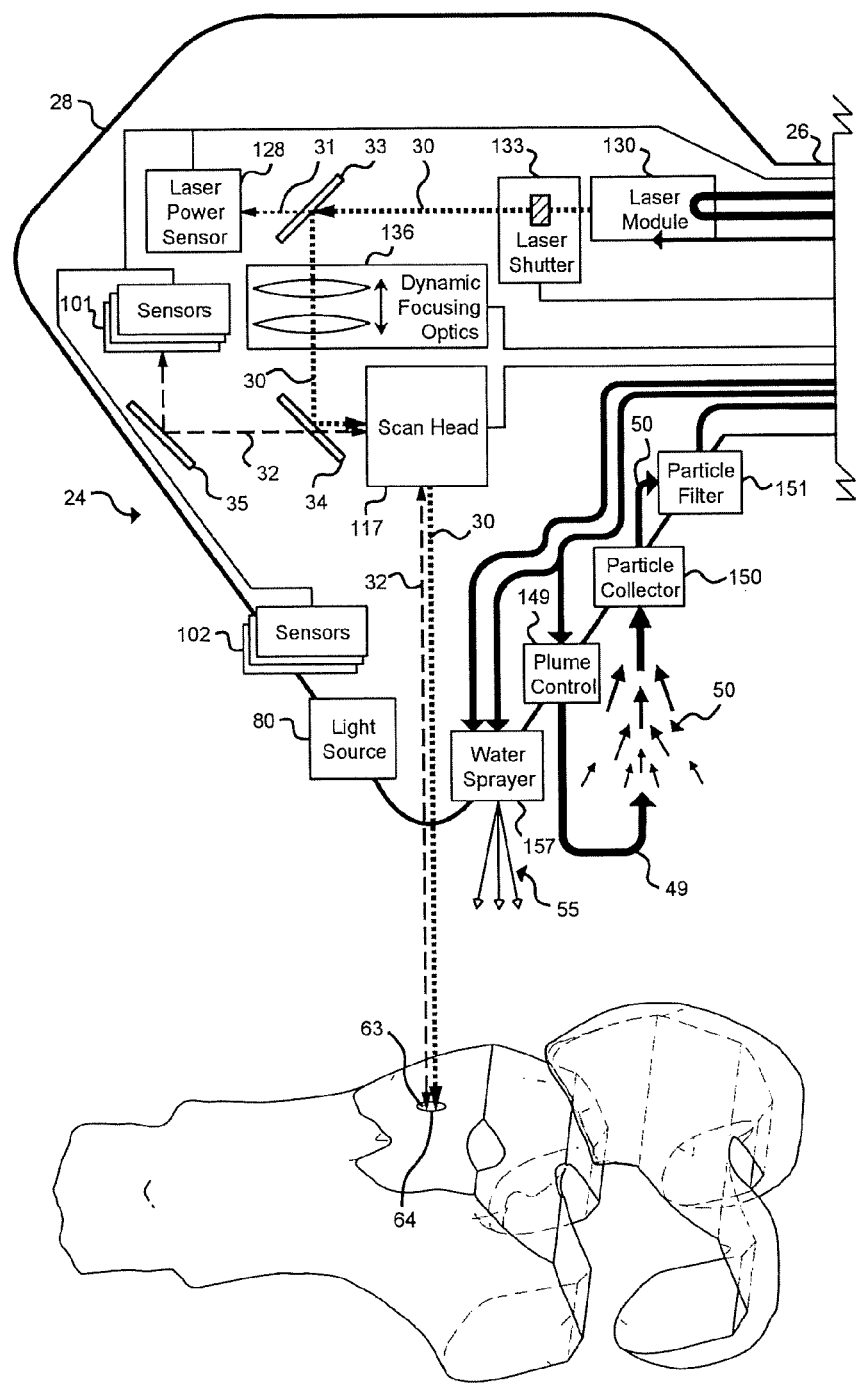
FIG. 2B depicts an example usage configuration of the end effector of the system of FIG. 1 for shaping bone tissue of a patient during a surgical procedure.

FIG. 2B depicts an example usage configuration of the end effector 28 of the system 10 of FIG. 1 or FIG. 2A for restructuring of bone tissue of a patient during a surgical procedure. Laser beam 30 from laser module 130 impacts the biological material (e.g. bone) 12 with a spot size 64 defining the interaction region 63. Typical spot sizes for operation of the systems and methods disclosed herein range between about 300 and about 1000 μm to give the requisite laser beam fluence in the interaction region 63 necessary for efficient operation of the system 10 for laser ablation processes of biological tissue 12 such as, for example bone.

Figure 3:
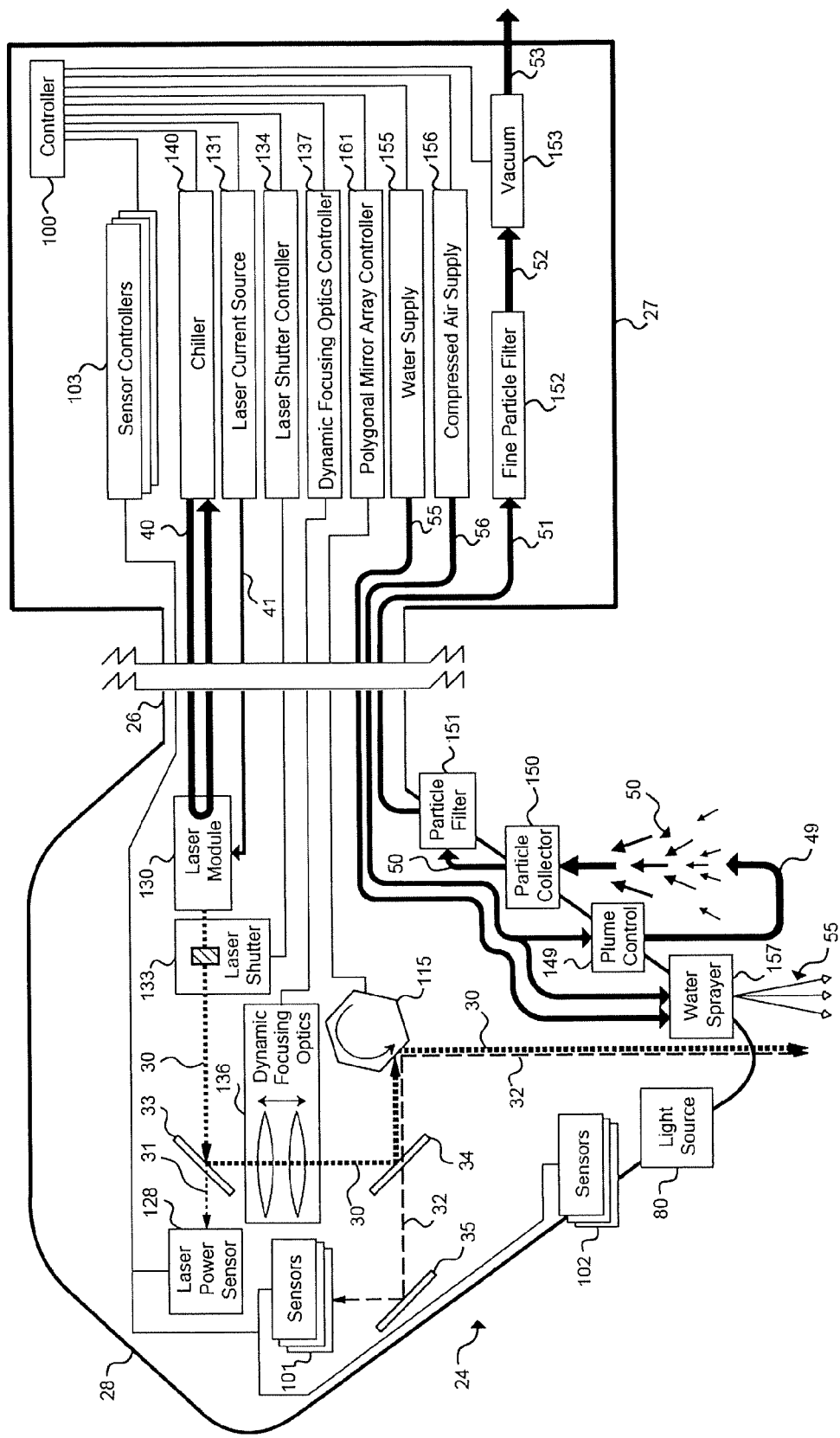
FIGS. 3, 4 and 5 depict alternative embodiments of an end effector of the system of FIG. 1.

FIG. 3 of the drawings depicts an embodiment of the tool 24 as an end effector 28 of the system 10 utilising the alternative fine motion means of a rotating polygonal mirror array 115 as directed by a polygonal mirror array controller 161 operating as fine motion controller 111 of FIG. 1.

The polygonal mirror array 115 is a set of mirrors arranged at incrementing angles around a polygon that that is rotated at a precisely constant speed.

The angles of the mirrors mean that the light path 32 sweeps in several lines with a stride distance between them (looking somewhat similar to a square barcode with lines of equal width and distance between them). Eventually, upon a complete revolution of the array, the light path 32 returns to the start of the first line and the pattern repeats.

The controller 100 times the light beam 30 pulses to coincide when the polygonal mirror array 115 is targeting a surface location requiring ablation.

The advantage of this method of fine motion is that the rotating polygonal mirror array 115 is simple and requires less expensive components.

The disadvantages of this method is that the controller 100 needs to wait until the polygonal mirror array 115 rotates into the position for the required targeting and there is a set pattern of ablation, which may be inconvenient for ideal ablation in the minimum time required.

Figure 4:
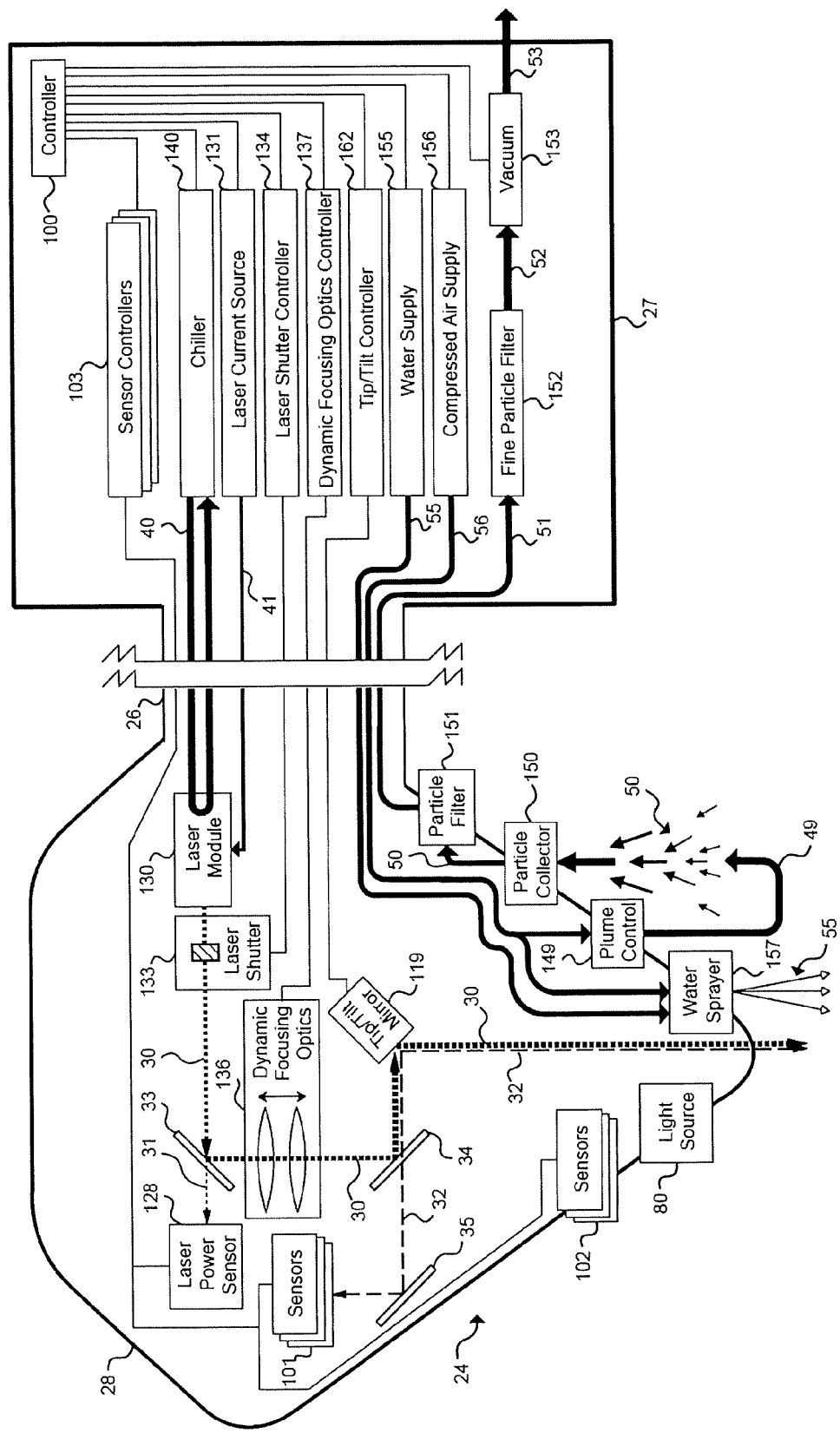

FIG. 4 of the drawings depicts an embodiment of the tool 24 as an end effector 28 of the system 10 utilising the alternative fine motion means of a tip/tilt mirror 119 as directed by a tip/tilt controller 162 operating as fine motion controller 111 of FIG. 1.

The tip/tilt mirror 119 is a small device with a piezo controlled mirror at an end thereof. The tip/tilt mirror 119 can be angled in the X/Y axis.

This is similar to the scan head 117 but potentially faster, with the downside of having a lower targeting angular range.

In an embodiment of the invention using tip/tilt mirror 119, the tip/tilt mirror 119 is aligned at 45° to the light beam 30 such as that when the tip/tilt mirror 119 is in the 'neutral' position the light beam 30 is reflected directly down (at 90° to the incident light path). In this way the tip/tilt mirror 119 can redirect the laser beam 30 in a cone shaped targeting range.

A primary advantage of such a technique is near instantaneous and precise targeting of the light beam 30. A fast moving tip/tilt mirror 119 means that the system 10 can reposition the laser beam 30 and pulse the laser faster causing a greater volume of biological tissue 12 to be ablated.

A disadvantage may be that the range of the targeting cone is less than that using the laser scan head 117. It would be advantageous to place the tip/tilt mirror 119 as close to the top of the end effector 28 as possible to maximise the targeting angle, but that may also result in shielding that opens outwards, lessening the effect of protecting against objects getting in the way of the laser beam 30.

Advantages arising from use of the tip/tilt mirror 119 include: small inertial mass (almost no influence of acceleration); fast movement of laser beam 30; and ease of implementation.

Figure 5:
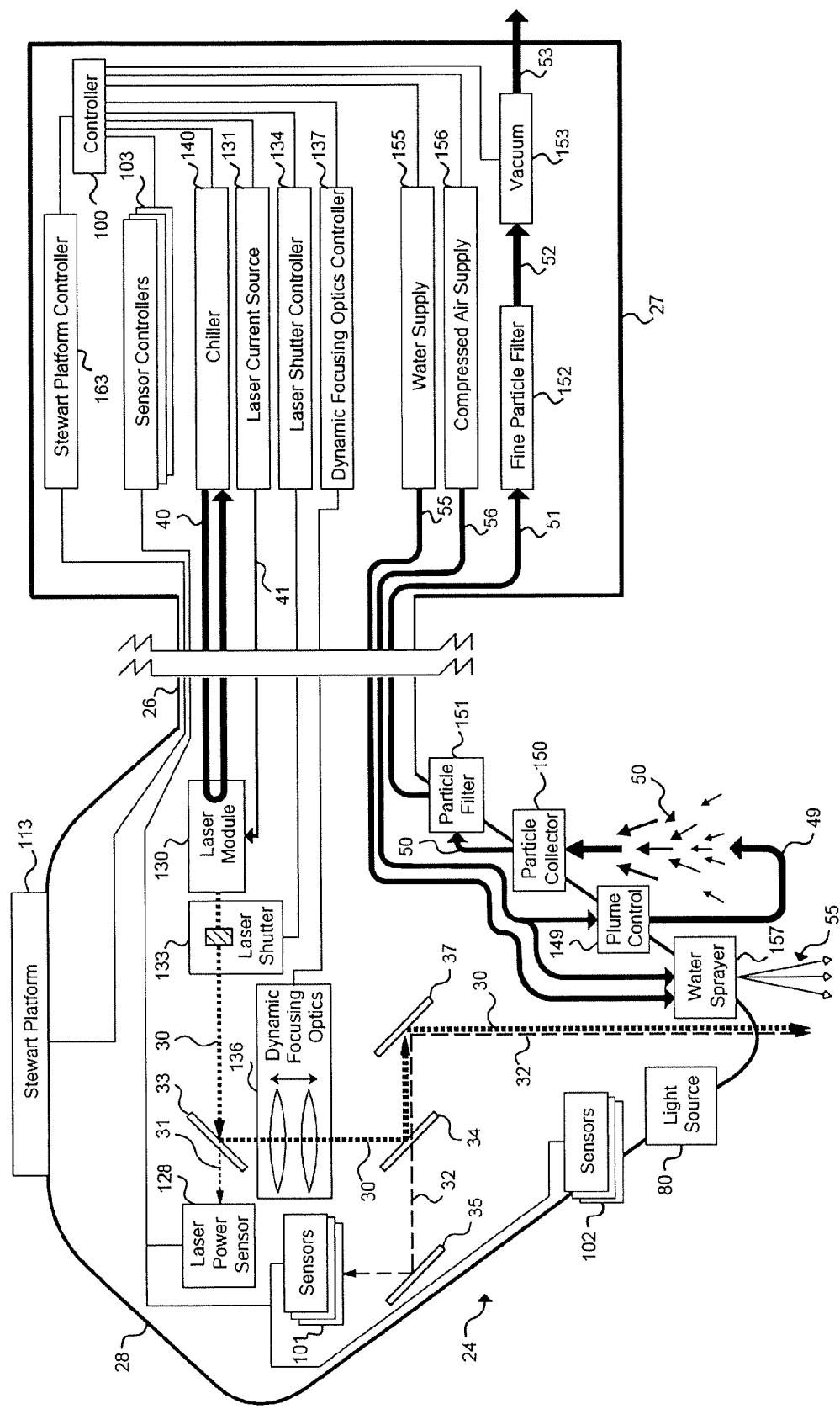

FIG. 5 of the drawings depicts an embodiment of the tool 24 as an end effector 28 of the system 10 utilising the alternative fine motion means of an actuator in the form of a Stewart platform 113, which may also be referred to as a "hexapod", as directed by a Stewart platform controller 163 operating as fine motion controller 111 of FIG. 1.

The Stewart platform 113 is a type of parallel robot that has six prismatic actuators, which may be, for example, hydraulic jacks or electric actuators, attached in pairs to three positions on a baseplate of the Stewart platform 113, crossing over to three mounting points on a top plate of the Stewart platform 113. Items, such as devices, placed on the top plate can be moved in the six degrees of freedom in which it is possible for a freely-suspended body to move. These are the three linear movements x, y, and z (lateral, longitudinal, and vertical), and the three rotations pitch, roll, and yaw.

Using a Stewart platform 113 is a solution that allows for very precise XY linear movement with the benefit of Z linear movement to maintain a set distance from the target surface contours if required. Depending on the solution it also allows for angling of the laser beam 30 as well as linear movement. Given enough weight bearing capacity it is also possible to allow for other components and covers to be also mounted directly.

Advantages provided by use of Stewart platform 113 include: a wide range of movement; 3D movement (maintaining focus); and all tools (water sprayer 157, plume collector 150, laser module 130, sensors of the set of sensors 101 and 102) maintain the same movement.

There may be disadvantages arising from the use of a Stewart platform 113 such as: inertial mass; acceleration and deceleration (complicated laser control); complicated implementation in the overall system (minimum 12 DOF); and obscuring of other sensors on the end effector 28.

The principal disadvantage of inertial mass has a significant effect on the amount of time it takes to direct the laser beam 30 at the next target location on the biological tissue 12. A scan head 117 or tip/tilt mirror 119 can individually target at least 400 laser pulses per second across any geometry, which a Stewart platform 113 cannot match.

The mass of the end effector means that even a moderate weight of several kilograms will likely cause issues with momentum. Moving the platform to micron-scale accuracy may cause it to "overshoot" as it may not be able to accurately stop the movement in time, or the opposite problem of backlash. Some of these problems can be mitigated by getting the end effector 28 up to speed prior to ablating to keep it going at a set speed and firing the laser beam 30 in a timed manner (as with a pendulum, for example).

It should be appreciated that alternative laser power transmission to the end effector 28 is possible. In an alternative embodiment of the invention depicted in FIG. 6 of the drawings, rather than mounting the laser module 130 in the end effector 28, it is possible to have the light beam 30 transmitted to the end effector 28 via a fibre optic 36 with fibre coupling optics 138 from the laser module 130 mounted within the base unit 27. The use of fibre optic 36 is to be considered as merely the preferred embodiment of the standard methods of transmitting laser energy, including, but not limited to, a wave guide or articulated arm.

Figure 6:
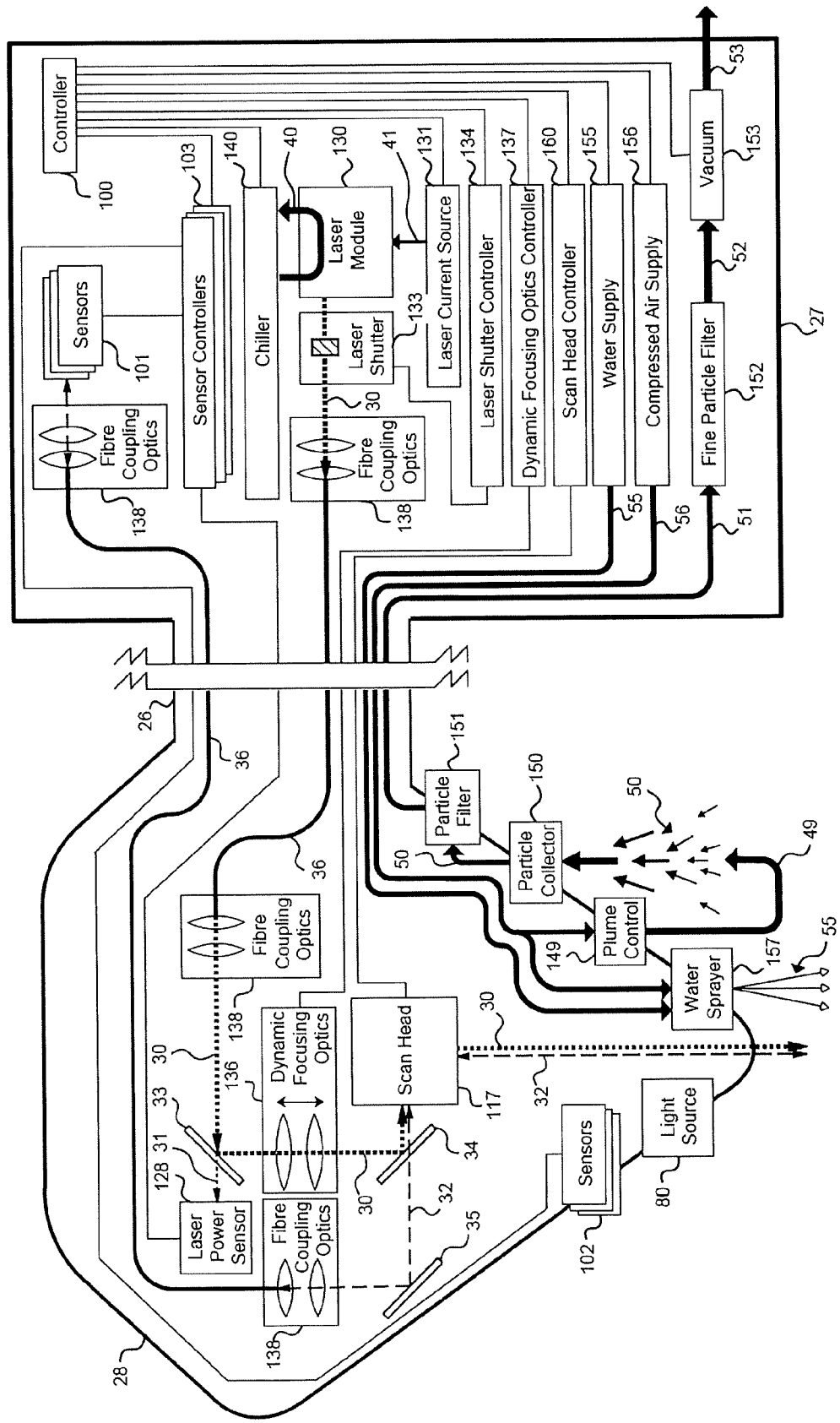
FIG. 6 depicts an alternative embodiment of laser transmission to an end effector of the system of FIG. 1.

Similarly, in the alternative embodiment of the invention depicted in FIG. 6 of the drawings, the set of sensors 101 can be housed in the base unit 27 and the light path 32 is transmitted from the end effector 28 via a fibre optic 36.

An advantage of this alternative method includes that less space is required, and weight is reduced, in the end effector 28. Depending on the components that need to be incorporated into the end effector 28 it may be that the physical space isn't available or that the required alignment with the dynamic focusing optics 136 isn't practical. In such an embodiment, rather than wide cabling required for carrying power and water from the base unit 27, all that is required is a single thin optical fibre 68.

Such an advantage may be minimal in embodiments where other cabling is required, for suction and sterile air/water for example.

It should be kept in mind that there may be more complex coupling optics required to channel the laser light beam 30 into the fibre optic 36 and decouple the laser light beam 30 back out of the fibre optic 68 at the end effector 28. There may also be a substantial laser power loss by coupling through the optical fibre. Generally speaking, fibre optic 68 itself may have a 25% power loss and the coupling/decoupling optics required may contribute a further 23% loss. These factors mean that a more powerful laser current source 131 is required which in turn has a greater cost and running electrical power requirement. Furthermore, generally speaking, an optical fibre is fragile and will break if bent too far or knocked with enough shock force.

Figure 7:
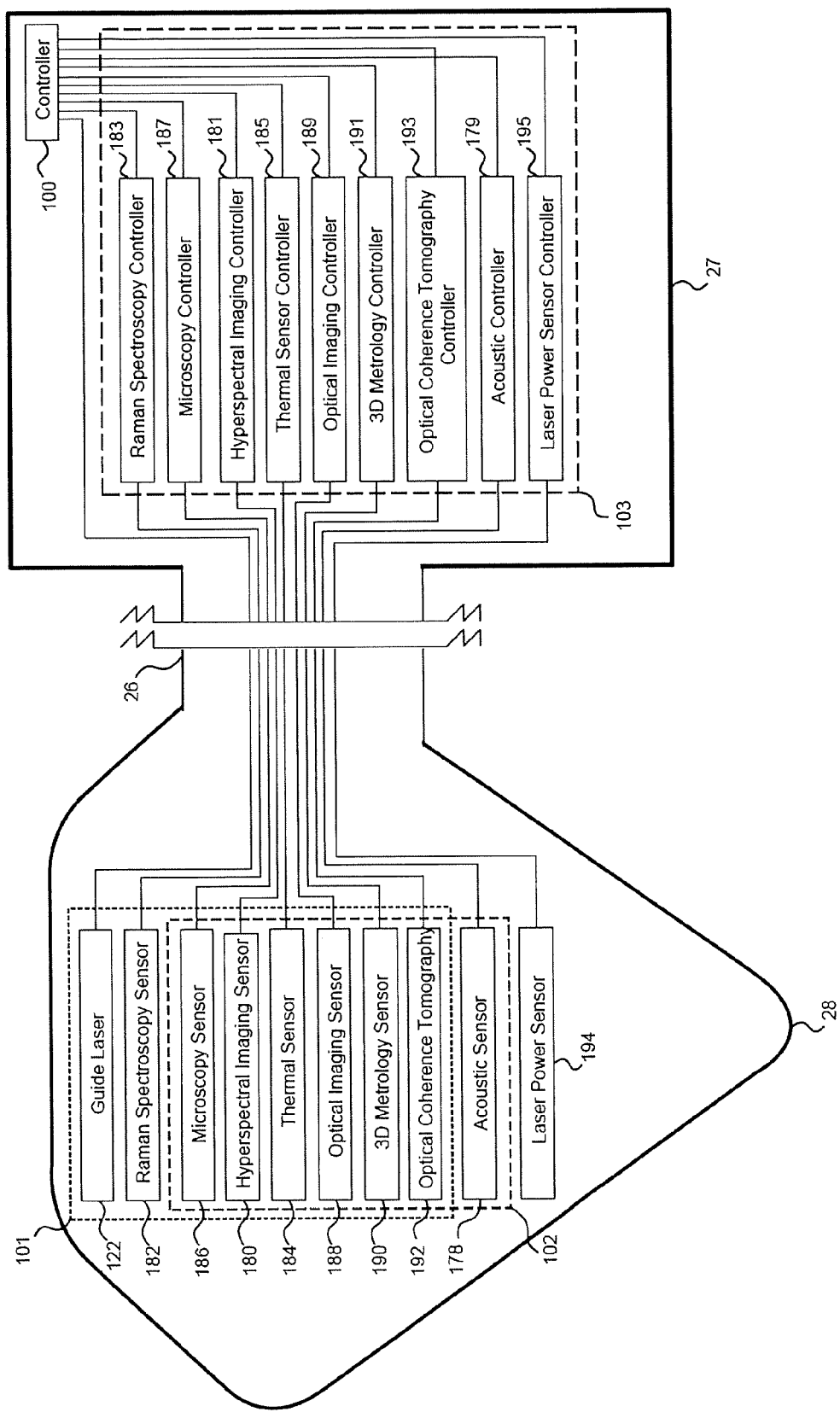
FIG. 7 depicts an embodiment of the sensors and sensor controllers of an end effector of the system of FIG. 1.

FIG. 7 of the drawings depicts an embodiment of the set of sensors 101 and the set of sensors 102 in the end effector 28 with connections to associated controllers in the set of sensor controllers 103 in the base unit 27 via the conduit 26. It should be noted that in some embodiments a sensor may be in the set of sensors 101 operatively positioned to sense the light in the line-of-sight light path 32 and/or sense the biological tissue from another vantage point as part of the set of sensors 102.

Individual sensors, in the process of providing input to and being directed by the controller 100, are operable to monitor, sense and gather or measure sensor data and/or information associated with or relating to one or more characteristics, properties and/or parameters of the system 10, the biological tissue 12, the patient 14, the surrounding environment, components, systems or devices associated therewith or coupled thereto.

A guide laser 122 allows the system 10 to provide visual feedback to observers, such as the surgeon 16 and members of the surgical team, of proposed ablation target areas on the biological tissue 12. This advantageously increases user confidence in the system 10 by clearly providing visual feedback on the biological tissue 12 rather than just through the display 20. Without the guide laser 122 it may sometimes be unclear exactly where the system 10 is planning to ablate, or is currently ablating, as the ablation laser beam 30 is not visible to the naked eye in the embodiment. The guide laser 122 is operated by the controller 100. The guide laser is a visible light laser, and in the preferred embodiment the guide laser is a red laser.

A Raman spectroscopy sensor 182 is operable to observe vibrational, rotational, and other low frequency modes in the biological tissue 12 as directed by the controller 100 via the Raman spectroscopy controller 183.

Raman spectroscopy relies on inelastic scattering of monochromatic light, usually from a laser source, and is operable to provide additional information from a single point on the biological tissue 12. The system 10 is operable to use Raman spectroscopy for material identification in surgical procedures. In addition to acting as a guide, the above-mentioned guide laser 122 beam can serve the secondary purpose of acting as a red laser light source for Raman spectroscopy. In a Raman scattering process a small fraction of a red laser beam's photons are inelastically scattered, that is they lose energy to the molecules that make up the target sample. The amount of energy lost per photon is related to the vibrational energy of the molecule. So, for example, bone contains hydroxyapatite ($Ca_5(PO_4)_3(OH)$) and the PO bond has a characteristic Raman line at 959 cm-1. The presence of this line in the Raman scattered light indicates that the guide laser 122 is on bone. Depending on the work action to be performed and analysis and control decisions made (discussed in further detail below), if bone is the target and other conditions are satisfied, then the controller 100 is operable to activate the laser beam 30 and ablate the biological tissue 12. Also, other joint tissues, such as cartilage and ligament, have characteristic Raman spectra that similarly allow them to be identified.

A microscopy sensor 186 is operable to provide a detailed magnified visual image of the biological tissue 12 as directed by the controller 100 via the microscopy controller 187. The system 10 is operable to use information gathered by the microscopy sensor 186 to assist in the detection of biological tissue 12 composition via visual comparison to known samples. The detailed resolution imagery generated can also be provided to the surgical team to provide a better viewpoint of the target which may be impossible to see from a vertical orientation given the necessity of the positioning of the end effector 28.

A hyperspectral imaging sensor 180 is operable to detect the intensity and frequency of reflected, or absorbed, light across a wide spectrum (beyond visual range) as directed by the controller 100 via the hyperspectral imaging controller 181. By illuminating the target with a light source 80 that covers the spectral range of the hyperspectral imaging sensor 180 samples can be taken of the reflected light. In the preferred embodiment, the spectral range from 400 nm to 1000 nm is used.

The varying intensities contain a signature that is used by the system 10 to predict the type and composition of biological tissue 12. This prediction can be carried out with machine learning, as will be described in further detail.

The hyperspectral data can be used with machine learning to identify the types, properties and composition of biological tissue 12.

A thermal sensor 184 is operable to detect radiation in the mid to long-infrared range of the electromagnetic spectrum to map out the temperature of the biological tissue 12 as directed by the controller 100 via the thermal sensor controller 185. During and after laser shaping the system 10 is operable to noninvasively assess the thermal impact and the results can be used to optimise the laser parameter selection in subsequent ablation runs.

An optical imaging sensor 188 is operable to provide a visual image of the biological tissue 12. The images can be analysed to assist in the prediction of the type and composition of biological tissue 12. It can also be used at high speed to track objects in the field of view as directed by the controller 100 via the optical imaging controller 189. The aforementioned lasered fiducial mark 71 can also be tracked with an optical imaging sensor.

A 3D metrology sensor 190 is operable to detect the geometry of the surface of the biological tissue 12 as directed by the controller 100 via a 3D metrology controller 191. Information gathered by which is used by the system 10 to determine the geometry of a surface without contact. The geometry of the surface of the biological tissue 12 is very important for the system 10 to be able to determine the shape prior to and after ablation.

There are several different types of technology to sense a 3D geometry, including time-of-flight, laser triangulation, structured light projection and modulated light. In order to achieve the required micron-scale resolution, the system 10 uses structured light projection technology, line profile sensor or a point profile sensor, such as a chromatic confocal sensor. In an embodiment, a structured light scanner projects patterns of light on the subject and two offset cameras look at the deformation across the surface—a process that takes fractions of a second and can scan a relatively large area quickly. In the preferred embodiment, a chromatic confocal sensor is part of the set of sensors 101 and takes readings as the fine motion means traverses the light beam 30 across the surface, building up a complete geometry over time.

Optical coherence tomography (OCT) sensor 192 is operable to capture micron-scale resolution, three-dimensional images of the biological tissue 12 as directed by the controller 100 via an optical coherence tomography controller 193. OCT uses light to capture micrometre-resolution, three-dimensional images based on low-coherence interferometry. This allows it to penetrate scattering media such as biological tissue up to about 1000 to 2000 μm below the surface of the biological tissue 12 to obtain data of the underlying structure of the tissue to be ablated. The system uses data obtained from OCT sensor 192 as a mechanism to detect the surface and underlying tissue composition for planning the ablation process for maximum ablation efficiency with minimal thermal affect to the surrounding tissue capable of causing thermal-induced damage to the surrounding tissue.

While an ablation is taking place the system 10 will not be able to sense the environment in the same microsecond timeframe and there is a risk that the material targeted is different than expected, or a foreign object is introduced into the light beam 30. One possible way to mitigate this risk, and utilized in the embodiment, is the use of an acoustic sensor 178 which is operable to measure the pressure waves from the environment and around the biological tissue 12. With reference to method 2800 of FIG. 28, the distinct pressure waves that a laser light beam 30 makes ablating material, such as biological tissue 12, can be measured and, via analysis of the data measured, the system 10 is operable via the acoustic controller 179 to determine in real-time if an unexpected material has been hit. Hard biological tissue sounds different to soft biological tissue, and any other types of material. By examining (preferably constantly) the sound of the previous pulse's ablation it is possible to halt operation of the system 10 if any sound is encountered that disagrees with the expected sound of the material type that was the target of the ablation. This safety feature may not prevent the first laser pulse from hitting an unexpected material, but it can prevent subsequent laser pulses that would have otherwise occurred prior to any overall re-sensing.

The sensing techniques above are used in the implementation of the invention to identify and monitor the biological tissue 12 and operate in conjunction with the shaping laser to deliver a safe, highly accurate and precise system 10 under intelligent control.

Figure 8:
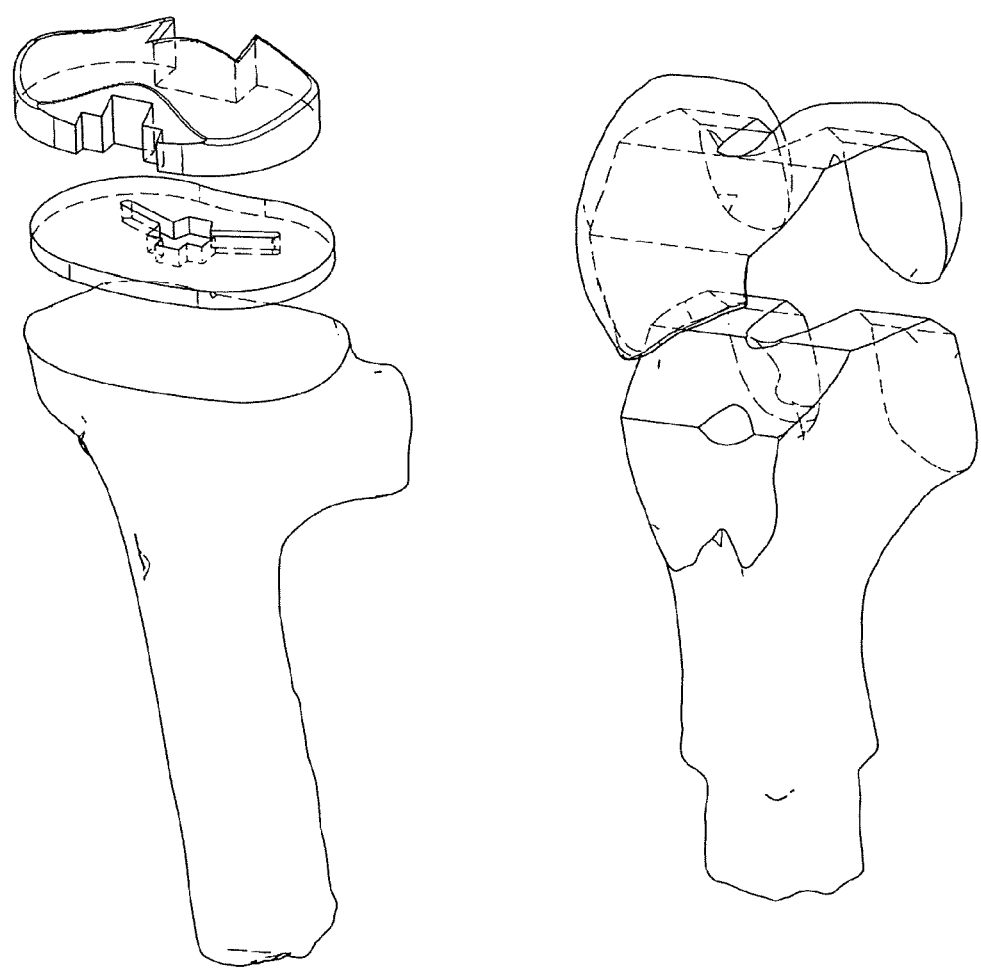
FIG. 8 depicts resections of the bones for implants of a total knee replacement surgical operation.

As will be described in further detail, the system 10 is operable to perform subtractive laser ablation that takes into account one or more relevant factors including thermal effect (that is to say, biological quality of residual tissue— non localized), biological make up of bone being ablated, flatness of residual surface, planar alignment and relationship to mechanical axis (global alignment). The laser light beam 30 may also ablate defined channels or holes, or other shapes or shaping as may be appropriate, into the bone that will allow for/accommodate an implant/prosthesis or one or more portions or components 13 thereof, as depicted in FIG. 8 of the drawings showing the matching resections 60 of the joint ends of a tibia bone and a femur bone.

In addition to bone, the laser light beam 30 is also operable to cut all human tissue, including skin, muscle, fat, meniscus, tendons, connective tissue, articular cartilage, capsule, ligament, and fascia of the patient 14.

Figure 9:
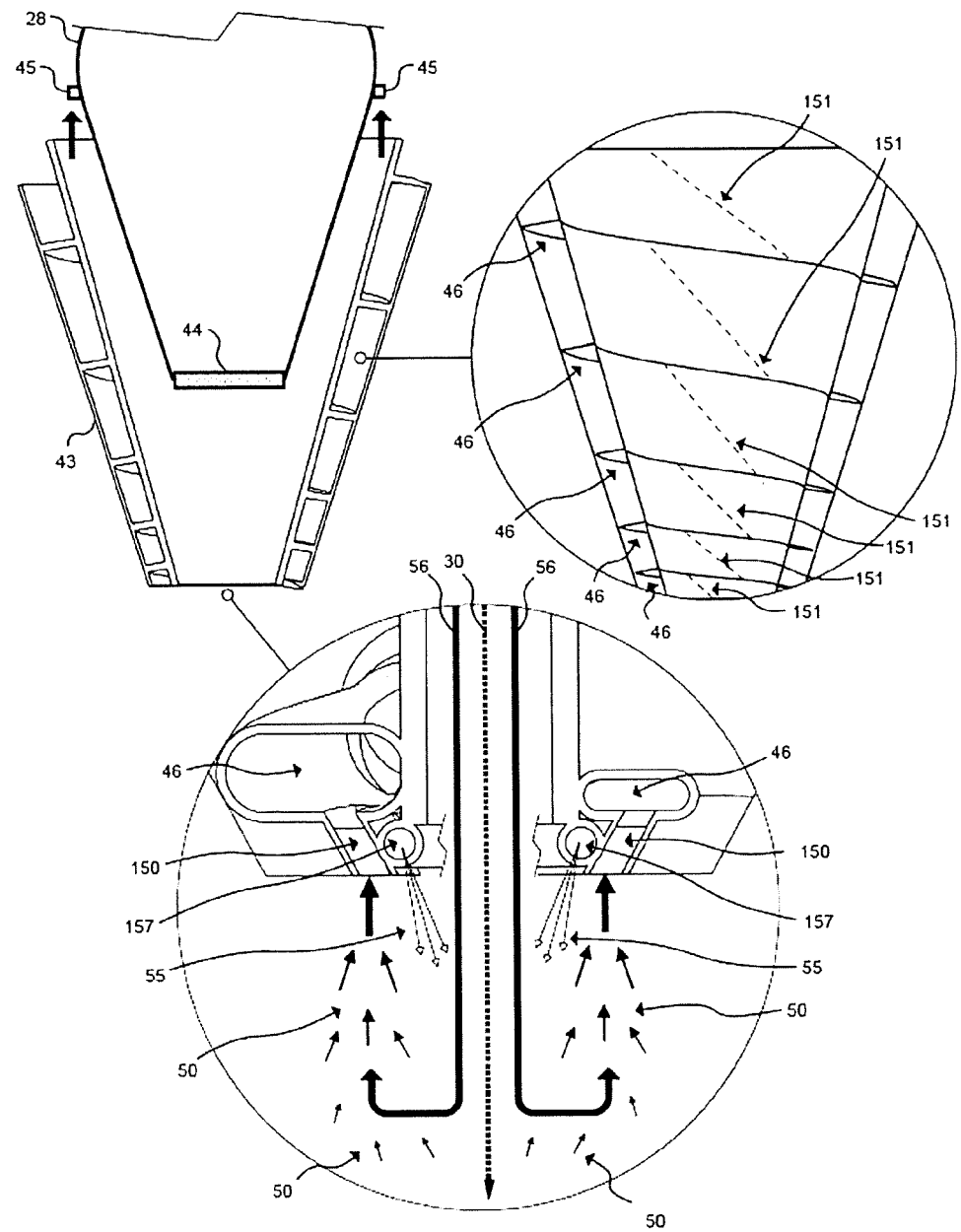
FIG. 9 depicts positioning and internal structure of a consumable shield/particle collector of the system of FIG. 1.

The consumable filter shield 43 will now be described, with reference to FIG. 9 of the drawings.

In the embodiment, an operational distance of the end effector 28 from the biological tissue 12 is between 150 and 300 mm. This distance is the collective working range for the sensors and light beam fine motion means. It also allows for a physical gap where an ablation plume can be ejected without immediately coating the outer surface of the end effector 28 that would result in contamination.

However, while the distance is helpful in preventing contamination it poses an increased risk of providing room for objects, and—more critically—portions of humans (other than the patient 14), to accidentally be positioned between the end effector 28 and the biological tissue 12. A primary danger is the laser beam 30 which could cause damage to soft biological tissue (of a human other than the patient 14) that happened to be occluding the target when it fires. Although the risk of injury decreases exponentially the further the distance from the focus point (since the energy density or fluence in joules (i.e. radiant laser energy per $cm^2$) decreases away from the focus) of the laser beam 30, it is still a risk to members of the surgical team during a procedure. Another risk is a non-human object that is shiny or mirror-like causing a specular reflection of laser energy. This, however, is a very small risk as any reflected laser energy will be likely scattered and un-focused, with the additional protection of safety glasses being mandatory for the operating staff for eye protection in the embodiment during use.

In order to form a physical barrier to the danger zone defined by the vertical space between the biological tissue 12 and the end effector 28, the system 10 comprises shielding for providing protection, having the form of an open-ended cone shaped consumable filter shield 43 in the embodiment. A larger open end of the consumable filter shield 43 is attached to the end effector 28 via attachment points 45 that securely hold the consumable filter shield 43 in place. A smaller open end of the consumable filter shield 43 provides a space, or gap, between itself and the target biological tissue 12. Such a gap advantageously: allows for easy visual inspection by a user of the system 10, such as a surgeon 16, while an ablation action is occurring; serves as a precaution against collisions between a biological tissue 12 that is shifting in location and the consumable filter shield 43; and allows working space, for example for retractors, suction, irrigation or other surgical tools.

Water 55 (or a suitable alternative) is applied to the biological tissue 12 via a plurality of water sprayers 157 that is operable to enhance the ablation process and act as a coolant for the biological tissue 12.

As mentioned above, microscopic particles of the ablation plume 50 are a health hazard to the operating staff of the system 10 and the patient 14, as inhaling the particles is damaging to the lungs. A preferred solution to this problem is for the consumable filter shield 43 to comprise particle collectors 150 in the form of a plurality of openings operatively positioned relatively close to the location where the ablation vapour is ejected to ensure that it collects the majority of the particulate material in the plume 50. The vacuum 153 draws the plume 50 into the particle collectors 150 and into the spiral conduit 46 that encircles the consumable filter shield 43.

The consumable filter shield 43 is operable to channel compressed air 56 out the smaller open end as a means of plume control 149. The compressed air 56 flow directs the plume away from the light beam 30 and towards the particle collectors 150.

An initial method of filtering and collecting the ablated material is through a series of "traps" and filters 151 built into a spiral conduit 46 around the consumable filter shield 43. So, rather than the consumable filter shield 43 being a single layer of suitable material, such as plastic, it has an outer layer and an inner layer. In such an embodiment, a sloped divider, as illustrated in FIG. 9 of the drawings, can then have a series of angled filters 151 that will allow ablated material to be progressively filtered (largest to smallest particles) and collect in areas away from the direct suction airflow. A particle collector 150 is preferably fairly narrow in its cross-section. This will cause the air flow rate to be high (i.e. strong vacuum). The spiral conduit 46 can increase in height as it travels up the consumable filter shield 43. This will in turn decrease the air flow as the cross-section becomes larger and heavier ablated material will lose velocity and fall to the bottom of the spiral conduit 46. By having angled filters forming the traps 151 positioned along the spiral conduit 46 the ablated material will collect and not slide back down. By controlling the rate of increase in the spiral conduit 46 cross-section, the volume of the ablated material collecting at each point can be controlled from studying the relative percentage distribution of ablated material density. Preferably, by the time the spiral conduit 46 reaches the cavity where the vacuum tube connects, the spiral conduit 46 cross-section increases significantly and even fine ablated material can be collected.

By collecting a portion of the ablated material in the consumable filter shield 43, to be disposed of after each surgery involving the system 10 in the embodiment, the total ablated material that needs to be collected by the fine particle filter 152 is reduced. This advantageously extends the working lifetime of the more expensive fine particle filter 152 which would otherwise become clogged with ablated material in a very short time given the approximately 50 $cm^3$ of biological tissue 12 that is ablated in a TKR.

Figure 10:
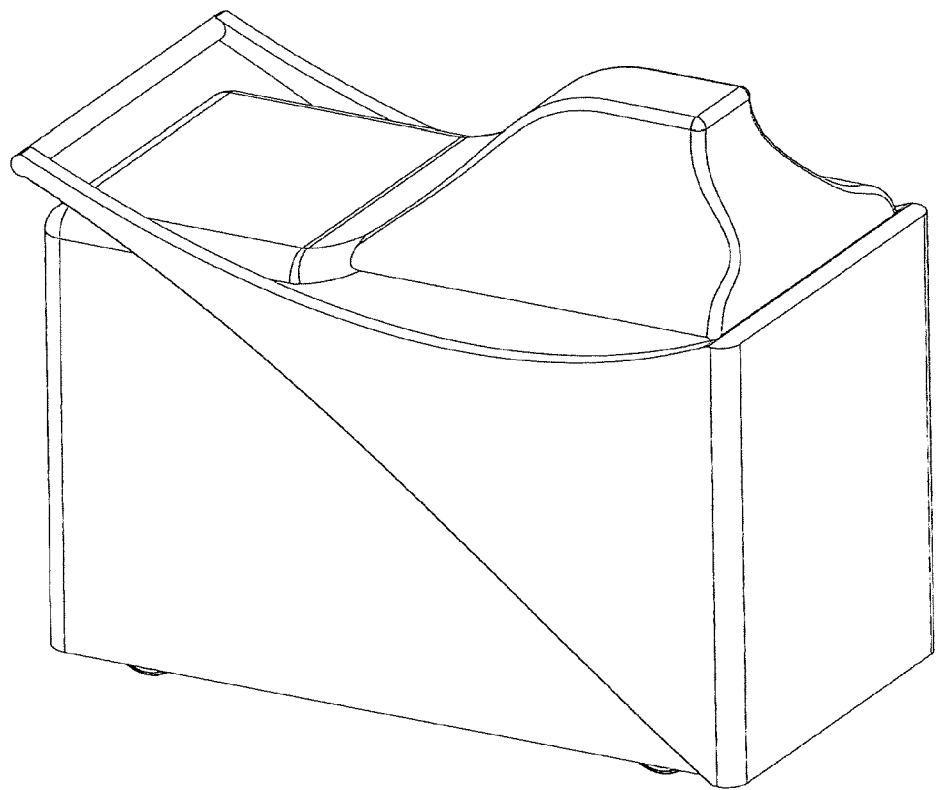
FIG. 10 depicts a base unit of the system of FIG. 1.

FIG. 10 of the drawings depicts an embodiment of the base unit 27, containing all the equipment and consumables that makes up the system 10 and isn't installed in the end effector 28. Some of the equipment is bulky and heavy, which makes it ideal to position low within the base unit 27 to lower the centre of gravity and stabilise the system 10 for operation.

Communication and conduit with the end effector 28 is via a bundled cable that is secured to, or within, the robot arm 105. Amongst other things, the bundled cable contains electrical power 41; coolant 40 (to/from); partially filtered air 51; water 55; compressed air 56; control wires and/or fibre optics 36. By partitioning the bundle into insulated conduits, coolant 40 from the chiller 140 can be packed closely with the water 55 tube along the length of the bundled cable. This advantageously results in the water 55 being cooled by virtue of the arrangement within the bundled cable alone, reducing the complexity of the system 10 and eliminating the need for a separate process of cooling the water 55.

Figure 11:
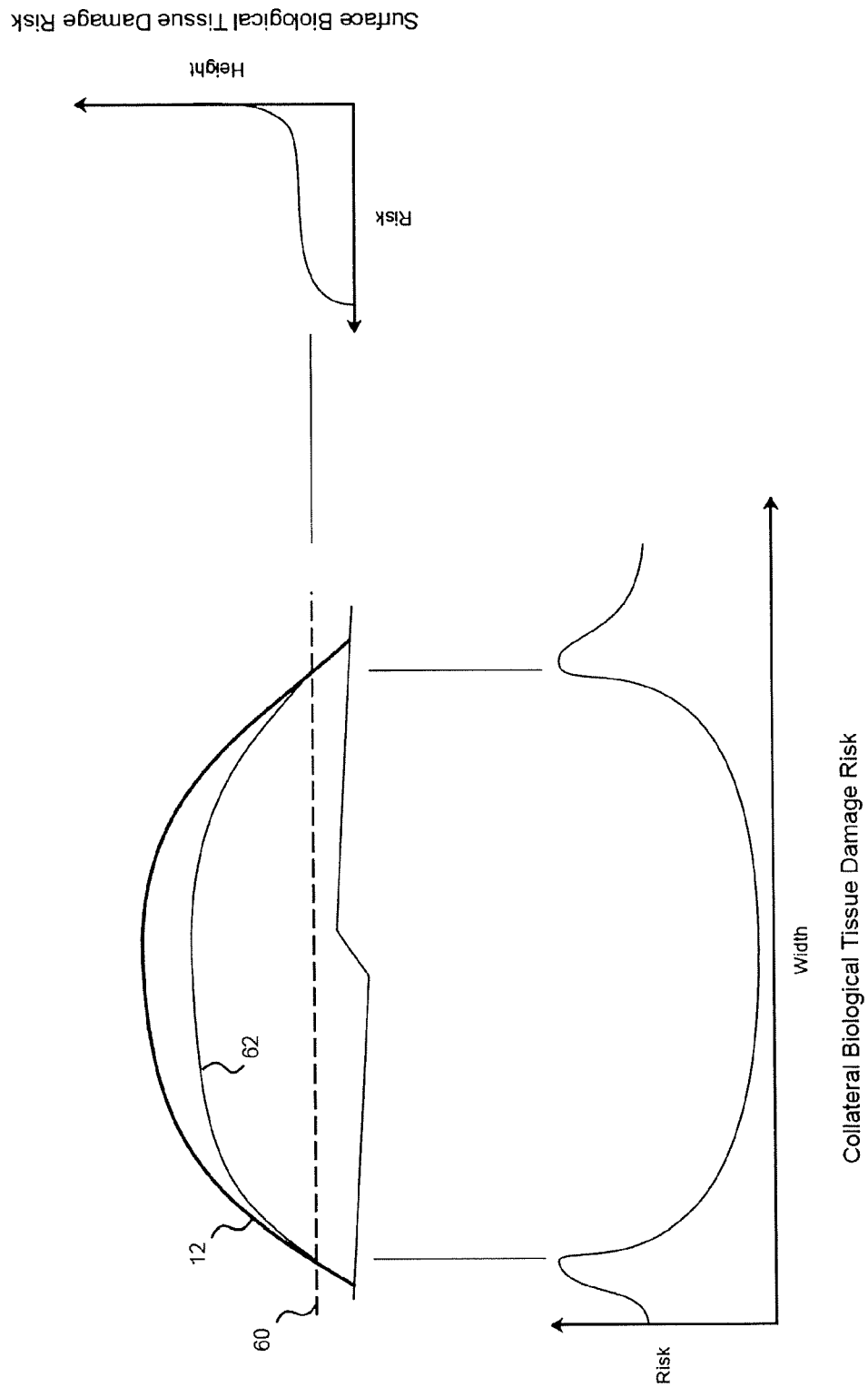
FIG. 11 depicts a graphical representation of ablation run risk to target and non-target "collateral" tissue.

FIG. 11 of the drawings depicts a cross-section of biological tissue 12 with a planned resection 60 marked as a dashed line. The biological tissue 12 above the line indicates the amount of material requiring ablation and the material below the line should be left undamaged.

Each laser pulse ablates an extremely small volume of material. Given that each complete resection 60 requires a very large volume to be ablated it follows that there will need to be a significantly large number of laser pulses.

For a resection 60 to be completed within the required period of time the system 10 of the embodiment preferably performs these laser pulses almost as quickly as the generated subtractive laser beam 30 and means of fine motion will allow.

However, a competing requirement is that the ablation be safely and accurately performed. The predominant way for the system 10 to sense the biological tissue 12 and surrounding working environment is with the imaging or scanning sensors of the sets of sensors 101 and 102. This provides the system 10 with a rich set of data to analyse and determine with confidence the points where the laser pulses are directed to ablate the correct material and that there is no other material in the way. However, some of the imaging and scanning sensors of the sets of sensors 101 and 102 take tens to hundreds of milliseconds to sense their environment. Were the system 10 to use these senses between each laser pulse it would take an unacceptable amount of time to complete a resection 60. It is accordingly undesirable to re-sense the biological tissue 12 between each single pulse of the laser in the embodiment.

The solution of the embodiment is to batch the laser pulses into an ablation run 62 comprising a pre-calculated set of pulses at different locations across the surface of the biological tissue 12. The system 10 is operable to perform each ablation run 62 after sensing the environment. The resection is performed in multiple ablation runs 62 that progressively reduce the tissue surface until the desired final resection 60 surface is achieved. Such operation may provide an optimal balance of sensing (assured) and speed.

As depicted in FIG. 11, the risk of collateral tissue damage is greatest around the edges of the volume of biological tissue 12 being ablated, representing the danger of miss-targeting with the light beam 30. In addition, the risk of surface tissue damage is greatest approaching the final resection 60 location, representing the danger of continuing to ablate the surface beyond the ideal point.

Laser parameters of the system 10 will now be described.

The system 10 interacts with the surgical environment through several actuators including the laser module 130, fine motion means (in the preferred embodiment a laser scan head 117), robot arm 105, plume control 149 and water sprayer 157. Each of these components has several control parameters. These include:

| Actuator | Parameter | Reasonable Range | Typical Range |
| --- | --- | --- | --- |
| Laser | Average Output Power (W) | 0.1-2000 W | 0.5-200 W |
| Laser | Pulse Repetition Rate (Hz) | 1-2000 Hz | 200-1000 Hz |
| Laser | Pulse Duration (μs) | 0.1-1000 μs | 100-400 μs |
| Laser | Spot Size (μm) | 100-10000 μm | 300-1000 μm |
| Laser | Energy Density (J/cm$^2$) | 0.1-1000 J/cm$^2$ | 10-150 J/cm$^2$ |
| Laser scan head | Traverse Speed (mm/s) | 1-40000 mm/s | 400-900 mm/s |

The range listed next to each parameter in the table above is an estimate of the upper bound, lower bound, and typical range for each parameter in the embodiment that is expected to perform a reasonable resection.

The laser parameters include: Average Output Power (in Watts)—the laser power of the light beam 30 generated; Pulse Duration (in microseconds)—the amount of time each pulse of laser is generated; Spot Size (in micrometres)—the diameter of the focused light beam 30; Energy Density (in joules per square centimetre)—the laser energy delivered per unit area; and Pulse Frequency (cycles per second)—the number of pulses generated each second.

For flat plane ablation with a circular beam profile, in order to result in a smooth surface, the laser ablation must overlap in a pattern or grid such that the surface is reduced evenly.

Indicative research by the inventors suggests that a beam diameter of 200 to 600 microns and an overlapping pattern is sufficient to produce a flat ablated surface.

This means that any given point on the surface will be ablated multiple times due to the overlapping alone, even before any consideration of the depth of the ablation required. This accentuates the need for a quick method of firing the laser light beam 30 at the surface.

Figure 12A:
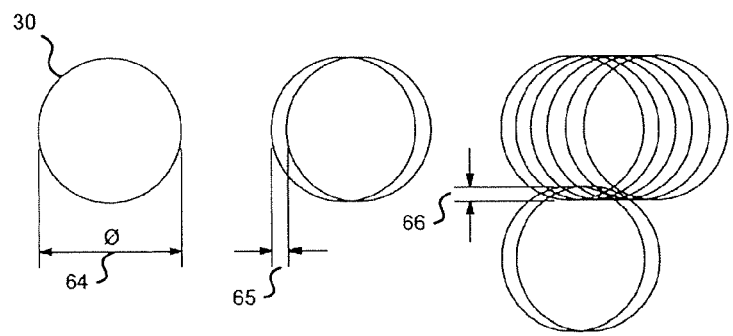
FIGS. 12A and 12B depict laser beam ablation dimensions and patterns of the system of FIG. 1.

FIG. 12A of the drawings depicts an example of preferred laser beam ablation channel dimensions. When creating a channel the light beam diameter or spot size 64 indicates the width of the channel with the subsequent pulse overlapping the first with a gap 65. By continuing in this manner an ablated channel is created in the material. To create a final flat surface, multiple channels can be created with a stride 66 between them to allow for the sides of the channels to be removed.

However, multiple laser pulses across the surface in such a manner accumulates thermal impact, which may cause damage to the biological tissue 12 that is unwanted especially in the final resection 60 surface.

Figure 12B:
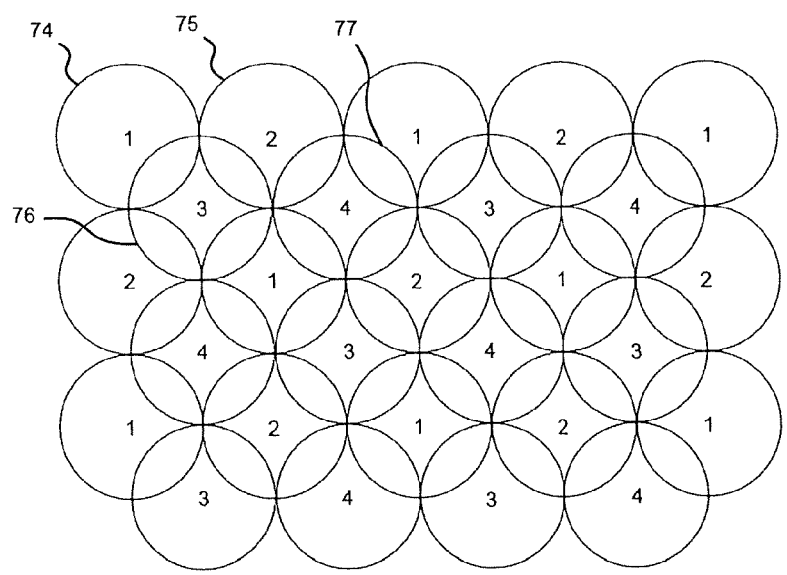

An alternative ablation pattern is an interleaved grid of laser pulses across the surface, as depicted in FIG. 12B.

The first series of pulses 74, marked with a '1', are spaced to prevent a build-up of thermal impact in the same localized area. The second series of pulses 75, marked with a '2', are spaced between the first series. The third and fourth series of pulses 76 and 77, marked '3' and '4' respectively, overlap and complete the surface between the first and second series. In this manner an optimal coverage is achieved with the minimal thermal impact.

Figure 13:
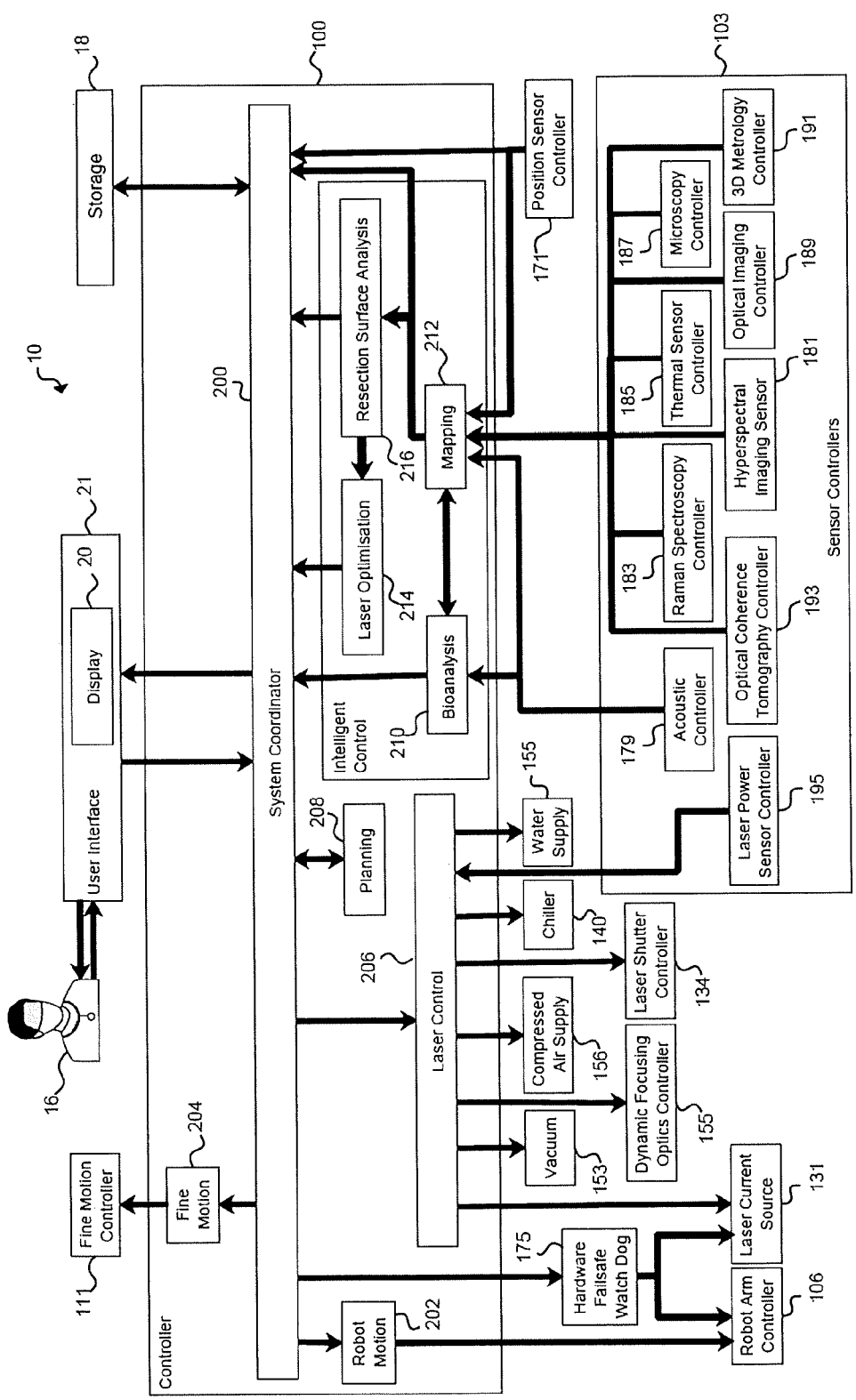
FIG. 13 depicts architecture of a controller of the system of FIG. 1.

FIG. 13 of the drawings depicts architecture of the controller.

The controller 100 comprises system management software running on a computer. The controller 100 further comprises the software that manages the system 10. The controller 100 optionally further comprises an artificially intelligent control system operable to fuse and interpret input received in real-time to operate the system 10.

The responsibilities of the controller 100 include the following areas: communicating with the hardware components of the system 10; processing the various information to decide on the actions to take given the circumstances; communicating the current operating status of the system 10 on the user interface 21; and loading and storing data to and from storage 18.

Particularly, the controller 100 is operable to utilise and control: sensors of the sets of sensors 101 and 102, one or more of a plurality of representations pertaining to the biological tissue 12 and work to be done, machine perception, the robot arm 105, and the laser related components. In such manner, the controller 100 is operable to implement actions in accordance with decisions made and commands received.

The controller 100 comprises processing means in the form of a processor.

The storage 18 comprises read only memory (ROM) and random access memory (RAM). Amongst other things, the storage 18 provides patient specific data and procedure plans for the system 10 to perform.

The system 10 is capable of receiving instructions that may be held in the ROM or RAM and may be executed by the processor. The processor is operable to perform actions under control of electronic program instructions, as will be described in further detail below, including processing/executing instructions and managing the flow of data and information through the system 10.

In the embodiment, electronic program instructions for the system 10 are provided via software stored on the storage 18.

As will be described in further detail, via the software, the system 10 is operable to perform functions including: extracting, converting and combining data and recording all real time data passing through the system 10.

All data and information collected is distributed within the system 10 for use as described herein.

The system 10 also includes an operating system which is capable of issuing commands and is arranged to interact with the software to cause the system to carry out the respective steps, functions and/or procedures in accordance with the embodiment of the invention described herein. The operating system is appropriate for the system 10.

The system 10 is operable to communicate via one or more communications link(s), which may variously connect to one or more remote devices such as servers, personal computers, terminals, wireless or handheld computing devices, landline communication devices, or mobile communication devices such as a mobile (cell) telephone. At least one of a plurality of communications link(s) may be connected to an external computing network through a telecommunications network.

The software, and other electronic instructions or programs for the computing components of the system 10 can be written in any suitable language, as are well known to persons skilled in the art. In embodiments of the invention, the electronic program instructions may be provided as stand-alone application(s), as a set or plurality of applications, via a network, or added as middleware, depending on the requirements of the implementation or embodiment.

In alternative embodiments of the invention, the software may comprise one or more modules, and may be implemented in hardware. In such a case, for example, the modules may be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA) and the like.

The computing means can be a system of any suitable type, including: a programmable logic controller (PLC); digital signal processor (DSP); microcontroller; personal, notebook or tablet computer, or dedicated servers or networked servers.

The processor can be any one or a combination of one or more custom made or commercially available processor, a central processing unit (CPU),a graphics processing unit (GPU), a data signal processor (DSP) or an auxiliary processor among several processors associated with the computing means. In embodiments of the invention, the processing means may be a semiconductor based microprocessor (in the form of a microchip) or a macro processor, for example.

In embodiments of the invention, the storage can include any one or combination of volatile memory elements (e.g., random access memory (RAM) such as dynamic random access memory (DRAM), static random access memory (SRAM)) and non-volatile memory elements (e.g., read only memory (ROM), erasable programmable read only memory (EPROM), electronically erasable programmable read only memory (EEPROM), programmable read only memory (PROM), tape, compact disc read only memory (CD-ROM), etc.). The respective storage may incorporate electronic, magnetic, optical and/or other types of storage media. Furthermore, the storage can have a distributed architecture, where various components are situated remotely from one another, but can be accessed by the processing means. For example, the ROM may store various instructions, programs, software, or applications to be executed by the processing means to control the operation of the system 10 and the RAM may temporarily store variables or results of the operations.

The use and operation of computers using software applications is well-known to persons skilled in the art and need not be described in any further detail herein except as is relevant to the present invention.

Furthermore, any suitable communication protocol can be used to facilitate connection and communication between any subsystems or components of the system 10, and other devices or systems, including wired and wireless, as are well known to persons skilled in the art and need not be described in any further detail herein except as is relevant to the present invention.

Where the words "store", "hold" and "save" or similar words are used in the context of the present invention, they are to be understood as including reference to the retaining or holding of data or information both permanently and/or temporarily in the storage means, device or medium for later retrieval, and momentarily or instantaneously, for example as part of a processing operation being performed.

Additionally, where the terms "system", "device", and "machine" are used in the context of the present invention, they are to be understood as including reference to any group of functionally related or interacting, interrelated, interdependent or associated components or elements that may be located in proximity to, separate from, integrated with, or discrete from, each other.

Furthermore, in embodiments of the invention, the word "determining" is understood to include receiving or accessing the relevant data or information.

A system coordinator 200 encompasses the whole controller 100 and forms the 'backbone' that organises and interconnects all of the software components of the system 10.

The responsibilities of the system coordinator 200 include, and it is operable to perform, the following: configure the components of the system 10; manage the lifetime of the components; provide runtime services to the components; and enforce the overall safety of the system.

Components of the system 10 facilitating operations at the direction of the system coordinator 200 include: a fine motion component 204; a robot motion component 202; a laser control component 206; a planning component 208; a bioanalysis component 210; a laser optimization component 214; a mapping component 212; and a resection surface analysis component 216.

In further detail, the system coordinator 200 is operable to facilitate the following functions.

Configure: Operation of the system 10 is determined by the specific set of components that are included and configured by the system coordinator 200.

Component versions: Each component of the system 10 has a specified interface that is used by the system coordinator 200 to access its functionality. As the system coordinator 200 controls the configuration and initialisation of the components, it is possible for any component to be replaced by a specially crafted alternative that honours the component's interface but performs a different function. This is useful for activities including development, testing, verification, quality control, and simulation.

Development: In the early stages of development of the system 10 there may be a version of most components that will perform no real function at all, but purely exist to satisfy the interface requirements with a non-functional 'stub'. These 'stub' components allow the system coordinator 200 to facilitate focused development on a specific single live component while the remaining system 10 is functionally neutral.

Simulation: Simulation versions of components can be created that will 'play back' pre-recorded or fabricated functionality and data. The primary purpose of this version of component is supporting integration testing and verification of functionality under success and failure scenarios. The secondary purpose of this version can be the recreation and analysis of the prior recorded live run.

Live: There is a single live version of each component that is used in the production build of the embodiment. This provides the real-world functionality required by the deployed product.

Manage: The system coordinator 200 is operable to manage the operation and lifetime of each component.

Component isolation: The run-time environment of each component can be set up and controlled by the system coordinator 200 depending on the purpose and circumstances of the instantiation. For development it may be that each component is executed in serial to assist in debugging and simplify the data flow for deterministic timing. For testing, validation, and live environments however, it is possible to set up separate processing threads for each component to allow for time critical functionality to be more finely controlled.

State management: The system coordinator 200 is operable to maintain the state of the system 10 as it transitions from task to task. This will invoke various functionality in each component as necessary for the current operation of the task at hand.

Component coordination/data flow: In the embodiment, data is not sent directly from component to component but rather through the system coordinator 200. This allows for low coupling between the components for easier development and testing. It also provides an insertion point where the system coordinator 200 can perform additional functions on the data whilst in transit such as sanity checks, logging and data recording.

Runtime services: In the embodiment, each component requires access to global functionality that is common and synchronised across the system 10. This may also encapsulate platform dependent functionality of the underlying services. This set of functionality is provided by the system coordinator 200 to each component.

Logging: Centralised logging allows each component to provide runtime status information that can be directed to several different destinations such as console, log file or database. This logging can be configured by the system coordinator 200 to levels of severity, verbosity and granularity.

Data recording: For any particular run of the system 10, the data flow between the components can be recorded to a database for later analysis, verification or playback. This data recording can be used to configure a simulation component in later runs.

Timing (high resolution clock): A number of the actions of the system 10 require accurate timing. A high resolution clock is provided that is operable to allow for at least microsecond level timekeeping. Where the system 10 is in simulation mode this clock can be synchronised to an external source such as a provided data recording.

Safety: The safety of the system 10 is paramount, and the system coordinator 200 is ultimately responsible for the enforcement of fail-safe procedures in the embodiment. When a safety issue is detected, the system coordinator 200 is operable to ensure that each component is entered into an orderly fail-safe and the system 10 placed into a safe posture for further instructions by the operating staff. There are several ways that the system coordinator 200 can detect issues that would cause the system 10 to go into fail-safe, as will be described in further detail.

Component active fault: In the embodiment, each component can actively report a fault to the system coordinator 200 that will initiate the system fail-safe. This could be due to one or more of detected hardware failure, operations outside of safe parameters or unexpected or unknown operational situations, for example Component passive fault: In the embodiment, each component constantly reports on its own correct functioning and operation. Should a component not report in a timely manner within the required specification the system coordinator 200 is operable to assume that it is in an undesirable bad or unknown state and initiate the fail-safe.

The system coordinator 200 itself is not assumed to be faultless and in the embodiment must report its own correct functioning to an independent hardware device, herein referred to as a watch dog 175 that will reset a hardware timer upon receipt of each successful report. Should the system coordinator 200 not report within the required time period the watch dog 175 is operable to trigger the hardwired shutdown of all hardware of the system 10. For the robot arm 105 this may comprise a safety circuit and for the laser subsystem this may comprise activating a shutter and disabling the relevant power relay.

Regarding the watch dog 175, the system 10 of the embodiment cannot rely solely on the correct operation of the controller 100 software, underlying operating system, drivers, or hardware. There is always the possibility of a failure of any one of these layers that may or may not be detectable by the software that is running.

Figure 14:
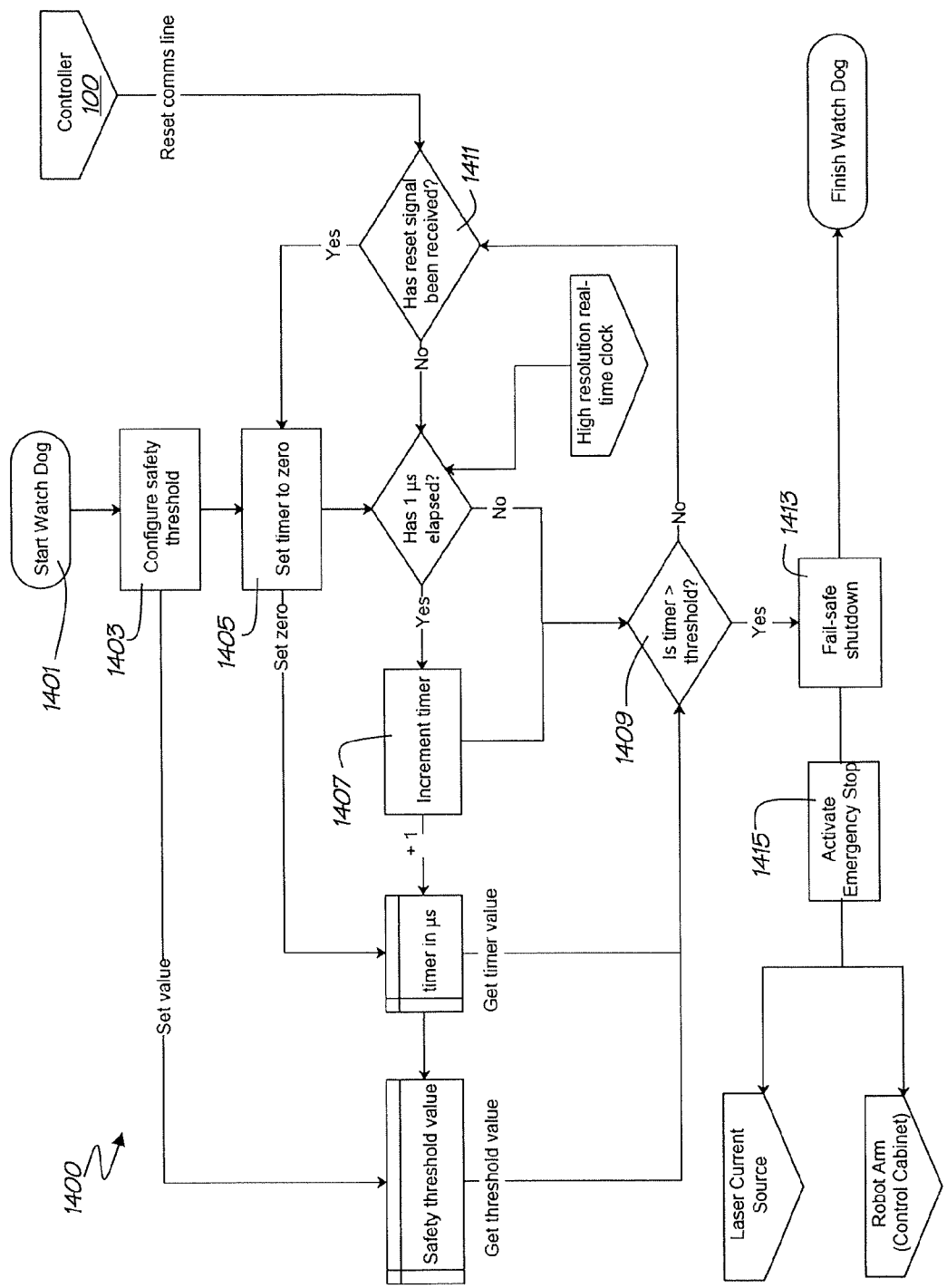
FIG. 14 depicts a flow chart of actions taken during a watch dog (hardware failsafe) procedure of the system of FIG. 1.

FIG. 14 of the drawings depicts a flow chart of a method 1400 of actions taken during a watch dog (hardware failsafe) procedure of the system 10.

The watch dog 175 is started 1401 by the controller 100 on initialization of the system 10. It is configured 1403 with a safety threshold in microseconds, and the timer is reset to zero 1405.

For every reading from the high resolution real-time clock, the amount of time that has elapsed is incrementally added 1407 to the timer. The timer represents the number of microseconds that has elapsed since the system 10 last reported itself in a known, good state.

The timer is compared 1409 to the safety threshold value.

If it has not exceeded the threshold, then it will loop back to seeing if it has received 1411 a timer reset signal from the controller 100. When a reset signal is received the timer is set back to zero.

If it exceeds the threshold, then the fail-safe shutdown process is initiated 1413. For the system 10 of the embodiment this comprises activating an emergency stop 1415 on the two components that have a critical risk: the laser current source 131 and the robot arm 105 (robot arm controller 106). Such action will immediately stop the laser light beam 30 from firing and the robot arm 105 from moving.

Figure 15:
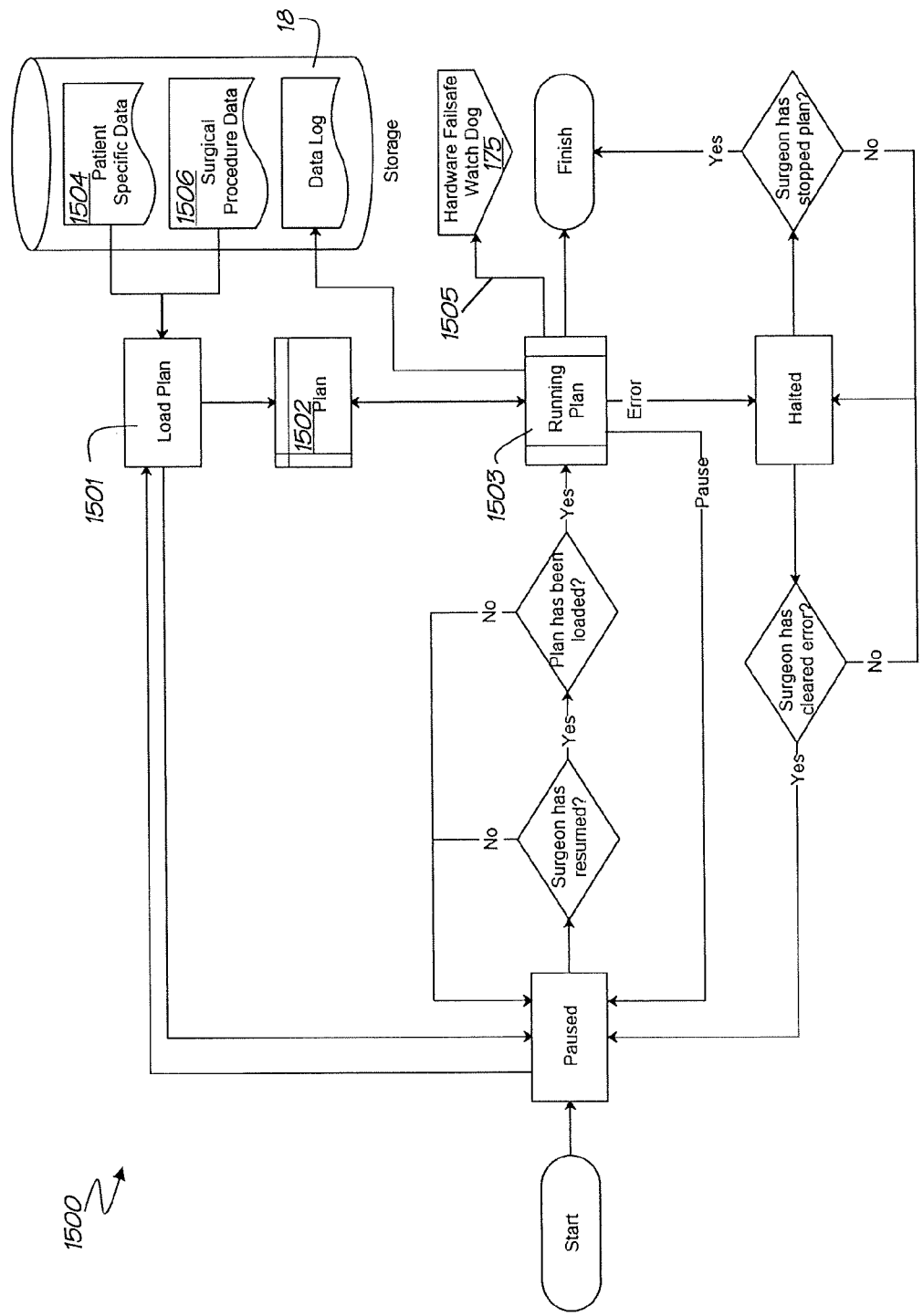
FIG. 15 depicts a flow chart of actions performed by a system coordinator of the controller of FIG. 13.

FIG. 15 depicts a flow chart of a method 1500 of actions performed by the system coordinator 200.

The system coordinator 200 starts in a paused state.

The surgeon 16 will direct the system coordinator 200 to load 1501 a plan 1502 for action(s) to be performed from storage 18. The plan 1502 consists of patient specific data 1504 and surgical procedure data 1506.

If the surgeon 16 chooses to resume the system 10, and there has been a plan loaded, the plan 1502 will be executed 1503 by the running plan process.

During the running plan process 1503, the hardware failsafe watch dog 175 is continually sent 1505 an "everything is ok" signal that prevents the fail-safe from activating. Should the system coordinator 200 fail to send the signal within a threshold timeout then the system 10 is assumed to be in an unknown state and the hardware is set to a safe state as hereinbefore described above with reference to method 1400.

In the embodiment, the processing of input performed by the system coordinator 200 comprises an analysis of the input and a making of a decision on the basis of the analysis. Once a decision has been made, the system coordinator 200 is operable to initiate an action on the basis of the decision to control the robot arm 105 and the laser to work the biological tissue 12.

As part of the analysis, the system coordinator 200 is operable to generate based on input, and/or receive as input, at least one first representation of the biological tissue 12. In the embodiment, the at least one first representation of the biological tissue 12 comprises a representation of a first or pre-action (initial) state of the biological tissue 12 corresponding to an actual state of the biological tissue 12 prior to the at least one action of work being performed thereon. The at least one first representation of the biological tissue 12 includes parameters that describe or provide an indication of one or more characteristics of the biological tissue 12.

In the embodiment, the at least one first representation of the biological tissue 12 comprises a map or model of the pre-action state of the biological tissue 12.

Figure 16:
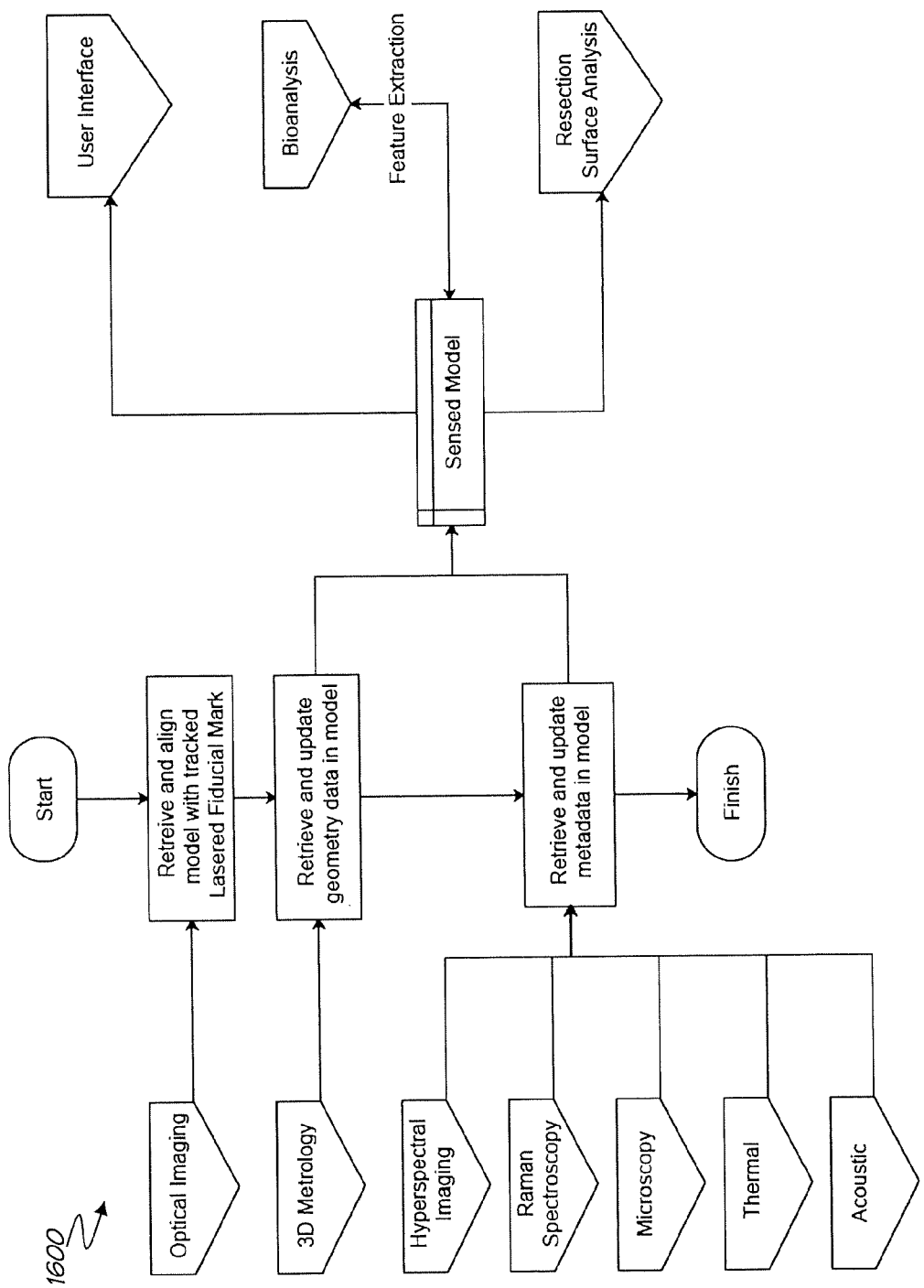
FIG. 16 depicts a flow chart of actions performed during a mapping operation of the controller of FIG. 13.

FIG. 16 depicts a flow chart of a method 1600 of actions performed during a mapping operation of the system 10 undertaken to generate the map.

The system 10 of the embodiment needs to understand the 3D surface and composition of the biological tissue 12 and surrounding environment. This representation of the physical reality is used by several subsystems of the system 10 to reason and plan the actions that will be performed. It is important that the accuracy of the mapping is sufficient for the system 10 to be able to safely and correctly perform resections of hard biological tissue.

There are several ways the system 10 senses the required mapping information, as follows.

As described herein, the system 10 is operable to collate all of this information and incorporate it into a cohesive model that parts of the system 10 can reason about given their own requirements.

The at least one first representation may comprise a plan for the work to be performed, which may comprise a setting of parameters defining one or more features or characteristics of the work.

The system 10 of the embodiment is operable to use a planning component to coordinate the actions required to correctly perform the necessary action, comprising resections of the surgical procedure in the embodiment.

Figure 17:
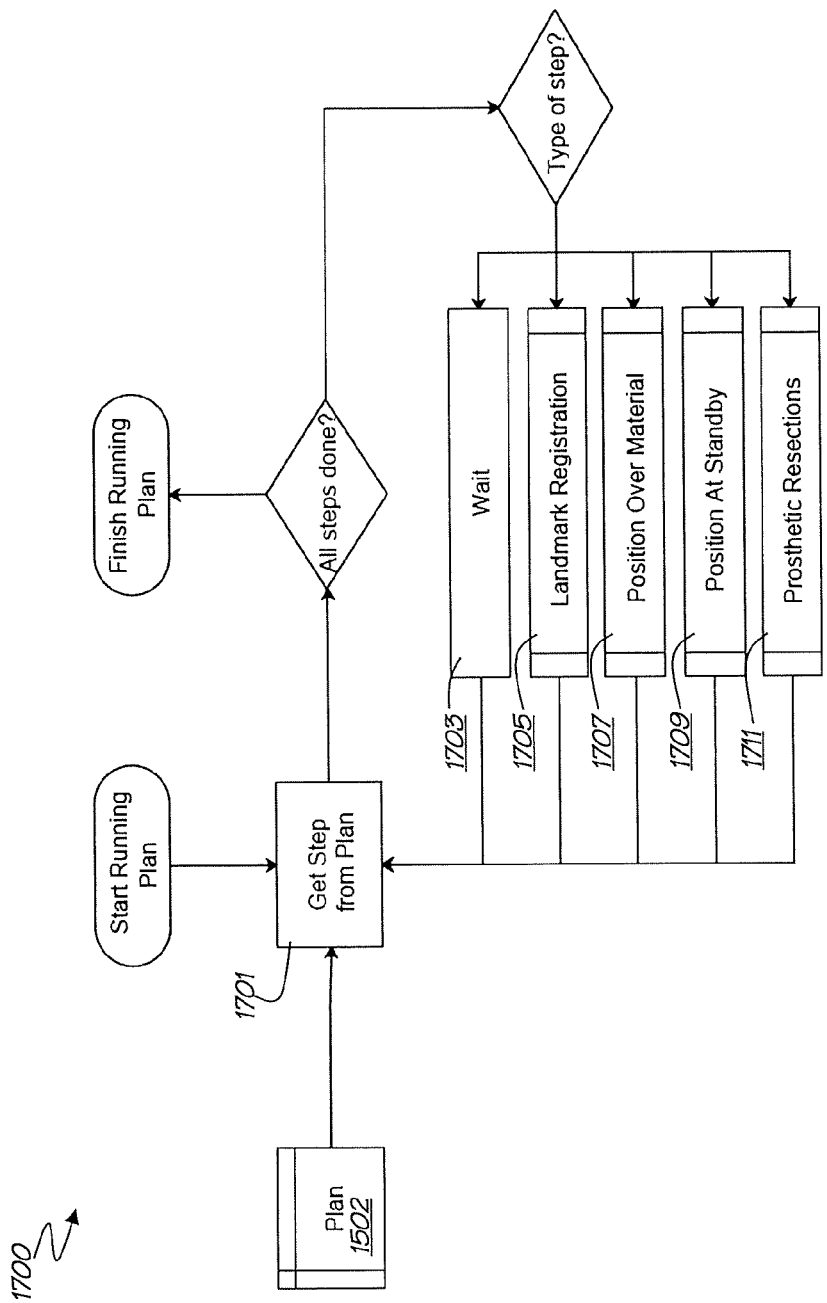
FIG. 17 depicts a flow chart of actions performed during a planning operation of the controller of FIG. 13.

FIG. 17 depicts a flow chart of a method 1700 of actions performed during a planning operation of the system 10.

The planning process controls the sequential actions that occur when following a plan 1502 that was loaded from storage 18.

The next step is retrieved 1701 from the plan and the matching step process is performed.

This is repeated until all the steps of the plan have been completed. In the embodiment, steps of the plan may include: a wait operation step 1703; a landmark registration operation step 1705; a position over material operation step 1707; a position at standby operation step 179; and a prosthetic resections operation step 1711.

Figure 18:
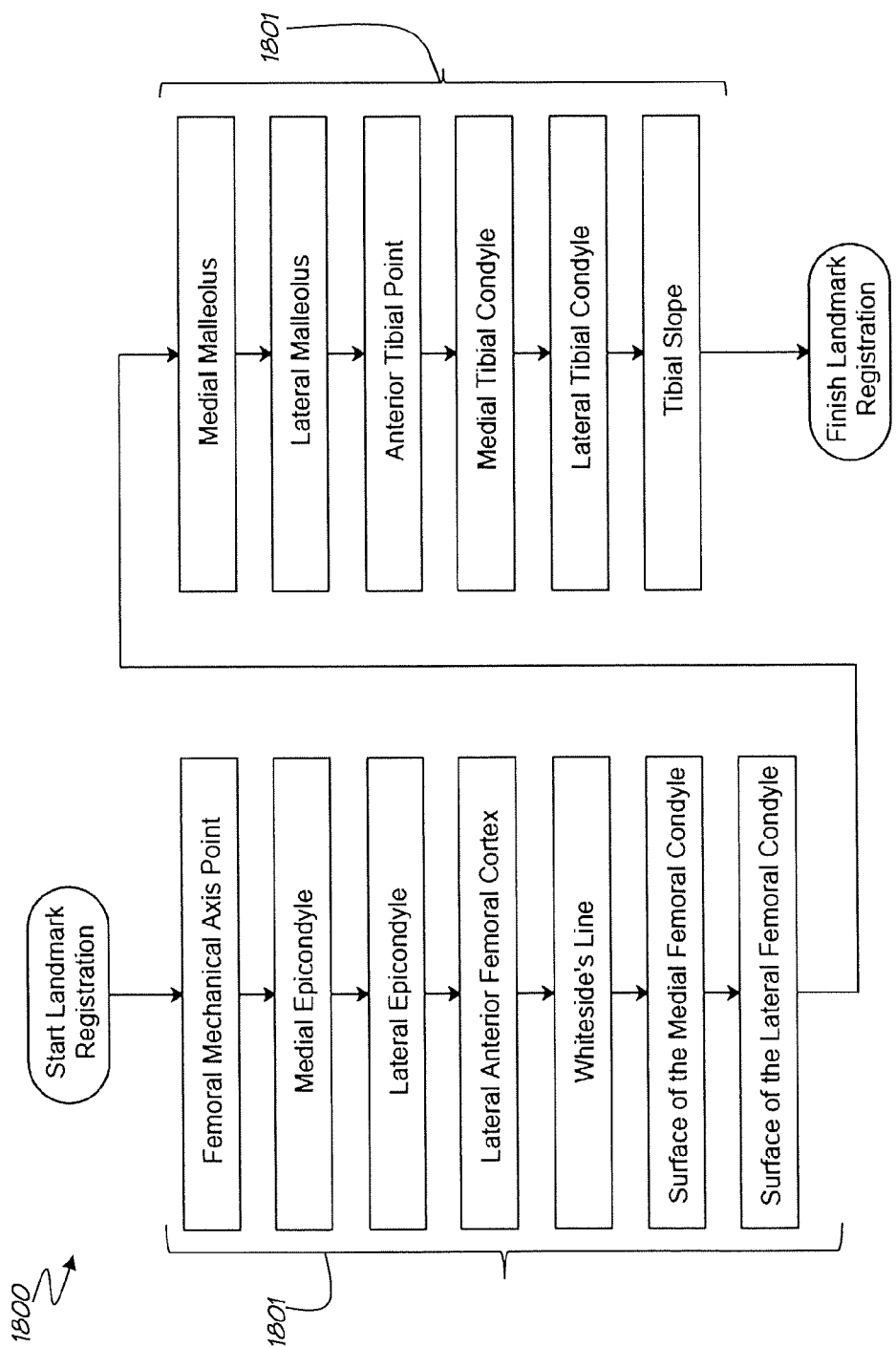
FIG. 18 depicts a flow chart of actions performed during a landmark registration operation of the planning operation of FIG. 17.

FIG. 18 depicts a flow chart of a method 1800 of actions performed during a landmark registration operation of the system 10.

The landmark registration process involves a step-by-step registration of points in three dimensional space by the surgeon 16 using a tool with an attached fiducial marker 70. The position sensor 170 determines the position of the working end of the tool when each point is prompted for by the user interface 21. In the embodiment in the context of a surgical procedure to the knee of patient 14, the points include the following sites 1801 in sequence between start of the landmark registration process and the end of the landmark registration process: Femoral Mechanical Axis Point; Medial Epicondyle; Lateral Epicondyle; Lateral Anterior Femoral Cortex; Whiteside's Line; Surface of the Medial Femoral Condyle; Surface of the Lateral Femoral Condyle; Medial Malleolus; Lateral Malleolus; Anterior Tibial Point; Medial Tibial Condyle; Lateral Tibial Condyle; and Tibial Slope.

Figure 19:
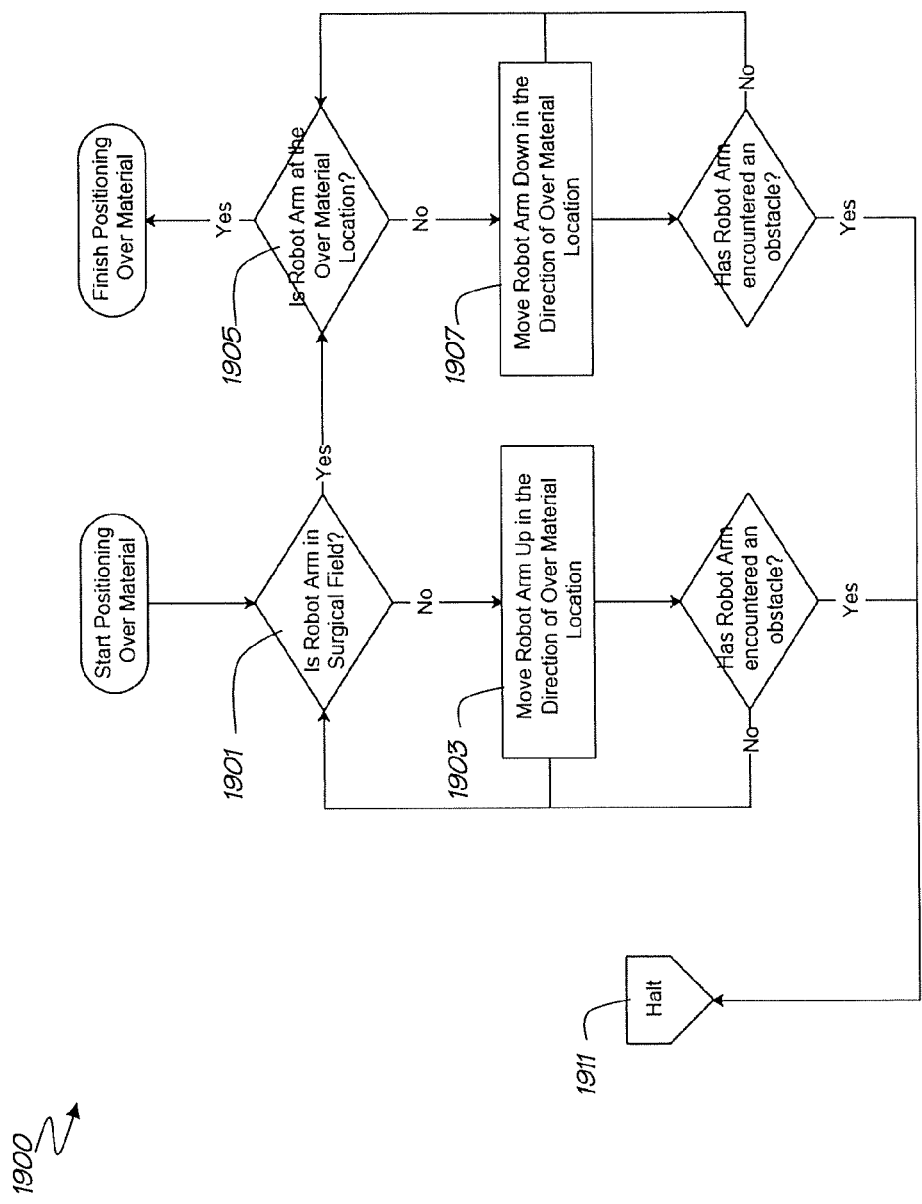
FIG. 19 depicts a flow chart of actions performed during a position over material operation of the planning operation of FIG. 17.

FIG. 19 depicts a flow chart of a method 1900 of actions performed during a position-over-material operation of the system 10.

The position-over-material process 1900 ensures that the robot arm 105 is safely manoeuvred to the correct relative position above the biological tissue 12.

Firstly a check 1901 is performed to determine whether the robot arm 105 is within a surgical field comprising prescribed conical volume of space originating at the biological tissue 12 and extending vertically such that sides of the cone are at 45°. If the robot arm 105 is not within the surgical field, the robot arm 105 is repositioned 1903 by raising the end effector 28 up to the extension limits while moving it laterally towards the biological tissue 12 until it is within the surgical field positioned over the biological tissue material to be worked upon.

Once the robot arm 105 is within the surgical field 1905 it will start to lower 1907 the end effector 28 towards the correct position above the biological tissue 12. Once it is in the correct position it will stop 1911 moving the robot arm 105.

Should the robot arm 105 encounter an obstacle at any stage, by virtue of being detected via increased torque forces on one or more joints of the manipulator 23, or by virtue of operation of one or more pressure sensitive pads on the outside of the segments of the manipulator 23, for example, then it will halt 1911 to prevent it from impacting on personnel or other objects in the environment.

Figure 20:
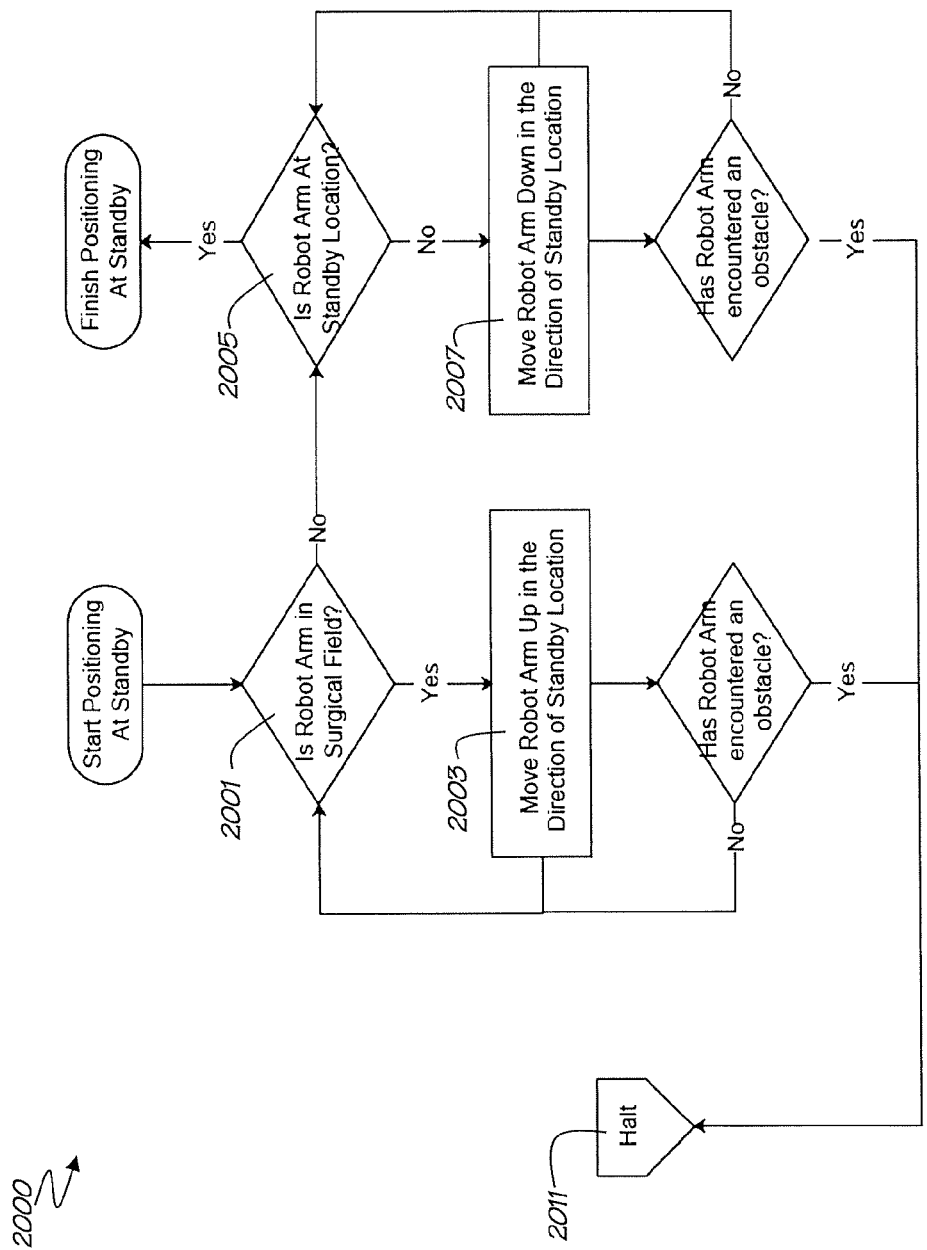
FIG. 20 depicts a flow chart of actions performed during a position at standby operation of the planning operation of FIG. 17.

FIG. 20 depicts a flow chart of a method 2000 of actions performed during a position at standby operation of the system 10.

This ensures that the robot arm 105 is safely manoeuvred away from the biological tissue 12 to a standby location.

If the robot arm 105 is within the surgical field 2001 then the end effector 28 is repositioned 2005 by raising it up towards the extension limits of the robot arm 105 while moving it laterally in the direction of the standby location. In the embodiment, the standby location is the position of the robot arm 105 over the base unit 27 such that it cannot interfere or be an obstacle to any reasonable actions that are performed in the surgical workspace.

Once the robot arm 105 is outside the surgical field over the standby location 2005, the end effector 28 is lowered 2007 towards the standby location while continuing to laterally move in that same direction until it has arrived. Then it will stop 2011.

In the same manner as the flow chart of a method 2100 of actions performed of method 1900 depicted in FIG. 19, should the robot arm 105 encounter an obstacle at any stage it will halt 2011.

Figure 21:
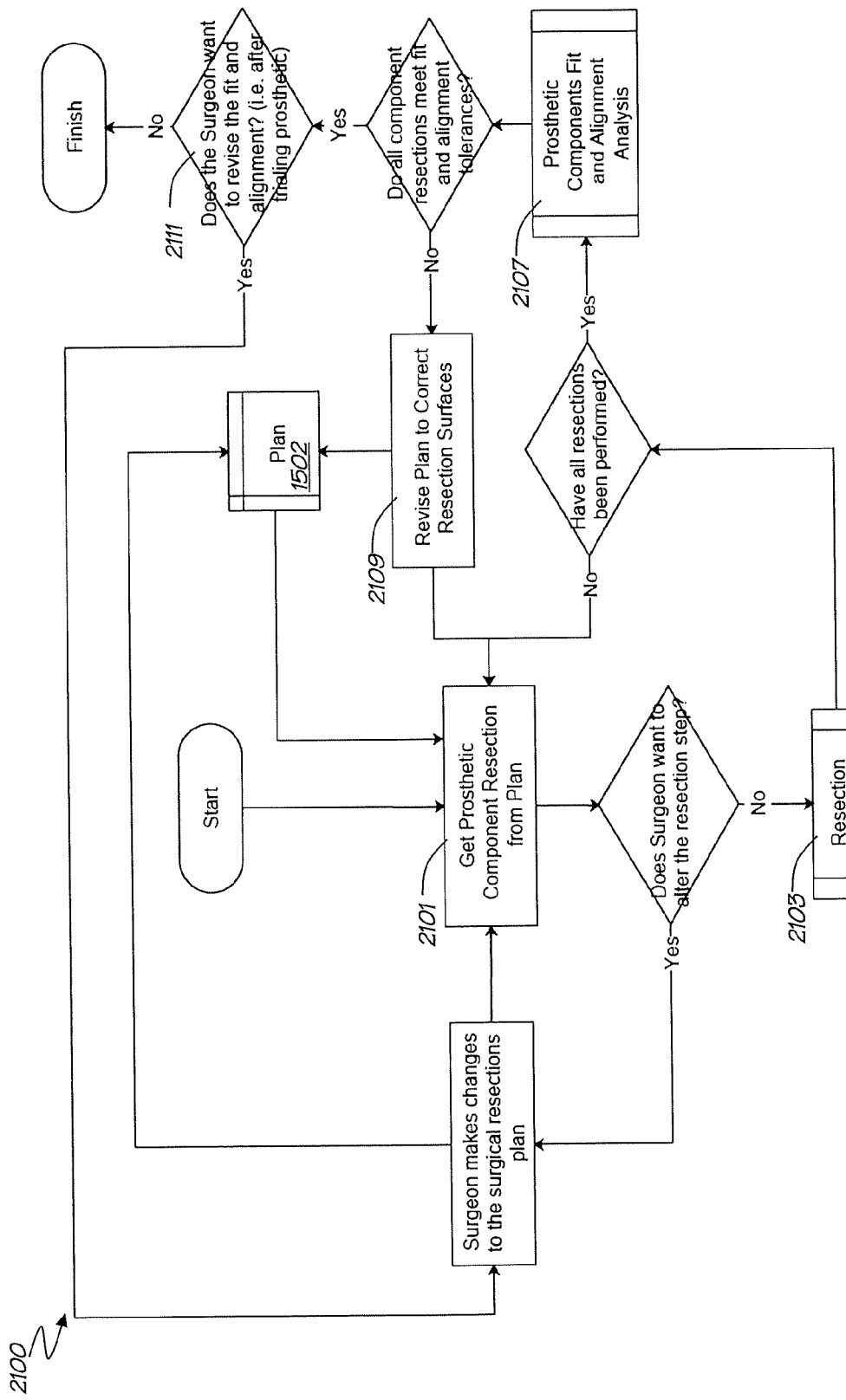
FIG. 21 depicts a flow chart of actions performed for a set of prosthetic component resections with fit and alignment analysis of the planning operation of FIG. 17.

FIG. 21 depicts a flow chart of a method 2100 of actions performed during a prosthetic resections operation of the system 10.

The process 2100 retrieves 2101 the next prosthetic component resection from the plan 1502. The order of the resections in the plan has been determined by the surgical procedure data as seen in FIG. 17.

The surgeon 16 is given the opportunity 2103 of altering or changing the planned resection prior to the system 10 actioning it. This may, for example, adjust the parameters of the resection, or select a different resection to be actioned next.

If the surgeon 16 does not want to alter the resection step then the system 10 is operable to perform the resection 2105 as will be described in further detail referring to FIG. 22.

If all the resections in the plan have not been performed yet, the process will retrieve 2101 the next resection from the plan until all resections have been performed.

Once all the resections in the plan have been performed, the system 10 is operable to perform a prosthetic components fit and alignment analysis 2107.

In this embodiment, this assessment is undertaken by the system 10 performing a prosthetic components fit and alignment analysis as will be described in further detail referring to FIG. 26.

If all the component resections do not meet the fit and alignment tolerances for sufficient positioning then the system 10 is operable to change 2109 the plan to perform revision resections steps to correct for the discrepancy between the ideal fit and alignment and the current geometric fit and alignment.

If the prosthetic components fit and alignment analysis is sufficient then the surgeon 16 is provided an opportunity to independently review 2111 the analysis and optionally make revisions to the resection plan to affect a variation on fit and alignment. This may be important after trialling the prosthetic and determining that the flexion and extension of the joint do not provide the correct clearances and adjustment resections or different sized prosthetic component(s) are required, for example.

Figure 22:
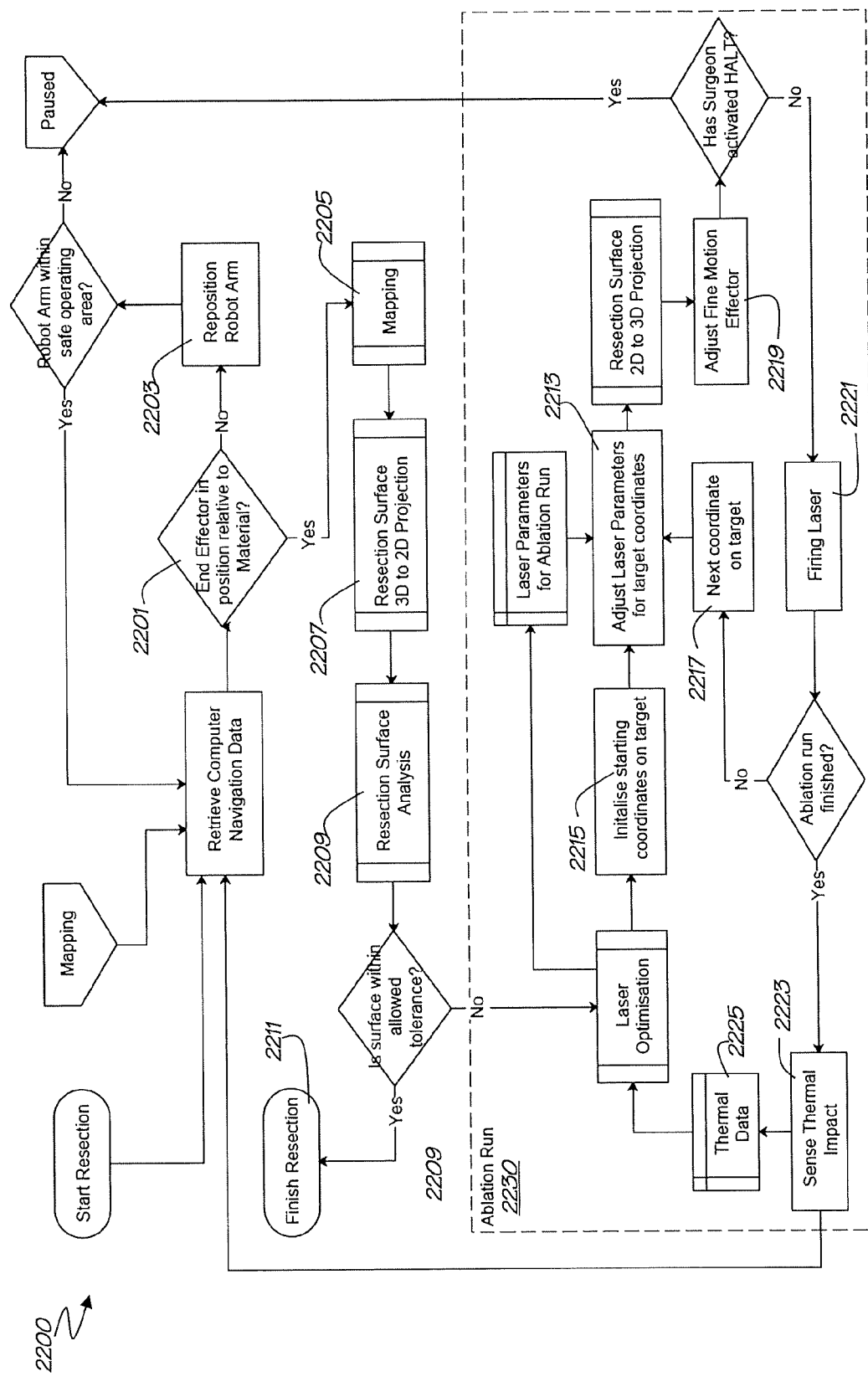
FIG. 22 depicts a flow chart of actions performed during a resection operation of the planning operation of FIG. 21.

FIG. 22 depicts a flow chart of a method 2200 of actions performed during a resection operation of the system 10.

In the embodiment, a planned state of the biological tissue 12 after the at least one action of work has been performed thereon comprises an ideal plane or mesh in 3D space that needs to be exposed on the biological tissue 12 via subtractive ablation. The resection process is given the ideal plane or mesh for use in the processing.

The process confirms 2201 that the robot arm 105 is positioned at the correct location above the biological tissue 12. Given that the biological tissue 12 is not held exactly still it is necessary to constantly check and readjust 2203 the absolute position of the end effector 28 as herein described to maintain the same relative location. The location of the biological tissue 12 is retrieved from the mapping component, which in turn had retrieved the positions of fiducial markers 70 via the position sensor controller 171.

A 'safe operating area' is a virtual region that the robot arm 105 is not allowed to leave. Should the robot arm 105 attempt to reposition outside this safe operating area then the system 10 is operable to be put into a paused state until released by the user. This is an added safety mechanism to prevent the robot arm 105 from making physical contact, with surgical staff for example.

At the correct relative location, the system 10 is operable to scan the geometry of the target using the 3D metrology sensor 190. Several sensors of the sets of sensors 101 and 102 then scan 2205 the biological tissue 12 to determine the composition thereof. These sensors include those for hyperspectral imaging, Raman spectroscopy, thermal imaging, microscopy, acoustic and optical imaging. The collective results of the scans are analysed, combined and stored by the system 10 and made available by the mapping component.

The resection surface is converted 2207 from 3D information into 2D maps to extract the data unnecessary for processing the surface topography and composition in the resection surface analysis. The geometry is reduced to a 2D height map with associated hyperspectral and thermal 2D maps overlays in the same coordinate space.

The process analyses 2209 the desired resection geometry with the height map and mapping to determine the current conformity of the surface to the tolerances required for an accurately completed resection. If the surface is complete within tolerance then this resection is done 2211.

Otherwise, the system 10 is operable to calculate an ablation run 2230—a series of laser ablations that will reduce the surface by a layer of material.

The system 10 is operable to perform an analysis of the extent to which the post-action state of the biological tissue 12 aligns with the planned state of the biological tissue 12 to determine the parameters of the ablation run required.

Particularly, in the embodiment, the process analyses 2209 the resection volume in conjunction with the mapping composition results and 3D surface data, composition data and any thermal data retrieved from prior ablations to determine the current conformity of the sensed geometry to an optimal set of parameters for the laser light beam 30 to perform an ablation run 2230 to safely and efficiently reduce the surface of the biological tissue 12 without burning or causing necrosis.

As part of the analysis, the system coordinator 200 (of FIG. 13) is operable to generate based on input, and/or receive as input, at least one third representation of the biological tissue 12. In the embodiment, the at least one third representation of the biological tissue 12 comprises a representation of a state of the biological tissue 12 corresponding to an actual post-action or final state of the biological tissue 12 after the at least one action of work has been performed thereon (evaluation 2909). The at least one third representation of the biological tissue 12 includes parameters that describe or provide an indication of one or more characteristics of the biological tissue 12 and, in the embodiment, comprises a map or model of the post-action state of the biological tissue 12.

The system 10 is operable to initialize the starting coordinates 2215 on the target biological tissue 12 for the beginning of the ablation run.

During the ablation run the system 10 is operable to adjust 2213 the laser parameters such as the current and pulse duration parameters in real-time to the pre-calculated values for each target coordinates.

The process calculates the position of the 2D map target coordinates in 3D space.

The fine motion means, in the preferred embodiment a scan head 117, is operable to reposition the direction of the laser light beam 30 to point to the target on the surface of the biological tissue 12. Each firing sequence of the laser light beam 30 needs to be made to a point on the biological tissue 12 to micron-scale precision in the embodiment.

The system 10 is operable to check to ensure that the surgeon 16 has not halted the system 10 prior to every firing of the laser light beam 30 in the embodiment.

The laser current source 131 is directed to fire the laser light beam 30 using the current parameter settings.

If the ablation run has not been completed yet, the next coordinates in the map are selected 2217, the laser parameters are adjusted 2213 and the system 10 repeats the repositioning 2219 and firing 2221 of the laser light beam 30.

Once the ablation run has completed, the surface is sensed 2223 with the thermal sensor 184 for heat impact. The thermal data 2225 arising from such sensing is made available to the laser optimisation component for future ablation runs.

The location of the biological tissue 12 is checked for positioning the end effector 28 and the process of mapping, analysing and ablating is repeated.

Regarding robot motion, the system 10 is operable to position the sensors, laser optics and ancillary tools in the end effector 28 above and at a set relative distance from the biological tissue 12.

The positioning depends on the joint angles of the robot arm 105. The calculation of the joint angles for the end position and all transition positions in-between involves inverse kinematics.

Preferably, the system 10 will rely on and use provided inverse-kinematics infrastructure in the robot arm 105 to determine the joint angles and movement required to transition the end effector 28 from one Cartesian point to another. This will result in the robot motion component being a façade for that existing functionality.

Should the robot arm controller 106 not provide the required functionality then it will be necessary to use an existing or custom library that supports the inverse kinematic calculations.

Figure 23:
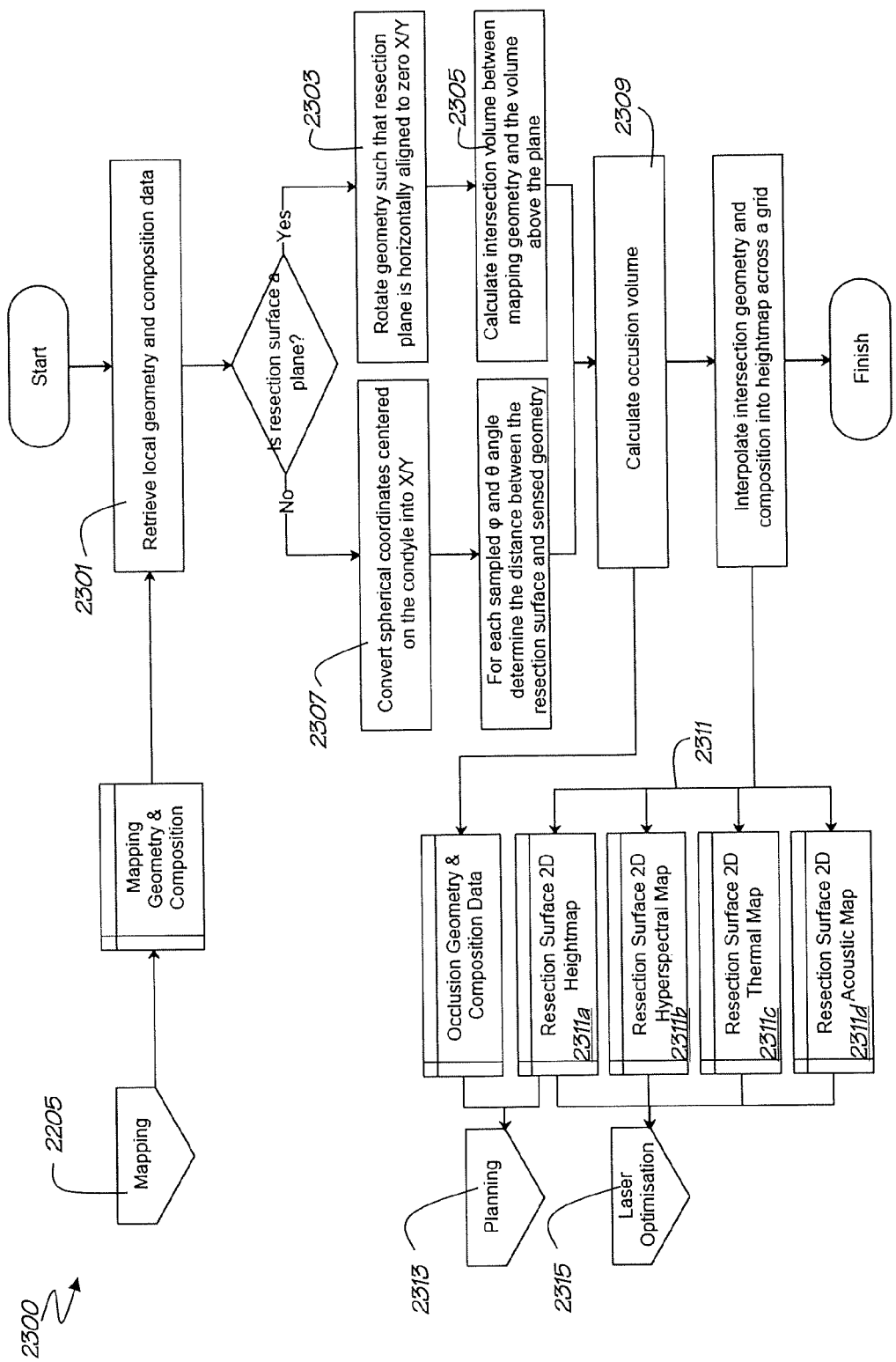
FIG. 23 depicts a flow chart of actions performed during a resection surface 3D to 2D projection of the resection operation of FIG. 22.

FIG. 23 depicts a flow chart of a method 2300 of actions performed during a resection surface 3D to 2D projection.

When a resection is being performed, the system 10 is operable to maintain an understanding of the sensed geometry as it applies to the subtractive process of reducing biological tissue 12 to the desired geometry.

The mapping component holds the mesh and other ancillary data that describes the geometry and composition of biological tissue 12. The projection process uses that information to create a specialised derived data source orientated for the resection parameters.

The process is operable to retrieve 2301 the geometry and composition data from the mapping component.

Where the resection surface is a plane, the mapping geometry is rotated 2303 around the centre of the transepicondylar axis such that the coordinates of the resection plane is aligned to the zero axis of the X and Y coordinates (where Z is up/down).

The intersection volume between the mapping geometry and the positive Z area above the X/Y plane is calculated 2205. The part of the volume that is bone is the section that needs to be subtractively ablated. The remaining volume is potentially occluding material that needs to remain and should not be ablated, nor should it be in line with a ray projection calculation between the laser beam origin and any target point for ablation.

As the bone volume X/Y plane has been aligned to the resection plane, the Z value can simply be viewed as a mesh at varying heights above the desired flat end result. A height map can be interpolated from the mesh by applying a grid with a resolution of the minimum scale required to perform the flat plane ablation.

Where the resection surface is not a plane, the geometric mesh is calculated 2307 in spherical coordinates from the centre of the condyle (as defined as ¼ or ¾ position on the transepicondylar axis depending on which condyle the resection surface is located).

The $\varphi$ and $\theta$ angle is sampled at sufficiently small degrees such that, at the average distance to the surface, the grid spacing is around 50 microns. In essence, this allows for the sampled $\varphi$ to become the x axis on a 2D map, and for the $\theta$ angle to become the y axis. The ideal resection surface is considered to be at zero height and any existing biological tissue 12 above that is treated as positive height value. This newly created height map can then be analysed and processed the same as if the resection was occurring on a plane.

The process is then operable to determine 2309 the occlusion geometry by removing any geometry that does not exist within the intersection of the mapping geometry and an inclusion shape.

For the femoral head the inclusion shape comprises the intersection of:

(1) two ovals centred on the ¼ and ¾ position of the transepicondylar axis with a width radius (along the axis) of ¼ the transepicondylar axis and a height radius of the transepicondylar axis; and (2) a solid cylinder with the long axis and height of the transepicondylar axis and a radius of ¾ the transepicondylar axis.

For the tibial plateau the inclusion shape comprises a solid cylinder with the long axis in line with the cortex with a radius of ½ the distance of the width of the plateau.

The process is then operable to create a set of 2D maps 2311 in the same coordinate space for the height, hyperspectral values and thermal values. This reduced dimensionality data is used by various components of the system 10 to analyse the resection progress and determine the laser optimisation for ablation.

As part of the analysis, the system coordinator 200 (of FIG. 13) is operable to compare the representation of the post-action state of the biological tissue 12 with the representation of the planned state of the biological tissue 12 to assess the extent to which the state of the biological tissue 12 after the at least one action of work has been performed thereon aligns with the planned state of the biological tissue 12, (i.e. mapping step 2205 of FIG. 22 and method 2300 of FIG. 23) and thereby assess the extent to which the action has been formed successfully. A measure of success is provided based on the extent to which the representation of the post-action state of the biological tissue 12 fits and aligns with the representation of the planned state of the biological tissue 12 to prescribed tolerances. This process can be summarised as determining how the sensed reality should be represented internally in a useful way for processing and determining the laser ablation objectives. In FIG. 23 it can be seen that there are four (4) representations 2311 further used by the Planning 2313 and Laser Optimisation 2315 processes including: the "Re-section surface 2D Heightmap" 2311a, "Re-section Surface 2D Hyperspectral Map"

2311b, "Re-section Surface 2D Thermal Map" 2311c, and "Re-section Surface 2D Acoustic Map" 2311d.

Figure 24:
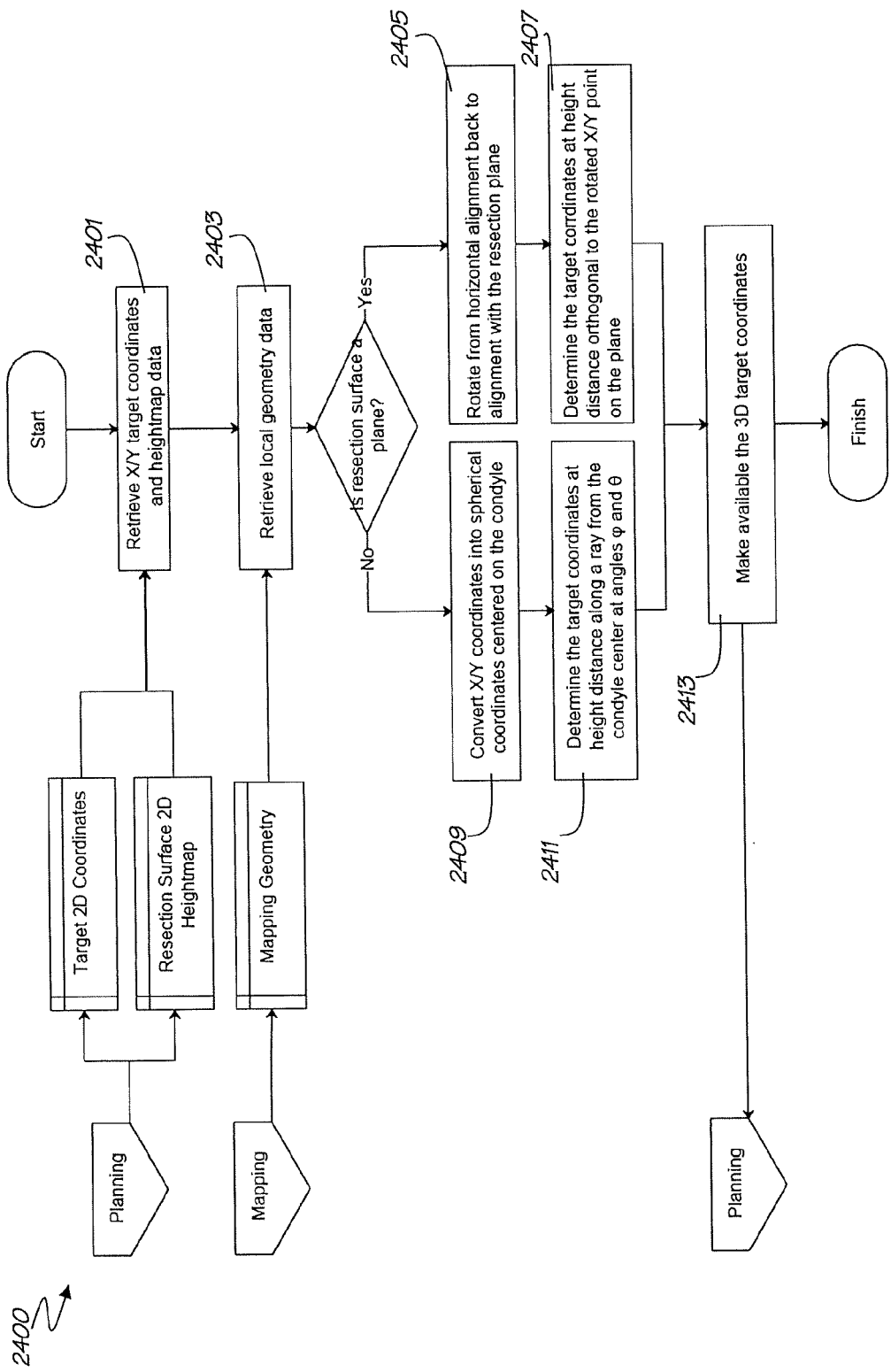
FIG. 24 depicts a flow chart of actions performed during a resection surface 2D to 3D projection of the resection operation of FIG. 22.

FIG. 24 depicts a flow chart of a method 2400 of actions performed to reverse the 3D to 2D projection that was used to reduce the dimensionality of the data. The system 10 requires the 3D location of each target coordinate on the 2D map for positioning the laser light beam 30 to ablate the correct biological tissue 12.

The process is operable to retrieve 2401 the X/Y target coordinates from an ablation run and the height map data in the 2D map. The local geometry data is also retrieved 2403 from the mapping component.

If the resection surface is a plane then the X/Y target coordinates are rotated 2405 from the horizontal alignment back into alignment with the resection plane. The 3D target coordinates can then be determined 2407 at the height distance orthogonal to the now rotated plane.

If the resection surface is not a plane the process is operable to convert 2409 the X/Y coordinates into φ and θ angle spherical coordinates centred on the condyle. The 3D target coordinates can then be determined 2411 at the height distance along a ray from the condyle centre at the angles φ and θ.

The resulting 3D coordinates are made available 2413 such that the system 10 can then target the biological tissue 12 at the correct location in world coordinates.

Figure 25:
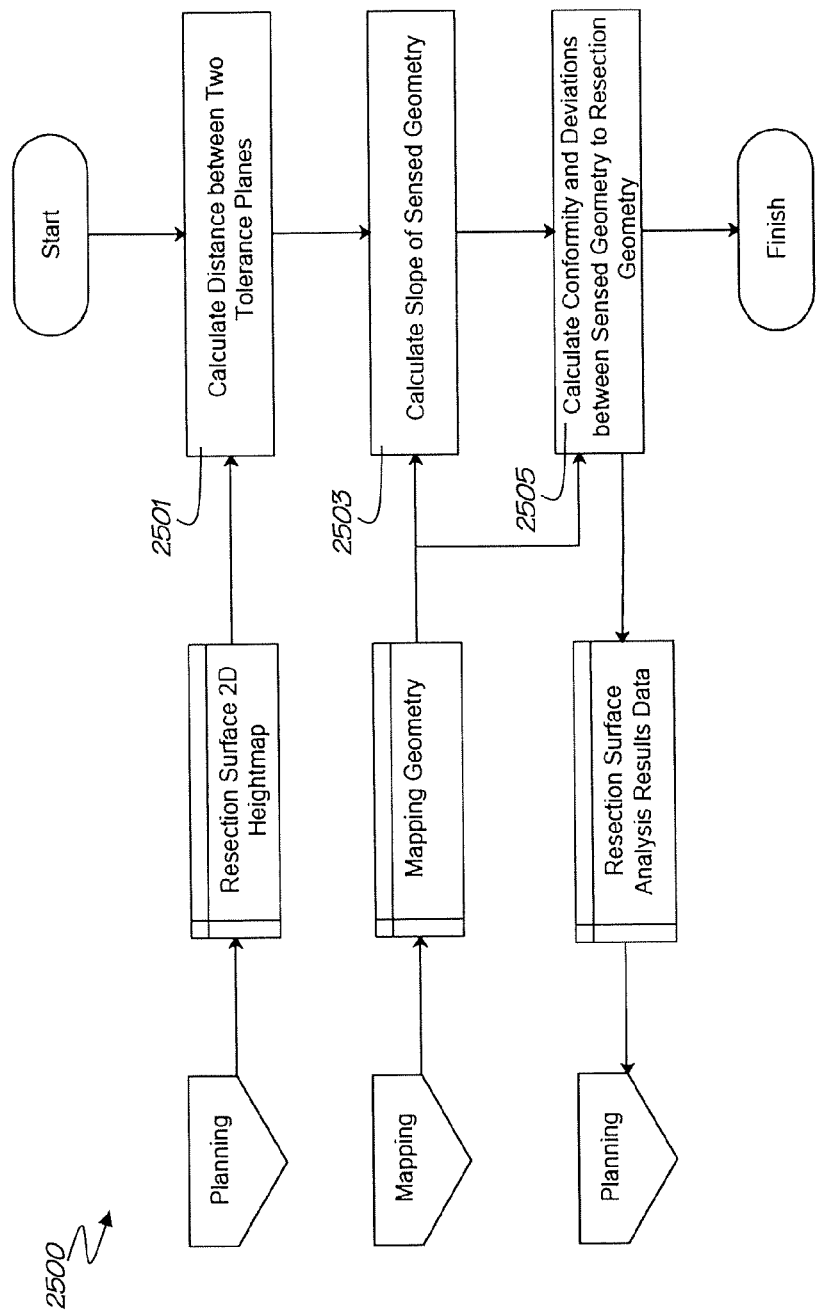
FIG. 25 depicts a flow chart of actions performed during a resection surface analysis operation of the controller of FIG. 1 and operation of FIG. 22.

FIG. 25 depicts a flow chart of a method 2500 of actions performed during a resection surface analysis operation of the system 10.

The system 10 is operable to calculate 2501 the distance between two tolerance planes that enclose all the geometry of the surface. This provides one quantification of the overall flatness of the geometry.

The system 10 is also operable to calculate 2503 the slope of the geometry by best fitting a plane to the vertices. This slope information is important to the overall alignment of the prosthetic component.

The system 10 is operable to then quantify 2505 the specific deviations and conformity that the surface geometry has compared to the ideal geometry of the surface plan. This includes the primary profile, roughness profile, waviness profile and shape profile which may be determined using standard methods of surface attribute analysis.

As part of the analysis, the system coordinator 200 is operable to generate based on input, and/or receive as input, at least one second representation of the biological tissue 12. In the embodiment, the at least one second representation of the biological tissue 12 comprises a representation of a state of the biological tissue 12 corresponding to a planned or intended state of the biological tissue 12 after the at least one action of work has been performed thereon. The at least one second representation of the biological tissue 12 includes parameters that describe or provide an indication of one or more characteristics of the biological tissue 12 and, in the embodiment, comprises a map or model of the planned state of the biological tissue 12.

The resulting set of analysis data is provided to the planning system for use in prosthetic component fit and alignment analysis.

Figure 26:
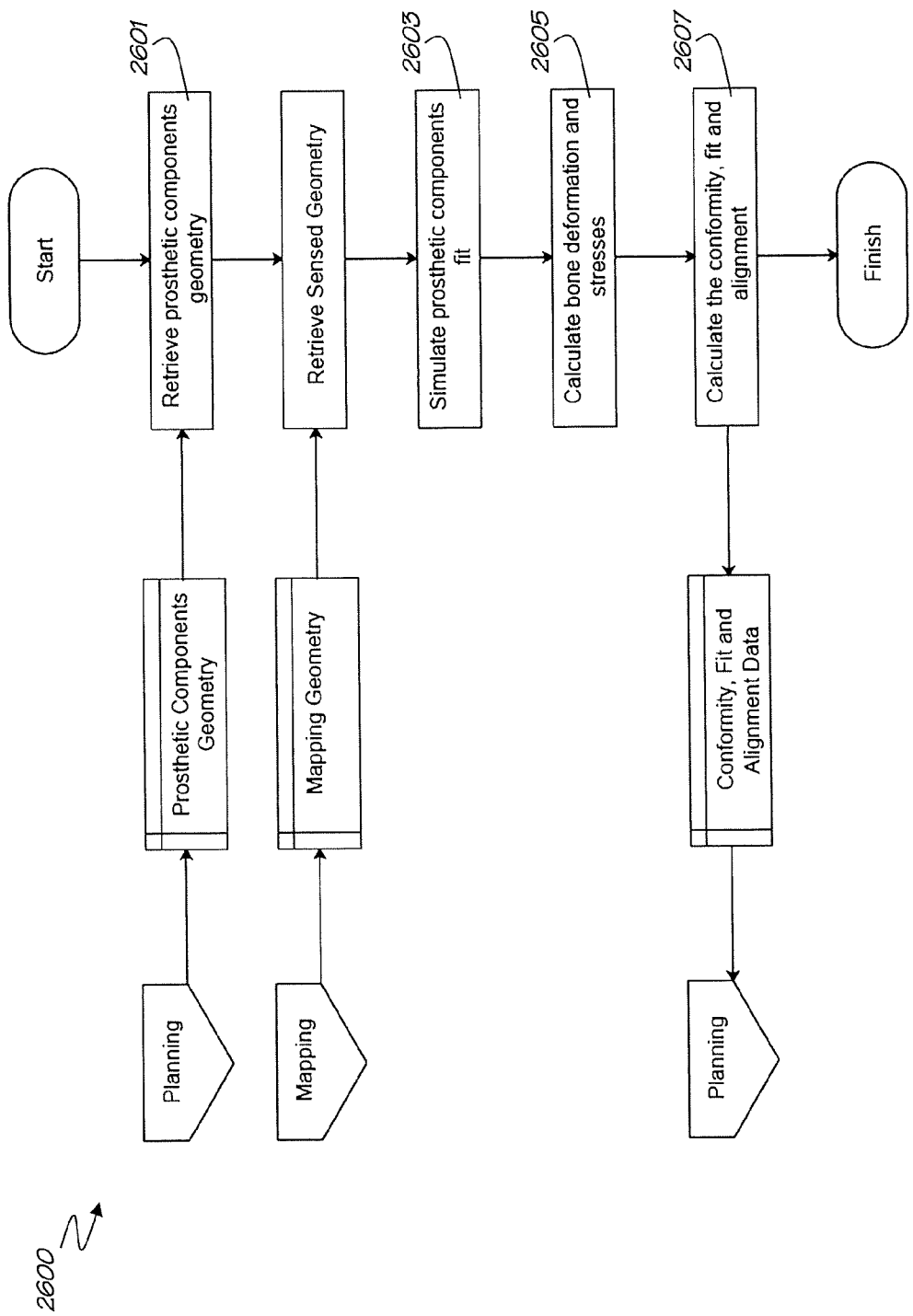
FIG. 26 depicts a flow chart of the actions performed during a prosthetic components' fit and alignment analysis operation of the prosthetic resections of FIG. 21.

FIG. 26 depicts a flow chart of a method 2600 of actions performed during a prosthetic components fit and alignment analysis operation of the system 10.

The prosthetic components geometry is retrieved 2601 from the loaded plan for processing against the retrieved mapping geometry. The system 10 is operable to simulate 2603 the prosthetic component onto the mapping geometry by way of finite element method to detect/calculate 2605 the stresses and deformations that are likely to result to the fit and subsequent alignment of the component to the mechanical axis of the patient 14.

The quantified 2607 conformity, fit and alignment data is made available to the system 10 for automated and surgeon 16 decision making on the resections being performed. The results are also presented to the surgeon 16 via the display 20.

Figure 27:
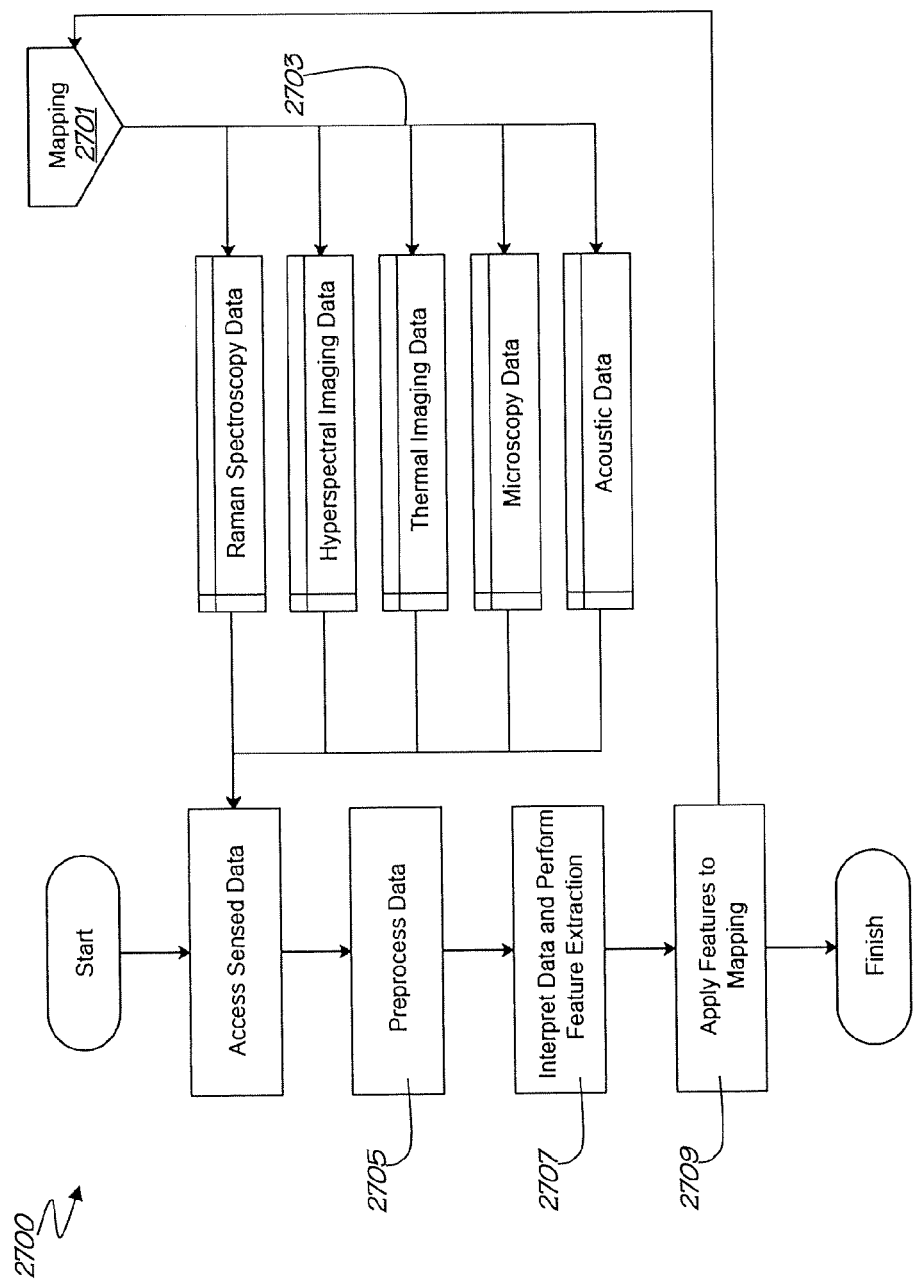
FIG. 27 depicts a flow chart of actions performed during a bioanalysis operation of the controller of FIG. 13.

FIG. 27 depicts a flow chart of a method 2700 of actions performed during a bioanalysis operation of the system 10 where the sensing information is analysed for composition features of the biological tissue 12. This helps to prevent the system 10 from targeting soft tissue or otherwise causing collateral damage to parts of the patient 14 that should not be resected.

The mapping component 2701 has already aligned all the sensor data 2703 to the geometry surface to account for the sensors being placed at different viewpoints from the biological tissue 12.

In embodiments of the invention, the data can be pre-processed 2705 to remove noise and artefacts in the sensed information that would obscure the feature detection.

The system 10 is operable to perform feature extraction 2707 on the data by comparing the data signal with known signatures that have been determined from prior testing. This can be done for the same target location across the various measurement sensors of the sets of sensors 101 and 102 to determine a prediction of the composition for each point.

The system 10 is operable to then apply 2709 the bioanalysis predictions back to the mapping component to provide additional metadata for use by other parts of the system 10 to guide decisions and actions.

Figure 28:
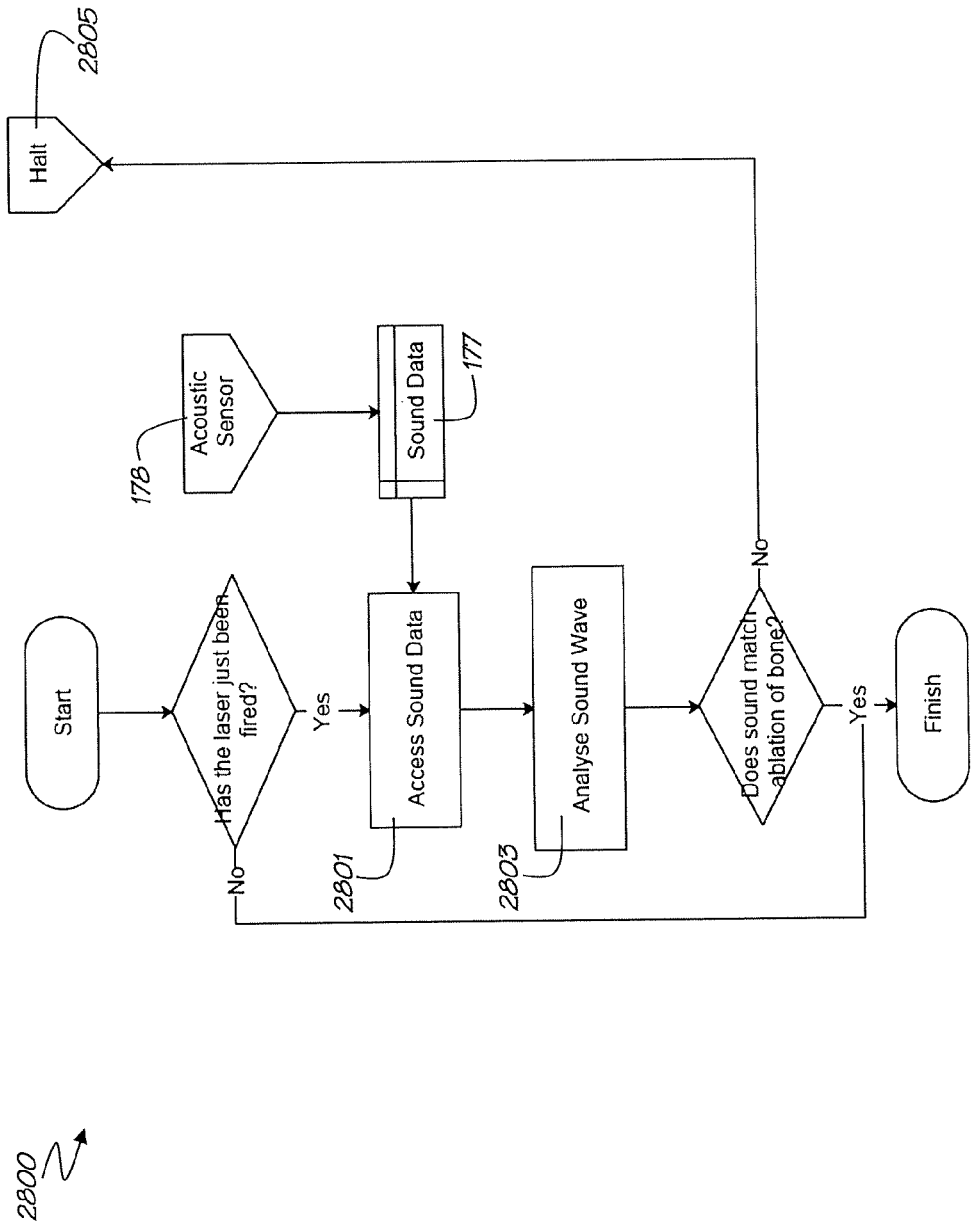
FIG. 28 depicts a flow chart of actions performed during an acoustic analysis operation of the controller of FIG. 13.

FIG. 28 depicts a flow chart of a method 2800 of actions performed during an acoustic sound analysis operation of the system 10.

The bioanalysis component also uses the acoustic sensor 178 to determine if the sound of an ablation has been performed on hard biological tissue.

The sound profile produced by laser ablating bone is distinct from the sounds produced by other materials. The system 10 is operable to utilise this to increase the overall safety during an ablation run. Method 2800 comprises the step of receiving 2801 sound data 177 picked up by an acoustic sensor 178 from the environment and around the biological tissue 12 at the working site and analysing 2803 the sound data to determine whether the received sound data matches that expected when the laser impact a bone material. When an unexpected sound is received and analysed, the system 10 is operable to halt 2805 the ablation. Due to the speed of the laser pulses this may not prevent a few more laser bursts from striking a non-bone surface until the processing of the prior sound profile has completed, but can prevent further damage.

The system 10 is operable to detect if the laser light beam 30 has just been fired and access the acoustic sensor 178 sound data comprising a sound wave. The sound wave is analysed to detect if it matches, by way of distinct frequency and amplitude, the profile of hard biological tissue being ablated.

If the sound does not match then the system 10 is signalled to halt operation.

Figure 29:
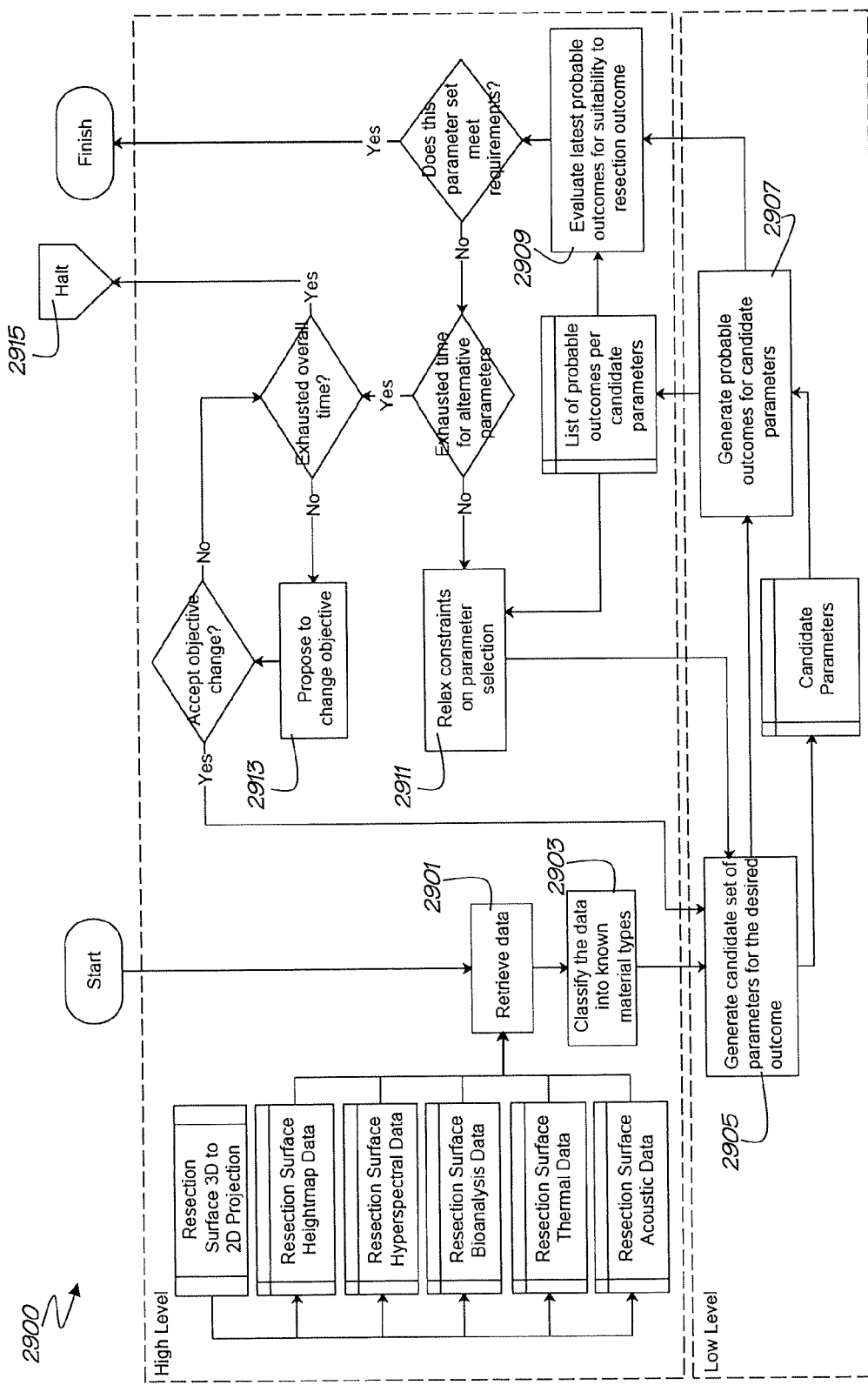
FIG. 29 depicts a flow chart of actions performed during a laser optimisation operation of the controller of FIG. 13.

FIG. 29 depicts a flow chart of a method 2900 of actions performed during a laser optimisation operation of the system 10.

The purpose of this component is to perform risk-sensitive decision-making for autonomous control of the laser parameters in the minimally-observable environment.

The ablative laser is controlled through several co-dependent parameters that influence how it interacts with different materials. The task of laser-based machining is complex as it involves tuning these parameters to suit the material being ablated. This material differs between patients depending on the type of bone and its composition (mineral, collagen and water content), as well as factors such as gender, age and ethnicity. The laser optimisation determines the optimal set of parameters for the laser light beam 30 to safely ablate hard tissue. In addition, the system 10 is operable to quantify its level of confidence at every stage of the decision-making process and has the ability to output human-intelligible diagnostic information.

The laser optimisation component retrieves 2901 data from the resection surface analysis component. This has been pre-processed into a series of 2D maps: height, hyperspectral, bioanalysis, thermal and acoustic. The 2D map is either an oriented resection plane or a map from spherical coordinates for a resection surface.

From this base of data, the component can classify 2903 the data into known material types. As a low level function, a set of candidate laser parameters is generated 2905 that is predicted to result in the desired outcome. These are tested in a model to determine 2907 the most likely outcome for those candidates.

The suitability of those outcomes is then evaluated 2909. In some instances, there could be undesirable results predicted, so the component has the option to relax 2911 some of the constraints on parameter selection before generating 2905 a new set of parameters for testing.

In cases where the component has exceeded the time period to trial alternatives, the objective can be changed 2913 to facilitate parameter selection that could achieve a partial solution rather than have no solution.

If the component exhausts the time period for alternative parameters and no solutions have been reached, then the system 10 is placed in halt 2915.

Safety, monitoring and verification operations of the system 10 comprise:
  correct cutting position;
  expected tissue type; and
  expected effects (thermal, stress, material removal).

Figure 30:
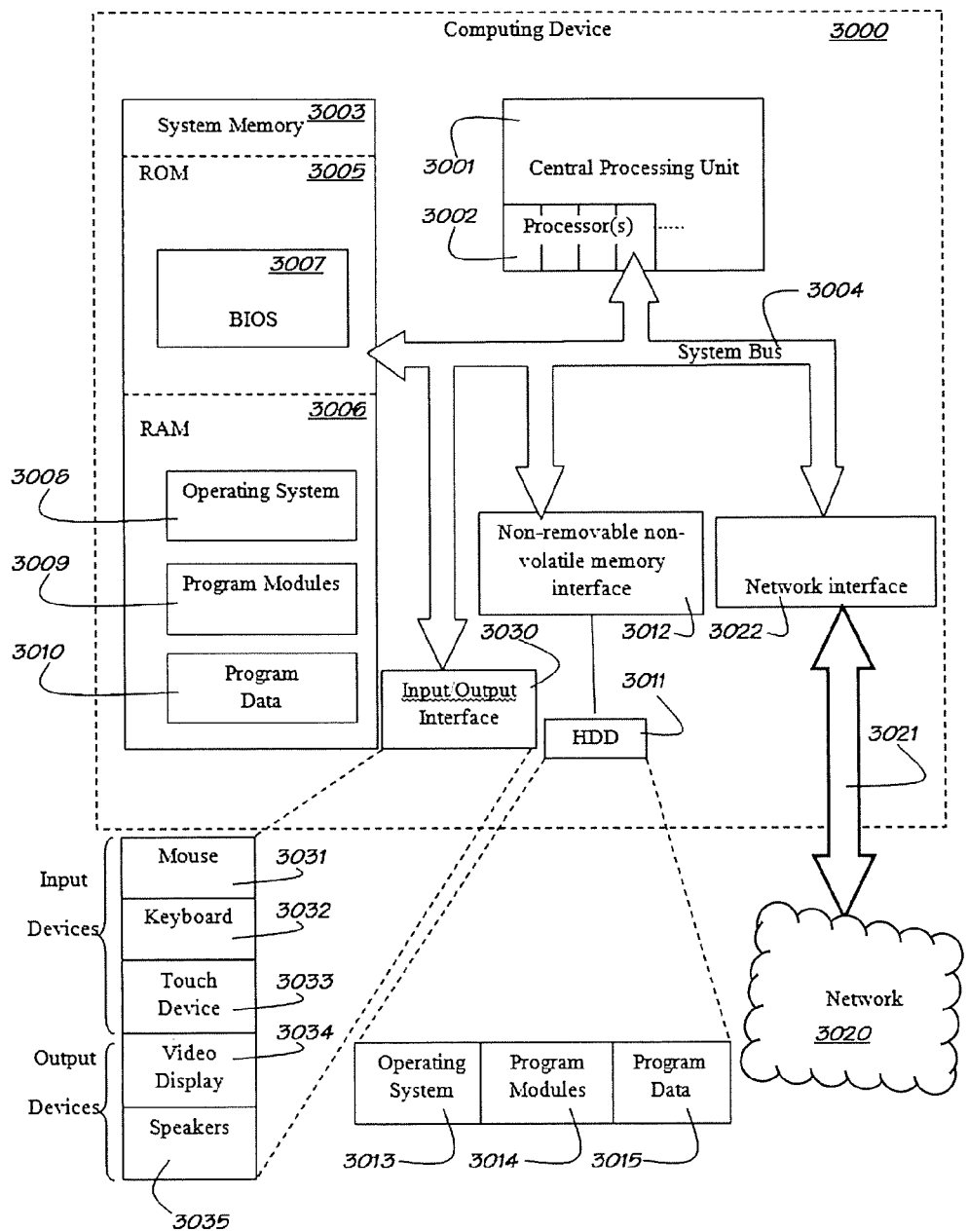
FIG. 30 depicts a computing device on which the various embodiments described herein may be implemented in accordance with an embodiment of the present invention.

Outcomes and results that may arise from operation of the system 10 include:
  efficiency, including in the cutting/shaping rate;
  geometric effects, including in the cut physical attributes; and
  side effects, including thermal effects:

The methods 1400 to 2900 (and associated sub methods depicted in FIGS. 14 to 29 may be implemented using a computing device/computer system 3000, such as that shown in FIG. 30 wherein the processes of FIGS. 14 to 29 may be implemented as software, such as one or more application programs executable within the computing device 3000. In particular, the steps of the methods disclosed herein are effected by instructions in the software that are carried out within the computer system 3000. The instructions may be formed as one or more code modules, each for performing one or more particular tasks. The software may also be divided into two separate parts, in which a first part and the corresponding code modules performs the described methods and a second part and the corresponding code modules manage a user interface between the first part and the user. The software may be stored in a computer readable medium, including the storage devices described below, for example. The software is loaded into the computer system 3000 from the computer readable medium, and then executed by the computer system 3000. A computer readable medium having such software or computer program recorded on it is a computer program product. The use of the computer program product in the computer system 3000 preferably effects an advantageous apparatus for laser shaping of biological tissue including bone.

With reference to FIG. 30, an exemplary computing device 3000 is illustrated. The example computing device 3000 can include, but is not limited to, one or more central processing units (CPUs) 3001 comprising one or more processors 3002, a system memory 3003, and a system bus 3004 that couples various system components including the system memory 3003 to the processing unit 3001. The system bus 3004 may be any of several types of bus structures including a memory bus or memory controller, a peripheral bus, and a local bus using any of a variety of bus architectures.

The computing device 3000 also typically includes computer readable media, which can include any available media that can be accessed by computing device 3000 and includes both volatile and non-volatile media and removable and non-removable media. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 3000. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 3003 includes computer storage media in the form of volatile and/or non-volatile memory such as read only memory (ROM) 3005 and random access memory (RAM) 3006. A basic input/output system 3007 (BIOS), containing the basic routines that help to transfer information between elements within computing device 3000, such as during start-up, is typically stored in ROM 3005. RAM 3006—typically contains data and/or program modules that are immediately accessible to and/or presently being operated on by processing unit 3001. By way of example, and not limitation, FIG. 30 illustrates an operating system 3008, other program modules 3009, and program data 3010.

The computing device 3000 may also include other removable/non-removable, volatile/non-volatile computer storage media. By way of example only, FIG. 30 illustrates a hard disk drive 3011 that reads from or writes to non-removable, non-volatile magnetic media. Other removable/non-removable, volatile/non-volatile computer storage media that can be used with the example computing device include, but are not limited to, magnetic tape cassettes, flash memory cards, digital versatile disks, digital video tape, solid state RAM, solid state ROM, and the like. The hard disk drive 3011 is typically connected to the system bus 3004 through a non-removable memory interface such as interface 3012.

The drives and their associated computer storage media discussed above and illustrated in FIG. 30, provide storage of computer readable instructions, data structures, program modules and other data for the computing device 3000. In FIG. 30, for example, hard disk drive 3011 is illustrated as storing an operating system 3013, other program modules 3014, and program data 3015. Note that these components can either be the same as or different from operating system 3008, other program modules 3009 and program data 3010. Operating system 3013, other program modules 3014 and program data 3015 are given different numbers hereto illustrate that, at a minimum, they are different copies.

The computing device also includes one or more input/output (I/O) interfaces 3030 connected to the system bus 3004 including an audio-video interface that couples to output devices including one or more of a video display 3034 and loudspeakers 3035. Input/output interface(s) 3030 also couple(s) to one or more input devices including, for example a mouse 3031, keyboard 3032 or touch sensitive device 3033 such as for example a smartphone or tablet device.

Of relevance to the descriptions below, the computing device 3000 may operate in a networked environment using logical connections to one or more remote computers. For simplicity of illustration, the computing device 3000 is shown in FIG. 30 to be connected to a network 3020 that is not limited to any particular network or networking protocols, but which may include, for example Ethernet, Bluetooth or IEEE 802.X wireless protocols. The logical connection depicted in FIG. 30 is a general network connection 3021 that can be a local area network (LAN), a wide area network (WAN) or other network, for example, the internet. The computing device 3000 is connected to the general network connection 3021 through a network interface or adapter 3022 which is, in turn, connected to the system bus 3004. In a networked environment, program modules depicted relative to the computing device 3000, or portions or peripherals thereof, may be stored in the memory of one or more other computing devices that are communicatively coupled to the computing device 3000 through the general network connection 3021. It will be appreciated that the network connections shown are examples only and other means of establishing a communications link between computing devices may be used.

In embodiments of the invention, one or more of the described, additional and/or alternative operations performed by the system 10 occur semi-automatically or automatically, without requiring human intervention.

It can be appreciated that in the implementation described a laser is coupled with a robot and the couple is integrated with optical and mechanical sensors to provide a closed loop subtractive laser-assisted machining of bone system (machine), allowing for computationally derived process parameters for design and selection of operating parameters during real orthopaedic surgery in a clinical environment for rapid and accurate outcome.

It will be appreciated that the described embodiment of the invention provides several advantages.

The embodiment of the system 10 is capable of machining hard biological tissue with submillimetre precision, and includes features of: non-invasive real-time optical sensing; intelligent and dynamic control of laser parameters; and post-machining biological validation.

The embodiment of the invention: uses non-invasive optical sensing to ensure precision control, safety and localisation of the laser; involves the development and teaching of an artificial intelligence system to control the process of laser shaping in real-time; involves validation of the optimised laser parameters against cellular and molecular assessments; and optimises the performance of the integrated system.

Embodiments of the invention may allow for surgery with improvement in accuracy of the cut, improvement in submillimetre precision of the cut, improvement in safety due to the monitoring ability, avoiding the need of collateral damage, improvement in the biological quality of the cut surface by optimizing the parameters of the lasers using analytical and machine learning techniques.

It is anticipated that, in the first world alone, more than 2 million patients per year could benefit from technology of embodiments of the invention.

Embodiments of the invention provide for high accuracy and submillimetre precision through intelligent adaptive shaping, low thermal and biomechanical impact, vibration free shaping; and multiple redundant safety.

Embodiments of the invention provide for patient customised laser ablation that is optimised in real-time. The system of embodiments takes in continuous feedback from sensors and models and post ablation assessment (biological status of residual tissue) and adjusts laser parameters to optimum. Resulting in maximum or improved tissue removal for absolute minimal or reduced thermal impact.

Via embodiments of the system, a laser ablation can be provided that: is customisable to each patient; has no/minimal/reduced thermal impact (biological quality); is geometrically precise; has adjustable parameters in real time; and has multiple levels of safety (including guide laser, sensors, post cut sensing, and surgeon control).

The submillimetre precision, low mechanical and thermal impact afforded by embodiments of the invention may advantageously lead to a revolution in implant manufacturing, and also to a significant improvement in patient outcome and quality of life.

Embodiments of the invention may allow for minimal human orthopaedic surgery with minimal human intervention, semi- or full automation; high precision, rapid procedure, minimal invasive tissue-damage, reduced or no blood transfusion, improved implant integration, and reduced cost.

The embodiment of the invention advantageously uses a laser to ablate biological tissue, doing so quickly within the same time constraints of surgery, safely, accurately, and cleanly.

To ablate hard biological tissue quickly within the same time constraints of surgery, the described embodiment increases or maximizes the volume of material that can be removed taking into account safety and accuracy. It is capable of ablating material faster when the target location's surrounding hard biological material will be damaged and will later need to be removed in any case. It runs liquid to be applied to the tissue for cooling the tissue during the ablation procedure bundled with the cold coolant from the base unit to the end effector to cool the liquid. Laser optimization is based on the dynamics of interaction with hard biological tissue to increase or maximize rate of machining. It performs the ablation in "runs" that encapsulates a series of laser ablations in quick bursts between sensing. This may provide an optimal balance of sensing (assured) and speed.

To ablate hard biological tissue safely, the described embodiment protects the final re-sectioned tissue surface from damage (necrosis/thermal shock/cracks). This is achieved by using low laser power to ensure that the final surface is undamaged, or to reduce damage to the final surface, and by using a water spray to introduce cool water to the material to assist in laser ablation and protect the material from thermal damage. It is further achieved by protecting operating staff with a consumable shield that helps to prevent inadvertent injury or damage from objects coming into contact with the laser beam.

To ablate hard biological tissue accurately, the described embodiment uses a robotic arm to position the end effector above the target, then uses a scan head to direct the laser with greater accuracy. Additionally, it uses a 3D metrology sensor to map the geometry of the material. In this regard, it reduces the dimensionality of the 3D geometry into a series of 2D maps based on either a plane or spherical coordinate system, allowing for faster processing and an easier to understand display for the surgeon 16. All other sensor information can be overlaid on the same 2D map. Resection surface analysis allows for best fit and alignment with the patient. It uses a hyperspectral sensor to differentiate between tissue types. It uses an acoustic sensor to detect if the laser has impacted an unexpected object. It uses a lasered fiducial mark on the material to allow for highly accurate tracking (over and above what is provided with the position sensor). It provides intelligent control over the ablation process, using feedback of sensor data to refine the laser machining process and having a master system coordinator allowing for simulation, testing, and data logging (big data).

To ablate hard biological tissue cleanly, the described embodiment incorporates a particle collector into a consumable shield that acts as a vacuum bag. Additionally, it uses a series of traps and filters to store the particulate matter, and thereby saves the final HEPA filter from becoming full quickly with large scale particles.

It will be appreciated by those skilled in the art that variations and modifications to the invention described herein will be apparent without departing from the spirit and scope thereof. The variations and modifications as would be apparent to persons skilled in the art are deemed to fall within the broad scope and ambit of the invention as herein set forth.

Also, future patent applications may be filed in Australia or overseas on the basis of, or claiming priority from, the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

The invention claimed is:

1. A laser osteotomy system for shaping hard biological tissue including bone, the system comprising:
a tool comprising a laser operable to perform at least one action of work comprising laser ablation;
positioning means for positioning the tool relative to the hard biological tissue to perform the at least one action of work;
an input means;
an optical sensor operable to measure light interaction with the hard biological tissue and an environment around the hard biological tissue; and
a controller to:
receive input via the input means, the input comprising but not limited to the light waves measured by the optical sensor,
perform processing on the input for mapping and identification of the hard biological tissue and an environment around the hard biological tissue,
wherein mapping comprises analyzing the light waves to determine the topography and proximity of the hard biological tissue and an environment around the hard biological tissue to the tool,
wherein identification comprises analyzing the correlation of reflected light waves to one or more biological tissue spectral signatures, and
on the basis of the processing, control the positioning means and the tool to work the hard biological tissue; and
wherein the system is adapted to be used to perform arthroplasty and revisions.

2. The system according to claim 1, wherein processing of the received input performed by the controller, under control of the electronic program instructions, comprises an analysis of the received input and a making of a decision on the basis of the analysis and criteria relevant to the at least one action of work to control the positioning means and the tool to work the hard biological tissue;
wherein the criteria comprises at least one of: speed of the at least one action of work; accuracy of the at least one action of work; safety of the at least one action of work; and cleanliness of the at least one action of work.

3. The system according to claim 2, wherein as at least part of the analysis, the controller is operable to:
generate based on input, or receive as input, a first representation of the hard biological tissue;
generate a second representation of the hard biological tissue comprising a planned state of the hard biological tissue after the at least one action of work; and
make an assessment on the basis of the first representation of the hard biological tissue and the second representation of the hard biological tissue and use the assessment in the making of a decision.

4. The system according to claim 1, wherein the input means comprises at least one sensor system comprising a set of sensors, wherein individual sensors within the set of sensors are operable to monitor, sense, gather, or measure sensor data and/or information associated with or relating to one or more characteristics, properties and/or parameters of one or more of the system, the hard biological tissue, the surrounding environment, components, or systems or devices associated therewith or coupled thereto, wherein sensors of the set of sensors include those based on one or more of: Raman spectroscopy; hyperspectral imaging; optical imaging; thermal imaging; fluorescence spectroscopy, microscopy, acoustic, metrology, optical coherence tomography, laser power, and any non-invasive sensing.

5. The system according to claim 1, wherein operations performed by the system occur either semi-automatically under control of a surgeon, or automatically without requiring human intervention.

6. The system according to claim 1, wherein the processing comprises altering operation of the laser based on dynamics of interaction between a beam of radiation generated by the laser and the hard biological tissue to control an effect on the hard biological tissue wherein the effect includes: changing the rate of ablation; reducing or mitigating damage to the surface; and increasing the safety and accuracy of the ablation.

7. The system according to claim 1, wherein beams of radiation are generated by the laser in pulses, and laser pulses are batched into ablation runs comprising a pre-calculated set of pulses at different locations across the hard biological tissue.

8. The system according to claim 1, wherein the tool comprising the laser includes a sprayer for spraying a liquid on the hard biological tissue to assist in laser ablation and protect the hard biological tissue from thermal damage to at least some extent.

9. The system according to claim 1, wherein the system includes cooling means for cooling one or more components and liquids of the system.

10. The system according to claim 1, comprising shielding for providing protection during working of the hard biological tissue wherein one or more components are shielded to provide one or more of: to provide personal protection; to filter and/or trap and store particulate matter; and to protect the system from contamination through the use of disposable covering.

11. The system according to claim 1, wherein the positioning means comprises an articulated arm to which the tool is attached.

12. The system according to claim 1, wherein the positioning means comprises a fine motion controller adapted for accurately directing a working portion of the tool.

13. The system according to claim 1, wherein the processing comprises using the input to map the geometry of the hard biological tissue and the surrounding environment.

14. The system according to claim 1, further comprising a second input means, and wherein further processing by the controller comprises inferring from the second input means the biological tissue type and disposition including composition.

15. The system according to claim 1, wherein, when the input comprises input from an acoustic sensor, the processing comprises using the acoustic sensor input to detect if the tool has worked an unintended or unexpected biological tissue or material.

16. The system according to claim 1, wherein the tool is adapted to form one or more fiducial marks on the hard biological tissue for tracking thereof.

17. The system according to claim 1, wherein the controller comprises Artificial Intelligence (AI) software including machine perception or machine learning.

18. The system according to claim 1, wherein the tool includes dynamic focusing optics operable to dynamically change the focal length and focus beam diameter of the laser beam at a target distance.

* * * * *